US012807909B2

(12) United States Patent
Hovell et al.

(10) Patent No.: US 12,807,909 B2
(45) Date of Patent: Nov. 24, 2026

(54) BIOREACTORS AND BIOREACTOR FACILITIES THAT INCLUDE A PLURALITY OF BIOREACTOR TILES

(71) Applicant: Candice Hovell, Houston, TX (US)

(72) Inventors: Candice M. Hovell, Titusville, FL (US); Jeremy Mares, Orlando, FL (US)

(73) Assignee: Candice Hovell, Houston, TX (US)

( * ) Notice: Subject to any disclaimer, the term of this patent is extended or adjusted under 35 U.S.C. 154(b) by 1046 days.

(21) Appl. No.: 17/662,474

(22) Filed: May 9, 2022

(65) Prior Publication Data

US 2023/0357681 A1 Nov. 9, 2023

(51) Int. Cl.

*C12M 1/00* (2006.01)
*C12M 1/04* (2006.01)
*C12M 1/12* (2006.01)

(52) U.S. Cl.

CPC ............ *C12M 21/02* (2013.01); *C12M 23/06* (2013.01); *C12M 23/24* (2013.01); *C12M 31/08* (2013.01)

(58) Field of Classification Search

CPC ...... C12M 21/02; C12M 23/06; C12M 23/24; C12M 31/08

(Continued)

(56) References Cited

U.S. PATENT DOCUMENTS 9,867,861 B2 1/2018 Hagay et al.
10,336,795 B2 7/2019 Brain et al.

(Continued)

FOREIGN PATENT DOCUMENTS

AU 2012203478 A1 7/2012
DE 102019114979 A1 12/2020

(Continued)

OTHER PUBLICATIONS

Dogaris, Ioannis, Michael Welch, Andreas Meiser, Lawrence Walmsley, and George Philippidis. "A novel horizontal photobioreactor for high-density cultivation of microalgae." Bioresource Technology 198 (2015): 316-324.

(Continued)

*Primary Examiner* — Michael L Hobbs
*Assistant Examiner* — Lenora A Abel
(74) *Attorney, Agent, or Firm* — Wei Yu; Dentons Cohen & Grigsby, P.C.

(57) ABSTRACT

The present disclosure relates to bioreactors and bioreactor facilities that include a plurality of bioreactor tiles. One example system includes a system that includes a first bioreactor. The first bioreactor include a first housing. The first bioreactor also includes a plurality of first bioreactor tiles positioned within the first housing. Additionally, the first bioreactor includes a first fluid management system. Further, the first bioreactor includes a first illumination system. In addition, the first bioreactor includes a first environmental control system. Still further, the first bioreactor includes one or more first sensors positioned within the first housing. Yet further, the first bioreactor includes a first controller configured to receive data from the one or more first sensors and provided, based on the received data, one or more operating parameters to the first fluid management system, the first illumination system, or the first environmental control system.

11 Claims, 23 Drawing Sheets

(58) Field of Classification Search
USPC .................................................... 435/292.1
See application file for complete search history.

(56) References Cited

U.S. PATENT DOCUMENTS

| | | | | |
|---|---|---|---|---|
| 2004/0077075 | A1* | 4/2004 | Jensen | C12M 23/16 435/297.5 |
| 2006/0199260 | A1 | 9/2006 | Zhang et al. | |
| 2009/0148931 | A1 | 6/2009 | Wilkerson et al. | |
| 2012/0070889 | A1 | 3/2012 | Bayless | |
| 2012/0149091 | A1 | 6/2012 | Wilkerson et al. | |

FOREIGN PATENT DOCUMENTS

| | | | |
|---|---|---|---|
| WO | 03093406 | A2 | 11/2003 |
| WO | 2012118799 | A2 | 9/2012 |
| WO | 2020227648 | A1 | 11/2020 |

OTHER PUBLICATIONS

Schilmiller, Anthony L., Robert L. Last, and Eran Pichersky. "Harnessing plant trichome biochemistry for the production of useful compounds." The Plant Journal 54, No. 4 (2008): 702-711.
Wei, Xing, Jeremy W. Mares, Yandong Gao, Deyu Li, and Sharon M. Weiss. "Biomolecule kinetics measurements in flow cell integrated porous silicon waveguides." Biomedical Optics Express 3, No. 9 (2012): 1993-2003.
Livingston, Samuel J., Teagen D. Quilichini, Judith K. Booth, Darren CJ Wong, Kim H. Rensing, Jessica Laflamme-Yonkman, Simone D. Castellarin, Joerg Bohlmann, Jonathan E. Page, and A. Lacey Samuels. "Cannabis glandular trichomes alter morphology and metabolite content during flower maturation." The Plant Journal 101, No. 1 (2020): 37-56.
Hazekamp, Arno, Anja Peltenburg, Rob Verpoorte, and Christian Giroud. "Chromatographic and spectroscopic data of cannabinoids from *Cannabis sativa* L." Journal of liquid chromatography & related technologies 28, No. 15 (2005): 2361-2382.
Suraweera, Dilnee D., Tim Groom, Paul WJ Taylor, Chinthaka S. Jayasinghe, and Marc E. Nicolas. "Dynamics of flower, achene and trichome development governs the accumulation of pyrethrins in pyrethrum (Tanacetum cinerariifolium) under irrigated and dryland conditions." Industrial Crops and Products 109 (2017): 123-133.
Garbacik, Erik T., Roza P. Korai, Eric H. Frater, Jeroen P. Korterik, Cees Otto, and Herman L. Offerhaus. "In planta imaging of Δ9-tetrahydrocannabinolic acid in *Cannabis sativa* L. with hyperspectral coherent anti-Stokes Raman scattering microscopy." Journal of biomedical optics 18, No. 4 (2013): 046009.
Beavers, Kelsey R., Jeremy W. Mares, Caleb M. Swartz, Yiliang Zhao, Sharon M. Weiss, and Craig L. Duvall. "In situ synthesis of peptide nucleic acids in porous silicon for drug delivery and biosensing." Bioconjugate chemistry 25, No. 7 (2014): 1192-1197.
Zuzarte, Mónica R., Augusto M. Dinis, Carlos Cavaleiro, Lígia R. Salgueiro, and Jorge M. Canhoto. "Trichomes, essential oils and in vitro propagation of Lavandula pedunculata (Lamiaceae)." Industrial Crops and Products 32, No. 3 (2010): 580-587.
Jeon, Jessie S., Simone Bersini, Mara Gilardi, Gabriele Dubini, Joseph L. Charest, Matteo Moretti, and Roger D. Kamm. "Human 3D vascularized organotypic microfluidic assays to study breast cancer cell extravasation." Proceedings of the National Academy of Sciences 112, No. 1 (2015): 214-219.
OrganoPlate, pulled from website https://www.mimetas.com/en/organoplate-sup-sup-product-overview/, Feb. 14, 2022, 2 pages.
Farag, Sayed. "Cannabinoids production in *Cannabis sativa* L.: An in vitro approach." PhD diss., 2014. (split into two PDFs).
Shin, Yoojin, Sewoon Han, Jessie S. Jeon, Kyoko Yamamoto, Ioannis K. Zervantonakis, Ryo Sudo, Roger D. Kamm, and Seok Chung. "Microfluidic assay for simultaneous culture of multiple cell types on surfaces or within hydrogels." Nature protocols 7, No. 7 (2012): 1247-1259.
Adriani, Giulia, Dongliang Ma, Andrea Pavesi, Roger D. Kamm, and Eyleen LK Goh. "A 3D neurovascular microfluidic model consisting of neurons, astrocytes and cerebral endothelial cells as a blood-brain barrier." Lab on a Chip 17, No. 3 (2017): 448-459.
Bioharvest Sciences, pulled from website https://bioharvest.com, Feb. 14, 2022, 3 pages.
Campisi, Marco, Yoojin Shin, Tatsuya Osaki, Cynthia Hajal, Valeria Chiono, and Roger D. Kamm. "3D self-organized microvascular model of the human blood-brain barrier with endothelial cells, pericytes and astrocytes." Biomaterials 180 (2018): 117-129.
Campisi, Marco, Yoojin Shin, Tatsuya Osaki, Cynthia Hajal, Valeria Chiono, and Roger D. Kamm. "3D self-organized microvascular model of the human blood-brain barrier with endothelial cells, pericytes and astrocytes." Biomaterials 180 (2018)—(Supplementary Figures; 19 pages.).
Flores-Sanchez, Isvett Josefina, Jaroslav Peč, Junni Fei, Young Hae Choi, Jaroslav Dušek, and Robert Verpoorte. "Elicitation studies in cell suspension cultures of *Cannabis sativa* L." Journal of biotechnology 143, No. 2 (2009): 157-168.
Hovell, Candice, Jeremy Mares, "InViTri, in vitro trichomes, Grow cells not plants." Imec, Dec. 15, 2021, 17 slides.
PCT International Search Report and Written Opinion, Application No. PCT/US2023/066252, mailed Sep. 15, 2023, 11 pages.
PCT International Search Report and Written Opinion, Application No. PCT/IB2022/000093, mailed Jul. 13, 2022, 19 pages.
Takeda, Hiroyuki, Fuyu Ito, Shigeru Yamanaka, Naoyuki Takiyama, and Katsumi Yoshino. "Roles of trichomes with silica particles on the surface of leaves in Aphananthe aspera." AIP Advances 3, No. 3 (2013): 032120.

* cited by examiner

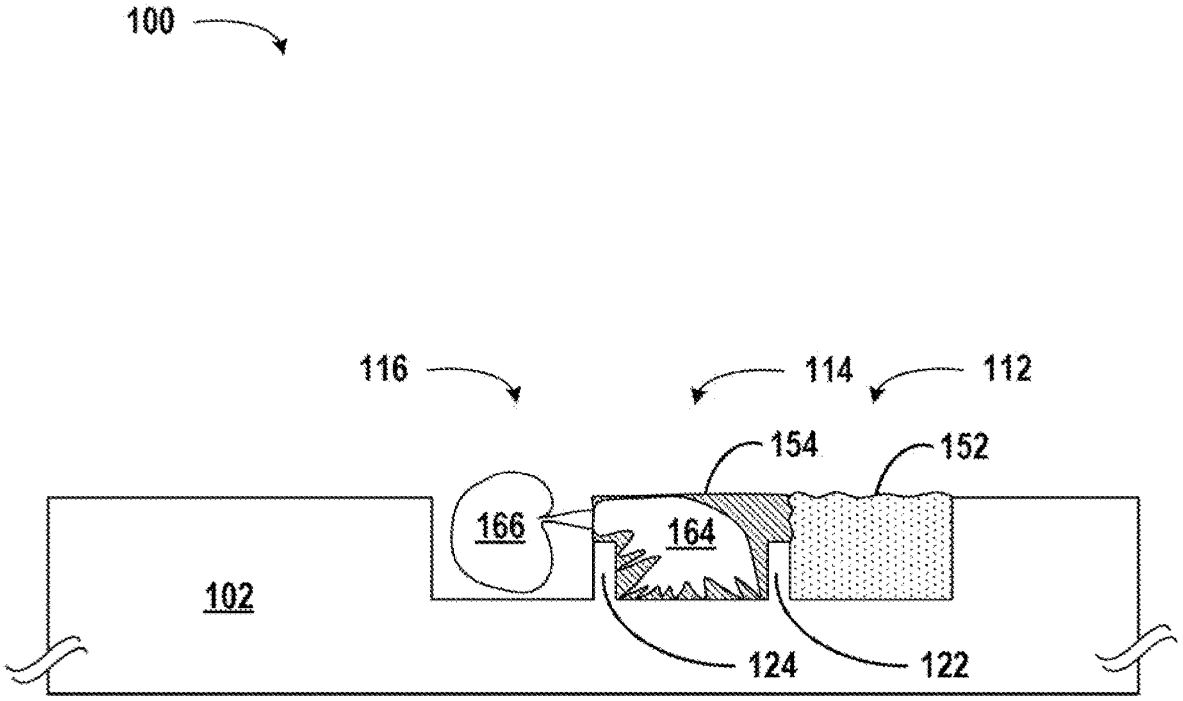
FIG. 1D
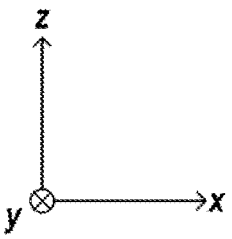

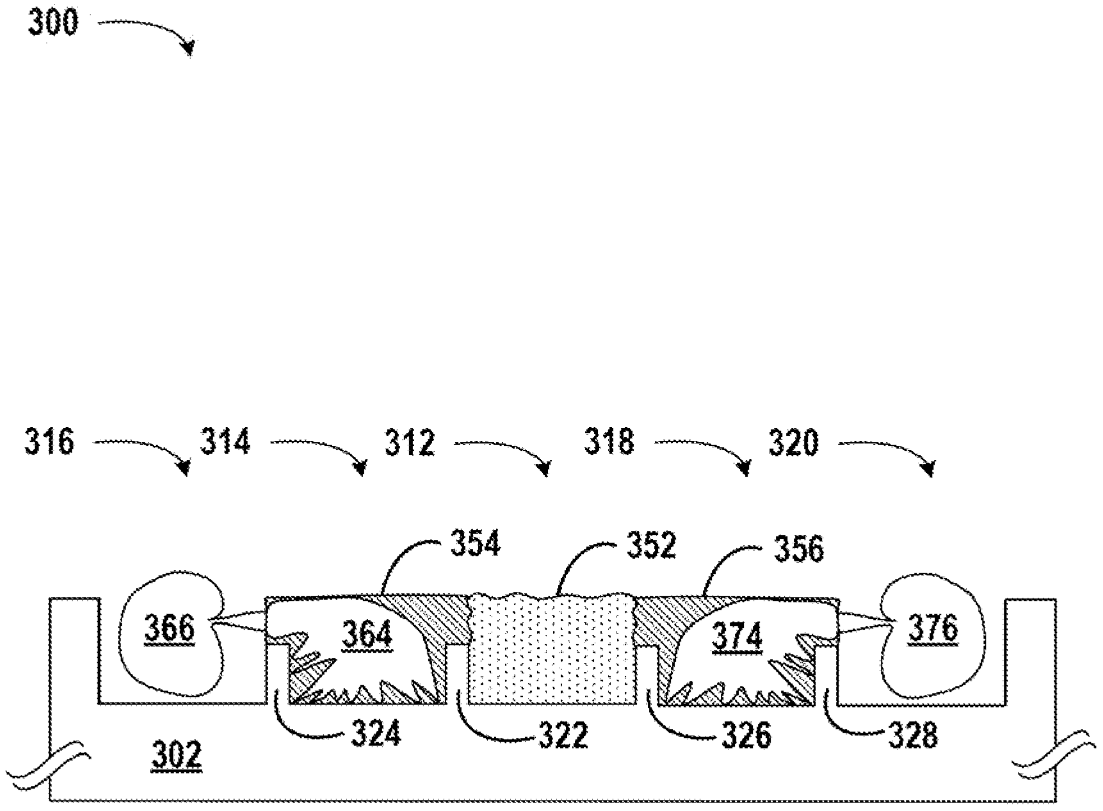
FIG. 3C
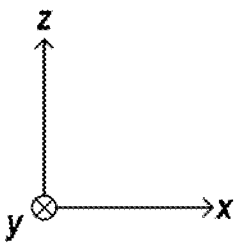

BIOREACTORS AND BIOREACTOR FACILITIES THAT INCLUDE A PLURALITY OF BIOREACTOR TILES

CROSS-REFERENCE TO RELATED APPLICATIONS

U.S. Patent Application No. 63/157,654, filed Mar. 6, 2021, and U.S. patent application Ser. No. 17/653,070, filed Mar. 1, 2022, are hereby incorporated by reference in their entireties.

BACKGROUND

Unless otherwise indicated herein, the materials described in this section are not prior art to the claims in this application and are not admitted to be prior art by inclusion in this section.

Currently, whole *Cannabis sativa* plants are grown, harvested, trimmed, dried, and processed via extraction to obtain useful compounds that are produced and stored in glandular trichomes. This process requires significant infrastructure, equipment, labor, and resources spread across multiple facilities. Further, this process may be susceptible to adverse effects from environmental conditions (e.g., changes in weather or contamination from heavy metals, pests, pesticides, fungal toxins, etc.).

Bioreactors are used in many contexts to grow or culture organisms (e.g., bacteria, plants, etc.). Such organisms may ultimately produce products that are harvested and used in various applications (e.g., pharmaceuticals, food production, etc.). Bioreactors may include light emitters, heaters, fluidic channels, etc. that support the environmental conditions necessary to sustain such organisms. For example, the pH, nutrient supply/concentration, temperature, etc. may all be monitored/adjusted within a bioreactor in order to mimic environmental conditions present in an organism's natural environment. Sample types of bioreactors include continuous stirred tank bioreactors, bubble column bioreactors, airlift bioreactors, fluidized bed bioreactors, packed bed bioreactors, and photo-bioreactors. Each of the various types may be associated with providing different environmental conditions and/or may be designed to support different types of organisms.

SUMMARY

The specification and drawings disclose embodiments that relate to bioreactors and bioreactor facilities that include a plurality of bioreactor tiles.

In a first aspect, the disclosure describes a system. The system includes a first bioreactor. The first bioreactor includes a first housing. The first bioreactor also includes a plurality of first bioreactor tiles positioned within the first housing. Each of the first bioreactor tiles is configured to house cells capable of producing one or more chemical products. Additionally, the first bioreactor includes a first fluid management system. The first fluid management system is configured to provide liquid nutrient media to the first bioreactor tiles to support growth of the cells. The first fluid management system is also configured to harvest the one or more chemical products from the first bioreactor tiles. Further, the first bioreactor includes a first illumination system configured to supply the first bioreactor tiles with illumination light used to support growth of the cells. In addition, the first bioreactor includes a first environmental control system positioned within the first housing and configured to provide the first bioreactor tiles with one or more sets of environmental conditions that support growth of the cells. Still further, the first bioreactor includes one or more first sensors positioned within the first housing and configured to sense one or more conditions associated with the first fluid management system, the first illumination system, the first environmental control system, the first bioreactor tiles, or the cells. Even further, the first bioreactor includes a first controller. The first controller is configured to receive data regarding the one or more conditions from the one or more first sensors. The first controller is also configured to provide, based on the received data, one or more operating parameters to the first fluid management system, the first illumination system, or the first environmental control system.

In a second aspect, the disclosure describes a method. The method includes providing, by a first fluid management system of a first bioreactor, liquid nutrient media to a plurality of first bioreactor tiles of the first bioreactor to support growth of cells housed within the first bioreactor tiles. The first bioreactor tiles are positioned within a first housing of the first bioreactor. The cells are capable of producing one or more chemical products. The method also includes supplying, by a first illumination system of the first bioreactor, illumination light to the first bioreactor tiles to support growth of the cells. In addition, the method includes providing, by a first environmental control system of the first bioreactor, the first bioreactor tiles with one or more sets of environmental conditions that support growth of the cells. The first environmental control system is positioned within the first housing. Further, the method includes sensing, by one or more first sensors of the first bioreactor, one or more conditions associated with the first fluid management system, the first illumination system, the first environmental control system, the first bioreactor tiles, or the cells. The one or more first sensors are positioned within the first housing. Additionally, the method includes receiving, by a first controller of the first bioreactor from the one or more first sensors of the first bioreactor, data regarding the one or more conditions. Still further, the method includes providing, by the first controller based on the received data, one or more operating parameters to the first fluid management system, the first illumination system, or the first environmental control system. Even further, the method includes harvesting, by the first fluid management system, the one or more chemical products from the first bioreactor tiles.

In a third aspect, the disclosure describes a method. The method includes receiving, by a facility-management server from a plurality of controllers of a plurality of respective bioreactors within a facility, data regarding one or more conditions of the respective bioreactors. The method also includes providing, by the facility-management server, one or more operating parameters to at least one of the plurality of controllers based on the received data. Each of the respective bioreactors includes a housing. Each of the respective bioreactors also includes a plurality of bioreactor tiles positioned within the housing. Each of the bioreactor tiles is configured to house cells capable of producing one or more chemical products. In addition, each of the respective bioreactors includes a fluid management system. The fluid management system is configured to provide liquid nutrient media to the bioreactor tiles to support growth of the cells. The fluid management system is also configured to harvest the one or more chemical products from the bioreactor tiles. Further, each of the respective bioreactors includes an illumination system configured to supply the bioreactor tiles with illumination light used to support growth of the cells.

Additionally, each of the respective bioreactors includes an environmental control system positioned within the housing and configured to provide the bioreactor tiles with one or more sets of environmental conditions that support growth of the cells. Yet further, each of the respective bioreactors includes one or more sensors positioned within the housing and configured to sense one or more conditions associated with the fluid management system, the illumination system, the environmental control system, the bioreactor tiles, or the cells. Even further, each of the respective bioreactors includes a controller. The controller is configured to receive data regarding the one or more conditions from the one or more sensors. The controller is also configured to provide the received data to the facility-management server. In addition, the controller is configured to receive one or more operating parameters from the facility-management server. Further, the controller is configured to provide, based on the received data or the one or more received operating parameters from the facility-management server, one or more operating parameters to the fluid management system, the illumination system, or the environmental control system.

In a fourth aspect, the disclosure describes a system. The system includes a first bioreactor. The first bioreactor includes a first housing. The first bioreactor also includes a plurality of first bioreactor tiles positioned within the first housing. Each of the first bioreactor tiles is configured to house cells capable of producing one or more chemical products. Additionally, the first bioreactor includes a first fluid management system. The first fluid management system is configured to provide liquid nutrient media to the first bioreactor tiles to support growth of the cells or production, by the cells, of the one or more chemical products. The first fluid management system is also configured to supply an air mixture to the first bioreactor tiles to support growth of the cells or production, by the cells, of the one or more chemical products. Additionally, the first fluid management system is configured to harvest the one or more chemical products from the first bioreactor tiles. Further, the first bioreactor includes a first illumination system configured to supply the first bioreactor tiles with illumination light used to support growth of the cells or production, by the cells, of the one or more chemical products. In addition, the first bioreactor includes a first environmental control system positioned within the first housing and configured to provide the first bioreactor tiles with one or more sets of environmental conditions that support growth of the cells or production, by the cells, of the one or more chemical products. Yet further, the first bioreactor includes one or more first sensors positioned within the first housing and configured to sense one or more conditions associated with the first fluid management system, the first illumination system, the first environmental control system, the first bioreactor tiles, or the cells. Even further, the first bioreactor includes a first controller. The first controller is configured to receive data regarding the one or more conditions from the one or more first sensors. The first controller is also configured to provide, based on the received data, one or more operating parameters to the first fluid management system, the first illumination system, or the first environmental control system. Each of the first bioreactor tiles includes a substrate having a first channel, a second channel, and a third channel defined therein. The first channel is separated from the second channel by a first partial wall structure. The second channel is separated from the third channel by a second partial wall structure. The first channel is configured to receive the liquid nutrient media from the first fluid management system. The second channel is configured to house the cells capable of producing the one or more chemical products. The third channel is configured to house the one or more chemical products produced by the cells or the air mixture that supports growth of the cells or production, by the cells, of the one or more chemical products. Each of the first bioreactor tiles also includes an optical waveguide. The optical waveguide is configured to receive the illumination light from the first illumination system at a first end of the optical waveguide. The optical waveguide is also configured to propagate the illumination light toward a second end of the optical waveguide. Further, the optical waveguide is configured to allow at least a portion of the illumination light to escape the optical waveguide from a first surface of the optical waveguide as the illumination light propagates toward the second end of the optical waveguide. In addition, the optical waveguide is configured to provide the portion of the illumination light that escapes the optical waveguide from the first surface to the second channel or the third channel to support growth of the cells or production, by the cells, of the one or more chemical products.

In a fifth aspect, the disclosure describes a method. The method includes providing, by a first fluid management system of a first bioreactor, liquid nutrient media to a plurality of first bioreactor tiles of the first bioreactor to support growth of cells housed within the first bioreactor tiles or production, by the cells housed within the first bioreactor tiles, one or more chemical products. The first bioreactor tiles are positioned within a first housing of the first bioreactor. The method also includes supplying, by the first fluid management system, an air mixture to the first bioreactor tiles to support growth of the cells or production, by the cells, of the one or more chemical products. In addition, the method includes supplying, by a first illumination system of the first bioreactor, illumination light to the first bioreactor tiles to support growth of the cells or production, by the cells, of the one or more chemical products. Further, the method includes providing, by a first environmental control system of the first bioreactor, the first bioreactor tiles with one or more sets of environmental conditions that support growth of the cells or production, by the cells, of the one or more chemical products, wherein the first environmental control system is positioned within the first housing. Additionally, the method includes sensing, by one or more first sensors of the first bioreactor, one or more conditions associated with the first fluid management system, the first illumination system, the first environmental control system, the first bioreactor tiles, or the cells. The one or more first sensors are positioned within the first housing. Still further, the method includes receiving, by a first controller of the first bioreactor from the one or more first sensors of the first bioreactor, data regarding the one or more conditions. Even further, the method includes providing, by the first controller based on the received data, one or more operating parameters to the first fluid management system, the first illumination system, or the first environmental control system. Yet further, the method includes harvesting, by the first fluid management system, the one or more chemical products from the first bioreactor tiles. Each of the first bioreactor tiles includes a substrate having a first channel, a second channel, and a third channel defined therein. The first channel is separated from the second channel by a first partial wall structure. The second channel is separated from the third channel by a second partial wall structure. The first channel is configured to receive the liquid nutrient media from the first fluid management system. The second channel is configured to house the cells capable of producing the one or more chemical products. The third channel is configured to house the one or more chemical products produced by the cells or the air mixture that supports growth of the cells or production, by the cells, of the one or more chemical products. Each of the first bioreactor tiles also includes an optical waveguide. The optical waveguide is configured to receive the illumination light from the first illumination system at a first end of the optical waveguide. The optical waveguide is also configured to propagate the illumination light toward a second end of the optical waveguide. Additionally, the optical waveguide is configured to allow at least a portion of the illumination light to escape the optical waveguide from a first surface of the optical waveguide as the illumination light propagates toward the second end of the optical waveguide. Further, the optical waveguide is configured to provide the portion of the illumination light that escapes the optical waveguide from the first surface to the second channel or the third channel to support growth of the cells or production, by the cells, of the one or more chemical products.

In a sixth aspect, the disclosure describes a method. The method includes receiving, by a facility-management server from a plurality of controllers of a plurality of respective bioreactors within a facility, data regarding one or more conditions of the respective bioreactors. The method also includes providing, by the facility-management server, one or more operating parameters to at least one of the plurality of controllers based on the received data. Each of the respective bioreactors includes a housing. Each of the respective bioreactors also includes a plurality of bioreactor tiles positioned within the housing, wherein each of the bioreactor tiles is configured to house cells capable of producing one or more chemical products. In addition, each of the respective bioreactors includes a fluid management system. The fluid management system is configured to provide liquid nutrient media to the bioreactor tiles to support growth of the cells or production, by the cells, of the one or more chemical products. The fluid management system is also configured to supply an air mixture to the bioreactor tiles to support growth of the cells or production, by the cells, of the one or more chemical products. Additionally, the fluid management system is configured to harvest the one or more chemical products from the bioreactor tiles. Further, each of the respective bioreactors includes an illumination system configured to supply the bioreactor tiles with illumination light used to support growth of the cells or production, by the cells, of the one or more chemical products. Additionally, each of the respective bioreactors includes an environmental control system positioned within the housing and configured to provide the bioreactor tiles with one or more sets of environmental conditions that support growth of the cells or production, by the cells, of the one or more chemical products. Still further, each of the respective bioreactors includes one or more sensors positioned within the housing and configured to sense one or more conditions associated with the fluid management system, the illumination system, the environmental control system, the bioreactor tiles, or the cells. Even further, each of the respective bioreactors includes a controller. The controller is configured to receive data regarding the one or more conditions from the one or more sensors. The controller is also configured to provide the received data to the facility-management server. Additionally, the controller is configured to receive one or more operating parameters from the facility-management server. Further, the controller is configured to provide, based on the received data or the one or more received operating parameters from the facility-management server, one or more operating parameters to the fluid management system, the illumination system, or the environmental control system. Each of the bioreactor tiles includes a substrate having a first channel, a second channel, and a third channel defined therein. The first channel is separated from the second channel by a first partial wall structure. The second channel is separated from the third channel by a second partial wall structure. The first channel is configured to receive the liquid nutrient media from the fluid management system. The second channel is configured to house the cells capable of producing the one or more chemical products. The third channel is configured to house the one or more chemical products produced by the cells or the air mixture that supports growth of the cells or production, by the cells, of the one or more chemical products. Each of the bioreactor tiles also includes an optical waveguide. The optical waveguide is configured to receive the illumination light from the illumination system at a first end of the optical waveguide. The optical waveguide is also configured to propagate the illumination light toward a second end of the optical waveguide. Additionally, the optical waveguide is configured to allow at least a portion of the illumination light to escape the optical waveguide from a first surface of the optical waveguide as the illumination light propagates toward the second end of the optical waveguide. Further, the optical waveguide is configured to provide the portion of the illumination light that escapes the optical waveguide from the first surface to the second channel or the third channel to support growth of the cells or production, by the cells, of the one or more chemical products.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 1D is a front-view illustration of a bioreactor tile, according to example embodiments.

FIG. 3C is a front-view illustration of a bioreactor tile, according to example embodiments.

DETAILED DESCRIPTION

Figure 1A:
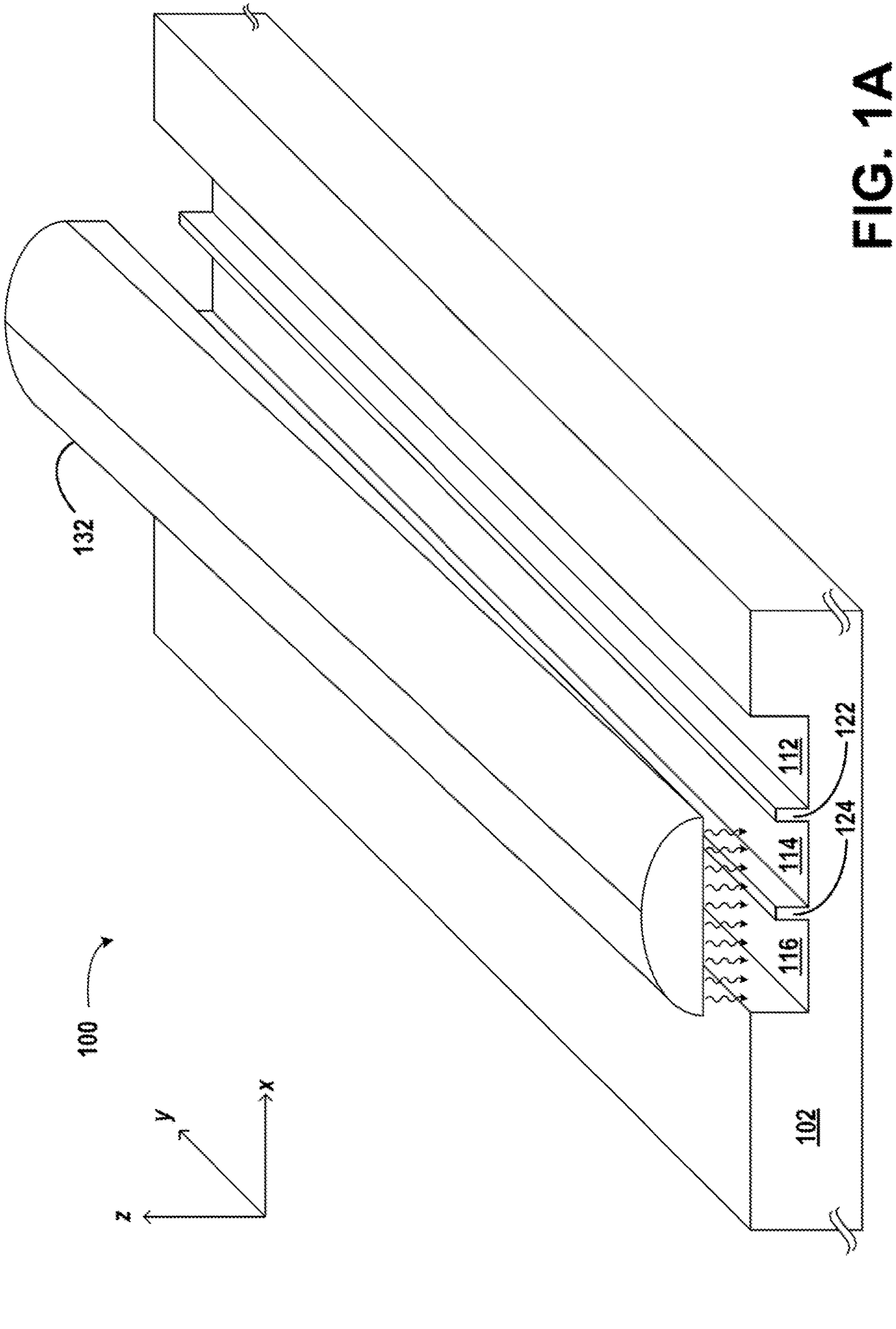
FIG. 1A is an isometric illustration of a bioreactor tile, according to example embodiments.

Example methods and systems are described herein. Any example embodiment or feature described herein is not necessarily to be construed as preferred or advantageous over other embodiments or features. The example embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the figures should not be viewed as limiting. It should be understood that other embodiments might include more or less of each element shown in a given figure. In addition, some of the illustrated elements may be combined or omitted. Similarly, an example embodiment may include elements that are not illustrated in the figures.

Throughout this disclosure, the term "system" is used to describe various embodiments. It is understood that this term is to be broadly construed. A "system" may include a bioreactor tile, a plurality of bioreactor tiles, a bioreactor (e.g., that includes one or more bioreactor tiles), a plurality of bioreactors (e.g., each including one or more bioreactor tiles) within a single facility or across multiple facilities, a single bioreactor facility (e.g., that includes one or more bioreactors), a plurality of bioreactor facilities, etc.

Further, the terms "controller" and "computing device" are both used throughout. It is understood that, in many cases, these terms overlap and/or are used to describe similar or identical components. Unless context dictates otherwise, a controller is a device that is used to control one or more components (e.g., one or more bioreactors or one or more bioreactor facilities). Such controllers may include one or more computing devices (e.g., which themselves may include one or more memories and/or processors). While computing devices can be used as and/or part of controllers, they need not be in all cases. Computing devices represent a broad genus of devices that perform computations, intake data, output data, store data, and/or communicate with other devices. Hence, it is understood that, while in many cases a controller might only include a computing device and, therefore, the controller/computing device perform the same functions, this is not necessarily the case. In other words, controllers may have components in addition to or instead of a computing device and computing devices may not always be used as controllers.

I. OVERVIEW

Example embodiments relate to bioreactor tiles that include fluidic channels (e.g., microfluidic channels or non-microfluidic channels having a larger scale) and one or more optical waveguides. Such bioreactor tiles may be used to grow one or more types of cells. For example, the bioreactor tiles may support growth of plant cells (e.g., parenchymal plant cells) that produce one or more products (e.g., trichomes that contain desirable compounds). In some embodiments, for instance, example embodiments may be used to grow *Cannabis sativa* parenchymal cells that produce trichomes (e.g., glandular trichomes). Such trichomes may contain one or more organic compounds (e.g., cannabidiol), which can be harvested from the bioreactor tiles and used in a variety of applications. Using techniques described herein, the production of cannabidiol from *Cannabis sativa* parenchymal cells and trichomes can be performed in a way that results in: reduced exposure to outdoor environmental conditions; elimination of product contamination from heavy metals, pests, pesticides, fungal toxins, or products used in whole plant cultivation; a reduction in the total volume of solvents needed for product preparation; a simplification in the extraction process; a reduction in time, resources, and infrastructure required; an increased product purity; increased product properties (e.g., potency); and/or decreased carbon footprint for product isolation.

In some embodiments, the bioreactor tiles may include a series of channels (e.g., microfluidic channels defined within a substrate). For example, one channel may house the plant cells (e.g., within a gel). Another channel, parallel and adjacent to the channel housing the plant cells, may supply the plant cells with nutrients (e.g., in the form of liquid nutrient media). The nutrient channel may be supplied with nutrients using one or more pumps and/or based on a nutrient mixture provided from one or more tanks. For example, the nutrient channel may include one or more inlets and one or more outlets used to pass liquid nutrient media into and out of the nutrient channel. The type and concentration of nutrients supplied via this channel may depend on the type of plant cells housed within the plant cell channel. The plant cell channel and the nutrient media channel may be separated from one another by a partial wall structure. The partial wall structure may be of sufficient height so as to maintain separation between the components of the adjacent channels due to surface tension (i.e., the plant cells may stay in the plant cell channel based on surface tension above the partial wall structure and the liquid nutrient media may stay in the nutrient channel based on surface tension above the partial wall structure). However, in addition to having a sufficient height so as to maintain channel separation, the partial wall structure may nonetheless still allow the plant cells within the plant cell channel to retrieve the nutrients from the nutrient channel.

Additionally, the bioreactor tiles may include a product channel (e.g., a trichome channel). The product channel may be positioned parallel and adjacent to the plant cell channel on an opposite side of the plant cell channel from the nutrient channel. The product channel and the plant channel may also be separated by a partial wall structure that maintains component separation between the adjacent channels using surface tension (e.g., as viscous forces dominate over convective forces based on the size of the channels), but still allows interaction between the adjacent channels. Further, the product channel may include one or more inlets and one or more outlets (e.g., used to pass air and/or extractant into and out of the product channel). Once the plant cells within the plant cell channel have matured to a sufficient state, the plant cells may begin to produce one or more products (e.g., one or more chemical products). For example, in the case of *Cannabis sativa* cells, once the *Cannabis sativa* cells have sufficiently matured they will begin to produce trichomes (i.e., appendage structures that grow from the plant cells). The trichomes may grow out of the plant channel and extend into the product channel. Further, the trichomes may contain cannabidiol (e.g., cannabidiol oil), which is a widely used pharmaceutical substance.

Upon the plant cells beginning to produce trichomes, the bioreactor tile may provide an environment that further encourages trichome growth. In some embodiments, this may include providing the same environmental conditions that were provided by the bioreactor tile during the plant cell growth stage. However, in some embodiments, upon the initiation of the trichome phase, the environmental conditions supplied by the bioreactor tile may change (e.g., the type and/or concentration of the nutrients in the liquid nutrient media might change, the lighting conditions supplied to the trichomes/the plant cells may change, the temperature and/or pH may change, etc.). Once the trichomes are mature (e.g., when the concentration of monoterpenes is substantially higher than the concentration of sesquiterpenes within the trichomes), the trichomes and/or the products within the trichomes (e.g., cannabidiol) may be harvested. Harvesting the trichomes may involve flushing the product channel with extractant (e.g., low-temperature extractant) to shear trichome heads from the trichome bodies and/or to shear the trichomes from the underlying plant cells and then collecting the extractant/trichome mixture.

In some embodiments, there may also be an air inlet/outlet to supply the plant cells within the plant cell channel and/or the trichomes within the trichome channel with sufficient air (e.g., for photosynthesis, respiration, and/or to provide mechanical shear to the trichomes). Such an airflow may occur within one or more of the channels. For example, the air may be provided via the trichome channel. Prior to and during trichome growth, because the trichome channel is adjacent to and partially connected to the plant cell channel, the trichomes in the trichome channel and the plant cells in the plant cell channel can exchange gases with air flowing through the trichome channel. Such airflow may be generated by one or more pumps and/or based on an air mixture provided from one or more tanks. Additionally or alternatively, airflows may also be established within the plant cell channel or the nutrient channel.

In addition to nutrients and airflow, the plant cells (e.g., as well as trichomes) may use light to grow (e.g., to perform photosynthesis). This light may be supplied using one or more optical waveguides (i.e., light pipes) of the bioreactor tile. The optical waveguide(s) may run parallel to the longitudinal direction of the plant cell channel and/or the product channel. Additionally, the optical waveguide(s) may be positioned above the plant cell channel and/or the product channel. In such embodiments, the optical waveguide(s) may receive illumination light (e.g., emitted by a light-emitter diode (LED) or other light emitter) at a first end and then provide the illumination light to the plant cells (e.g., within the plant cell channel) and/or the trichomes (e.g., within the product channel) via a bottom surface of the optical waveguide. In some embodiments, the optical waveguide may be tapered (e.g., along a vertical direction) and/or may include one or more surface features (e.g., diffractive features, longitudinal striations, lateral striations, isotropic striations, pits, etc.) that permit the illumination light to escape the optical waveguide along the bottom surface of the optical waveguide as the illumination light propagates from the first end of the optical waveguide toward a second end of the optical waveguide.

Alternatively, in some embodiments, the optical waveguide(s) may be positioned on a surface of the substrate that is adjacent to the product channel. For example, the optical waveguide(s) may be surface-integrated optical waveguide(s)(e.g., fabricated on the surface of the substrate using microfabrication techniques). In such embodiments, the optical waveguide(s) may receive illumination light (e.g., emitted by a LED or other light emitter) at a first end and then provide the illumination light to the plant cells (e.g., within the plant cell channel) and/or the trichomes (e.g., within the product channel) from a side surface of the optical waveguide. As with the suspended/cantilevered optical waveguide positioning described above, such surface-integrated optical waveguides may be tapered (e.g., along a vertical direction) and/or may include one or more surface features that permit the illumination light to escape the optical waveguide along the side surface of the optical waveguide as the illumination light propagates from the first end of the optical waveguide toward a second end of the optical waveguide.

Regardless of the position(s) of the optical waveguide(s) relative to the product channel or the plant cell channel, the optical waveguide(s) may be configured to distribute the illumination light in various intensities along the lengths of the plant cell channel and/or the product channel. For example, in some embodiments, the optical waveguide may provide the illumination light to the product channel and/or the plant cell channel in a substantially uniform intensity along the length of the respective channel (e.g., +/−0.1% variation along the length of the respective channel, +/−1.0% variation along the length of the respective channel, +/−5.0% variation along the length of the respective channel, +/−10.0% variation along the length of the respective channel, or +/−15% variation along the length of the respective channel). In other embodiments, though, the optical waveguide may provide the illumination light in a manner that is intentionally varied along the length of the respective channel.

While a three-channel arrangement (e.g., an arrangement having a single nutrient channel, a single plant cell channel, and a single product channel, which may be referred to herein as a "single-sided arrangement") has been described above, it is understood that other arrangements are also possible and are contemplated herein. For example, in some embodiments, a single nutrient channel may supply liquid nutrient media to two plant cell channel/product channel pairs. In such embodiments, the nutrient channel may be flanked, on both sides, by plant cell channels (e.g., each of the plant cell channels separated from the nutrient channel by a partial wall structure). Further, each of the two plant cell channels may be flanked (on a side of the plant cell channel opposite from the side of the plant cell channel that is adjacent to the nutrient channel) by a respective product channel. This alternate arrangement may be referred to herein as a "double-sided arrangement." It is understood that numerous other arrangements are also possible (e.g., four-channel arrangements, five-channel arrangements, six-channel arrangements, seven-channel arrangements, eight-channel arrangements, nine-channel arrangements, ten-channel arrangements, etc.). For example, some embodiments may include a seven-channel arrangement (e.g., a double-sided, seven-channel arrangement having an air channel, flanked on both sides by channels configured to house suspensions of plant cells, each of those channels being flanked on outer sides by gel nutrient media channels, each of those channels being flanked on outer sides by liquid nutrient media channels).

Further, while a bioreactor tile with only one single-sided arrangement of channels defined within the substrate is described above, it is understood that many sets of channels may be defined within the same substrate. For example, a plurality of single-sided arrangements of channels may be defined adjacently to one another within the substrate. Likewise, a plurality of double-sided arrangements of channels may be defined adjacently to one another within the substrate. In still other embodiments, a mixture of single-sided channel arrangements and double-sided channel arrangements may all be defined within a single substrate. Such arrangements having a plurality of sets of channels may provide for higher throughput (e.g., a larger production of product, such as cannabidiol oil, per unit time or per unit area).

Additionally, while a bioreactor tile having only a single substrate with channels defined therein (referred to herein as a "single-layer arrangement") was described above, it is understood that other arrangements are also possible. For example, a "multi-layer arrangement" having multiple substrates all stacked on top of one another and each with one or more sets of channels defined therein is also contemplated herein. In such a multi-layer arrangement, there may be respective optical waveguides for each layer that only supply light to the channels in their respective layer. Alternatively, there may only be a single set of optical waveguides that supply light to all the channels in all of the layers. For example, the arrangements of channels defined in each of the substrates of each of the layers may be aligned vertically with one another. Then, positioned above these vertically aligned arrangements, a single optical waveguide could provide light to all the channels in the vertically aligned arrangements. Such embodiments may be used when the substrates and/or the contents of the channels (e.g., the liquid nutrient media, the plant cells in a gel matrix, etc.) are substantially transparent and/or translucent. Such multi-layer arrangements may provide for higher throughput (e.g., a larger production of product, such as cannabidiol oil, per unit time or per unit volume).

The bioreactor tiles described above may be designed to readily scale with desired production output. In some embodiments, a plurality of bioreactor tiles (e.g., two bioreactor tiles, three bioreactor tiles, four bioreactor tiles, five bioreactor tiles, ten bioreactor tiles, twenty bioreactor tiles, thirty bioreactor tiles, forty bioreactor tiles, fifty bioreactor tiles, one hundred bioreactor tiles, two hundred bioreactor tiles, three hundred bioreactor tiles, four hundred bioreactor tiles, five hundred bioreactor tiles, one thousand bioreactor tiles, etc.) may be slotted into a single bioreactor. For example, a bioreactor may include a cabinet or other housing that supports a number of bioreactor tiles. Each of the bioreactor tiles may be slotted into a different shelf of the housing (e.g., arranged horizontally adjacent to one another within the housing or vertically stacked with respect to one another within the housing). As such, the cabinet with the associated bioreactor tiles may be referred to herein as a "multi-tiled bioreactor." The bioreactor may also include additional components used to monitor and support the bioreactor tiles. For example, the bioreactor may include one or more illumination sources (e.g., LEDs or other light emitters) within an illumination system that connects to the optical waveguide(s) of each of the bioreactor tiles in order to provide illumination light to the plant cell channels and/or the product channels via the optical waveguide(s). The illumination sources may be connected to a power supply of the cabinet, for example. Because the illumination sources are components within the housing, rather than within the individual bioreactor tiles, any heat generated by the illumination sources may be produced in a region of the housing that is not so near to the plant cells and/or the trichomes so as to adversely impact the temperature near the plant cells/trichomes.

In addition to one or more illumination systems, a bioreactor may also include one or more fluid management systems. Such fluid management systems may include tanks used to store nutrients, products, cellular precursors, air, gels, etc. for use with the bioreactor tiles; one or more pumps used to transport nutrients, products, cellular precursors, air, gels, etc. to and/or from the bioreactor tiles; and/or one or more tubes/pipes through which nutrients, products, cellular precursors, air, gels, etc. are transported to and/or from the bioreactor tiles. Additionally, the bioreactor may include one or more environmental control systems. Such environmental control systems may include heating devices or cooling devices used to maintain an environmental temperature throughout the housing or in specific locations of the housing. Additionally or alternatively, environmental control systems may include humidifiers.

Further, the housing may include one or more sensors. The sensors may be positioned within the housing and used to sense one or more conditions associated with the bioreactor (e.g., associated with the fluid management system(s), the illumination system(s), the environmental control system(s), the bioreactor tile(s), or the cell(s) within the bioreactor tile(s)). For example, the bioreactor may include one or more sensors used to monitor a temperature inside various regions of the housing, one or more sensors used to monitor a humidity inside various regions of the housing, one or more sensors used to monitor an air pressure inside various regions of the housing, one or more sensors used to monitor concentration of nutrients within the nutrient channel, one or more sensors used to monitor light intensity within various regions of the housing, one or more sensors used to monitor pH in various channels, one or more sensors used to monitor flow rate of air through one or more tubes or channels, or one or more sensors used to sense an amount of nutrient, product, air, etc. within a tank in the housing.

Still further, in order to monitor the state of the plant cells in the plant cell channel and/or the trichomes in the product channel, each individual bioreactor tile or the entire housing may also include a camera or other optical imaging device (e.g., fluorescent microscope or hyperspectral imaging sensor) configured to capture images or other optical data (depending on the imaging modality used) associated with the plant cell channels and/or the trichomes. Based on the captured images or other captured optical data, a computing device (e.g., a bioreactor controller) executing one or more instructions (e.g., stored within a memory, such as a hard disk) may make control determinations for the bioreactor. In other words, the bioreactor controller may be configured to receive data regarding one or more conditions of the bioreactor from one or more sensors of the bioreactor and provide, based on the received data, one or more operating parameters to components of the bioreactor. For example, the computing device may determine when to provide certain nutrient combinations to the nutrient channels of the bioreactor tiles, the temperature at which to maintain certain regions of the housing (e.g., to promote plant cell growth or trichome growth), when to harvest the products, what light intensity/illumination schedule to use to illuminate the plant cell channels or the product channels. As such, the computing device may be connected to one or more sensors of the bioreactor, as well as one or more environmental control systems, one or more power supplies, one or more fluid management systems, one or more illumination systems, etc. of the bioreactor. In some embodiments, the computing device may be configured to communicate with one or more remote computing devices (e.g., over BLUETOOTH®, the public Internet, etc.) to externally provide one or more statuses of the bioreactor (e.g., for remote monitoring/analysis).

Further, a plurality of such multi-tiled bioreactors may be used simultaneously within a system (e.g., within a single production facility or across a plurality of production facilities). For example, a climate-controlled warehouse having a number of bioreactors that each include a plurality of bioreactor tiles may be used to produce large product quantities (e.g., tens or hundreds of kg of crude cannabidiol oil per trichome life-cycle). The production facility may include a central monitoring computing device (i.e., a facility-management server) that monitors data from each of the individual multi-tiled bioreactors to make control decisions across the entire facility. Additionally or alternatively, a remote (i.e., off-site) computing device (e.g., cloud server) may monitor the status of the bioreactors within the production facility (i.e., bioreactor facility).

A facility-management server monitoring data from each of the respective bioreactors may permit a variety of coordination techniques and/or optimization techniques to be performed across the bioreactors. For example, the facility-management server may cause two different production techniques to be performed on two different bioreactors. Such different production techniques may include using different chemical compositions for liquid nutrient media (e.g., as provided to bioreactor tiles of the respective bioreactors by the fluid management systems of the respective bioreactors), different lighting schedules (e.g., as administered to bioreactor tiles of the respective bioreactors by the illumination systems of the respective bioreactors), and/or different environmental conditions (e.g., different temperatures and/or humidities provided by the environmental control systems of the respective bioreactors) to support cell growth (e.g., parenchymal growth and/or trichome growth) and/or product production within the bioreactor tiles of the respective bioreactors. The facility-management server may the receive data from each of the two bioreactors (e.g., via controllers of the respective bioreactors) based on measurements made by sensors of the respective bioreactors. Such data may include data on growth rate, product yield (e.g., cannabidiol concentration within cannabidiol oil produced by trichomes of the respective bioreactors and/or amount of cannabidiol oil produced by trichomes of the respective bioreactors), product yield per unit energy spent (e.g., liters of cannabidiol oil per Joule of energy used to generate the cannabidiol oil), life cycle duration, etc. Based on this data, the facility-management server can select new operating parameters for future production cycles within one or both of the bioreactors. For example, if a first bioreactor universally outperforms a second bioreactor in terms of growth rate and/or product yield, the operating parameters of the second bioreactor could be adjusted in future production cycles such that they match the operating parameters using in the first bioreactor in the previous production cycle. Further, in some embodiments, if certain aspects of the first bioreactor outperformed the second bioreactor, but other aspects of the second bioreactor outperformed the first bioreactor, a hybrid set of operating parameters may be generated/used in future production cycles based on the operating parameters previously used in the first bioreactor and the operating parameters previously used in the second bioreactor.

In addition, to ensure the bioreactor facility is manageable/operates smoothly, the facility-management server may coordinate operation of the respective bioreactors in the facility. For example, the facility-management server may stagger the times at which the various bioreactors in the facility begin their respective production cycles. As such, if certain pain points exist in the production cycle (e.g., certain points in the production cycle at which failure of a given bioreactor has a peak in probability or certain points in which intervention of a mechanic/engineer is needed), the time of occurrence of such pain points may also be staggered. For instance, if a bioreactor needs to be manually cleaned and/or serviced in between each production cycle, the production cycles of various bioreactors may be staggered such that each bioreactor does not need to be manually cleaned/serviced simultaneously.

Further, the facility-management server may provide feedback to the respective bioreactors (e.g., to controllers of the respective bioreactors) when the respective bioreactors encounter trigger conditions. For example, controllers of the bioreactors may be configured to monitor sensor data associated with the one or more sensors of the bioreactors. Upon the sensor data corresponding to one or more trigger conditions (e.g., a threshold temperature, a threshold change in temperature over a predetermined time, a threshold air pressure, a threshold change in air pressure over a predetermined time, a threshold humidity, a threshold change in humidity over a predetermined time, a threshold pH, a threshold change in pH over a predetermined time, a threshold cellular growth condition being met, a threshold product production condition being met, a threshold flow rate, a threshold change in flow rate over a predetermined time, a threshold brightness, a threshold change in brightness over a predetermined time, etc.), the respective controller may raise a flag. Raising a flag may include sending a communication to the facility-management server that a threshold condition has been met and/or changing a variable value within the memory of the controller, where the variable value is accessible by the facility-management server. Once the facility-management server determines that a flag has been raised for a given bioreactor, the facility-management server may determine how to address the flag and provide instructions to the controller of the bioreactor that indicate an appropriate response action to take. For example, if the temperature (e.g., as detected by a temperature sensor in the bioreactor) reaches a value that is too high (e.g., above a threshold temperature) within the bioreactor (e.g., giving rise to a temperature flag being raised by the controller of the bioreactor), the facility-management server may determine that the heating device (e.g., of the environmental control system of the bioreactor) is to be turned off or turned down and/or may determine that a cooling device (e.g., of the environmental control system of the bioreactor) is to be turned on or turned up. Such a determination may then be communicated to the controller of the bioreactor. Other determinations are possible in response to other flags.

Additionally or alternatively, the controller of the bioreactor, itself, may make supplemental and/or additional determinations based on threshold conditions being met. For example, once sufficient product has been produced within the bioreactor tiles of the bioreactor (e.g., as determined based on imaging by one or more imaging sensors within the bioreactor, such as based on a spectral signature of cells captured in a hyperspectral representation), the controller may determine that it is time to progress to a harvest phase of the production cycle. In such a case, the controller may then cause the bioreactor to proceed to a harvest phase. Alternatively, in some embodiments, the controller may then contact the facility-management server to request permission to proceed to a harvest phase.

In addition to a facility-management server that coordinates the activities and/or operating parameters of multiple bioreactors within the facility, a system (e.g., a bioreactor facility) may also include shared devices that can be used to augment the capabilities of the one or more bioreactors within the facility. For example, the facility may include a facility-wide environmental control system (e.g., heating and cooling system). If the facility includes a warehouse, the facility-wide environmental control system may be configured to provide climate control to the exteriors of the bioreactors and/or to an on-site facility-management server. Additionally or alternatively, the facility may include a facility-wide fluid management system. For example, the facility may include a floor surface and a subfloor surface, between which pipes/pumps/tanks/etc. are used to supply different fluids (e.g., air mixtures, liquid nutrient media, extractant, etc.) to the various bioreactors (e.g., to the individual fluid management systems of the various bioreactors) and/or collect/store fluids from the various bioreactors (e.g., products produced by cells in the various bioreactors).

In still other embodiments, the facility may include one or more components that can be attached to one bioreactor, used for a period of time, and then detached from that bioreactor and moved to another bioreactor for use. For example, in order to sterilize a bioreactor before initial use, one or more sterilization procedures may be performed. Such sterilization procedures may include supplying particular wavelengths of light (e.g., ultraviolet wavelengths) to the bioreactor and/or supplying particular gases to the bioreactor (e.g., gases that are toxic to bacteria that might be present within the bioreactor). One or more light sources capable of emitting the particular wavelengths and/or one or more tanks filled with the particular gases may be attached to a given bioreactor to perform the sterilization procedure and then detached and moved to another bioreactor to perform another sterilization procedure.

In some embodiments, each of the bioreactor tiles in a single bioreactor may be used to grow/harvest the same product. Alternatively, in some embodiments, different bioreactor tiles may be used to grow/harvest different products. Likewise, in some embodiments, each of the multi-tiled bioreactors in a single production facility may be used to grow/harvest the same product. Alternatively, in some embodiments, different bioreactors in a single production facility may be used to grow/harvest different products. Additionally, in some embodiments, different bioreactor tiles (e.g., within the same bioreactor or across different bioreactors) may be used as so-called "monitoring tiles," "optimization tiles," or process control monitor (PCM) tiles." Unlike "production tiles" (which have been described above and throughout as being used to grow plant cells, produce trichomes, harvest product, etc.), "monitoring tiles" may be bioreactor tiles that are used purely to monitor the status of various systems in the bioreactors (e.g., the flow rate attributable to the fluid management system, the light output attributable to the illumination system, etc.). As such, "monitoring tiles" may have one or more sensors embedded within the respective tiles to more accurately measure various conditions of the respective monitoring tile.

Further, while *Cannabis* saliva is described throughout as an example plant cell that could be grown to produce trichomes containing cannabidiol using the bioreactor tiles described herein, it is understood that other types of cells and/or other products are also possible (e.g., both plant cells that produce trichomes and those that do not). For example, other plant cells that produce trichomes and could be grown using the techniques described herein include *Artemisia annua* cells, *Chrysanthemum cinerariifolium* cells, *Chrysanthemum coccineum* cells, *Gossypium hirsutum* cells, *Gossypium barbadense* cells, *Gossypium arboreum* cells, *Gossypium herbaceum* cells, *Lavandula angustifolia* cells, *Arabidopsis thaliana* cells, *Mentha* x *piperita* cells, and *Mentha haplocalyx* cells. Such plant cells could produce products that include tetrahydrocannabinol, artemisinin, pyrethrum, camphor, glucosinolate, linalool, linalyl acetate, menthol, or peppermint camphor. Still further, the techniques and devices described herein could be used to grow other types of cells (i.e., non-plant cells) and produce products (e.g., trichome products). For example, algae cells, lichen cells, and protist cells could be grown.

II. EXAMPLE EMBODIMENTS

The following description and accompanying drawings will elucidate features of various example embodiments. The embodiments provided are by way of example, and are not intended to be limiting. As such, the dimensions of the drawings are not necessarily to scale.

Figure 1B:
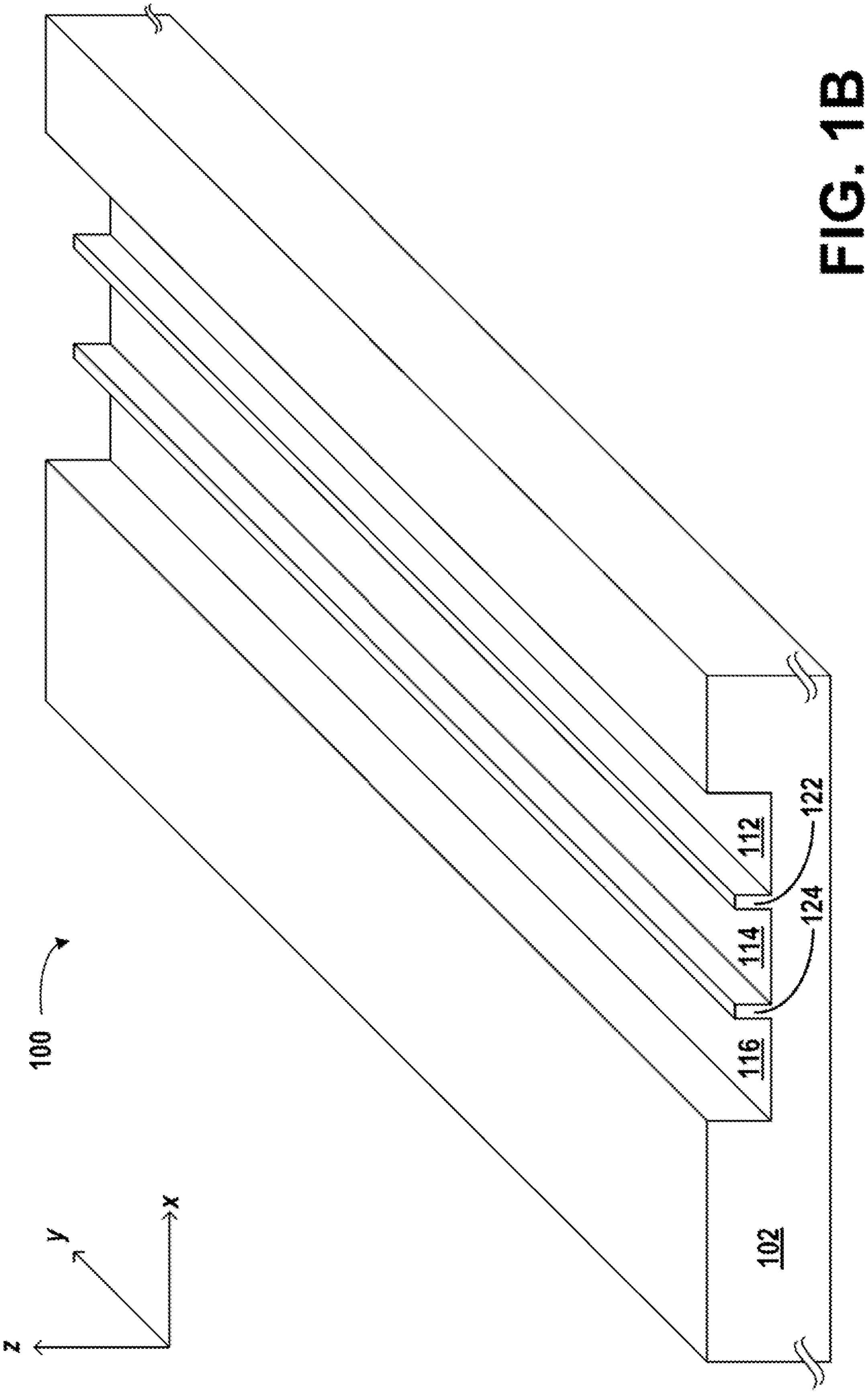
FIG. 1B is an isometric illustration of a bioreactor tile, according to example embodiments.

FIG. 1A is an isometric illustration of a bioreactor tile 100, according to example embodiments. The bioreactor tile 100 may include a substrate 102 having a first channel 112 (i.e., a nutrient channel 112), a second channel 114 (i.e., a plant cell channel 114), and a third channel 116 (i.e., product channel 116) defined therein. The first channel 112 may be separated from the second channel 114 by a first partial wall structure 122 and the second channel 114 may be separated from third channel 116 by a second partial wall structure 124. The bioreactor tile 100 may also include an optical waveguide 132. The arrangement of the bioreactor tile 100 of FIG. 1A may be referred to as a single-sided arrangement. FIG. 1B is an isometric illustration of the same bioreactor tile 100 as FIG. 1A, with the optical waveguide 132 removed from the illustration to make the underlying structures of the first channel 112, the second channel 114, the third channel 116, the first partial wall structure 122, and the second partial wall structure 124 more clearly visible.

The substrate 102 may include a surface into which one or more structures (e.g., the first channel 112, the second channel 114, the third channel 116, the first partial wall structure 122, and/or the second partial wall structure 124)

are defined (e.g., via etching) and/or onto which one or more structures are deposited (e.g., via chemical vapor deposition (CVD)). For example, the substrate 102 may include a transparent polymer (e.g., polydimethylsiloane (PDMS)), glass (e.g., fused silica, borosilicate, soda-lime glass, etc.), thermoplastics (e.g., poly(methyl methacrylate) (PMMA), acrylic, polycarbonate, optically clear polyvinyl chloride (PVC), polyethylene terephthalate glycol (PETG), etc.), polylactic acid (PLA), thermoset polymers, and/or a Si wafer that may be processed (e.g., using microfabrication techniques, additive manufacturing techniques, or molding techniques) to define structures into the substrate 102. Other substrates are also possible and are contemplated herein. As illustrated by the discontinuous lines oriented along a z-direction of the substrate, in some embodiments, a thickness of the substrate (e.g., between 500 μm and 3,000 μm) may be considerably larger than a thickness of the channels 112, 114, 116 (e.g., between 250 μm and 2,000 μm) and/or the partial wall structures 122, 124 (e.g., between 250 μm and 1,500 μm).

The first channel 112, the second channel 114, and the third channel 116 may run substantially parallel to one another (e.g., parallel to they-axis), as illustrated in FIGS. 1A and 1B. In some embodiments, the first channel 112, the second channel 114, and the third channel 116 may be fluidic channels (e.g., microfluidic channels or larger-scale channels). For example, the first channel 112, the second channel 114, and/or the third channel 116 may be: between 250 μm and 2,000 μm in width (x-dimension in FIG. 1A), between 10 cm and 100 cm in length (y-dimension in FIG. 1A), and between 500 μm and 2,000 μm in height (z-dimension in FIG. 1A). In some embodiments, the first channel 112, the second channel 114, and the third channel 116 may be configured to house different substances of the bioreactor tile 100. For example, as shown and described further below with reference to FIG. 1D, the first channel 112 may be configured to house nutrients (e.g., a liquid nutrient media), the second channel 114 may be configured to house plant cells (e.g., within a gel from a cellular precursor), and the third channel 116 may be configured to house products (e.g., trichomes that are produced by the plant cells and are growing in an air environment within the third channel 116).

Further, as illustrated and described above, the first channel 112 may be separated from the second channel 114 by the first partial wall structure 122. In some embodiments, the first partial wall structure 122 may be between 250 μm and 1,000 μm in width (x-dimension in FIG. 1A), between 10 cm and 100 cm in length (v-dimension in FIG. 1A), and between 250 μm and 1,500 μm in height (y-dimension in FIG. 1A). The first partial wall structure 122 may serve to separate the two channels 112, 114 from one another while still permitting some contact between the two channels 112, 114. For example, surface tension present in a fluid in the first channel 112, a fluid in the second channel 114, or both might (along with the first partial wall structure 122 itself) form an effective barrier between the first channel 112 and the second channel 114. However, in a region above the first partial wall structure 122, the contents/fluid in the first channel 112 may be in contact with the contents/fluid in the second channel 114, which may allow substances (e.g., nutrients) within the first channel 112 to be transported to the second channel 114 (e.g., via diffusion). Similarly, the second partial wall structure 124 may serve to separate the second channel 114 from the third channel 116 while still permitting some contact between the two channels 114, 116 (e.g., thereby allowing substances, such as trichomes within the second channel 114 to grow/extend into the third channel 116). Like the first partial wall structure 122, the second partial wall structure 124 may be between 250 μm and 1,000 μm in width (x-dimension in FIG. 1A), between 10 cm and 100 cm in length (y-dimension in FIG. 1A), and between 250 μm and 1,500 μm in height (z-dimension in FIG. 1A).

While the first channel 112, the second channel 114, and the third channel 116 are illustrated in FIGS. 1A and 1B as having roughly the same dimensions (e.g., same width, depth, and length), it is understood that other embodiments are also possible. For example, one of the channels 112, 114, 116 may be wider and/or deeper than the other two channels to accommodate additional volume (e.g., the second channel 114 may be deeper than the other two channels, shallower than the other two channels, wider than the other two channels, or narrower than the other two channels). Additionally or alternatively, one of the channels 112, 114, 116 may be longer than the other two channels so as to connect it to an inlet that is at a different location within the bioreactor tile 100 than the inlets of the other two channels. Similarly, while the first partial wall structure 122 and the second partial wall structure 124 are illustrated in FIGS. 1A and 1B as having roughly the same dimensions (e.g., same width, height, and length), it is understood that other embodiments are also possible. For example, one of the partial wall structures 122, 124 may be narrower and/or shorter than the other partial wall structure (e.g., to promote additional fluid interaction between the channels adjacent to that partial wall structure). Further, in some embodiments, one or both of the partial wall structures 122, 124 may have excised portions (e.g., removed sections along the y-axis illustrated in FIGS. 1A and 1B) that further promote fluid interaction between channels adjacent to that partial wall structure.

The first channel 112, the second channel 114, the third channel 116, the first partial wall structure 122, and/or the second partial wall structure 124 may be fabricated (e.g., may be defined within the substrate 102) using a variety of fabrication techniques (e.g., microfabrication techniques performed within a cleanroom setting or additive manufacturing techniques). For example, fabricating the bioreactor tile 100 may include providing the substrate 102 (e.g., a PMMA wafer or an acrylic wafer) and performing one or more etching steps. Such etching steps may include selective etching steps, chemical etching steps, wet etching steps, dry etching steps, etc. Further, in embodiments where selective etching steps are performed, one or more photolithography processing steps (e.g., to define one or more masks used to perform the selective etching steps) may also be performed. The etch depths used to define the channels 112, 114, 116 may be different than the etch depths used to define the partial wall structures 122, 124, for example. Additionally or alternatively, in some embodiments, one or more planarization processes may be performed (e.g., a chemical-mechanical polishing (CMP) process) during the fabrication of the bioreactor tile 100. Still further, in some embodiments, a plasma bonding process and/or a dry bonding process may be performed during the fabrication of the bioreactor tile 100. It is understood that, while microfabrication techniques can be used in fabrication, various embodiments may also incorporate some (e.g., may incorporate exclusively) fabrication techniques that are of such a size/scale that such microfabrication techniques are not necessary.

Returning to FIG. 1A, the optical waveguide 132 may be fabricated along with the substrate 102 and the channels 112, 114, 116/partial wall structures 122, 124 defined therein. Alternatively, the optical waveguide 132 may be fabricated separately from the substrate 102 and the channels 112, 114, 116/partial wall structures 122, 124 defined therein and later attached to the substrate 102 and the channels 112, 114, 116/partial wall structures 122, 124 defined therein to form the bioreactor tile 100. The optical waveguide 132 may receive electromagnetic waves (e.g., illumination light) at a first end (e.g., an input end) of the optical waveguide 132 (e.g., via an optical coupling to the optical waveguide 132, as shown and described with reference to FIG. 1C). For example, as illustrated in FIG. 1A, the optical waveguide 132 may receive light at an end of the optical waveguide 132 having the greatest y-position (as illustrated by the axes in FIG. 1A). In some embodiments, for instance, the optical waveguide 132 may receive illumination light from an illumination system of a bioreactor (e.g., the bioreactor 500 shown and described below with reference to FIG. 5). Upon receiving the electromagnetic waves, the electromagnetic waves may propagate along the optical waveguide 132 toward a second end of the optical waveguide 132 (e.g., an end of the optical waveguide 132 having the lowest y-position, as illustrated in FIG. 1A).

Propagation of electromagnetic waves along the optical waveguide 132 may occur, at least partially, due to total internal reflection from one or more surfaces of the optical waveguide 132. For example, in some embodiments, the optical waveguide 132 may be fabricated from $SiO_2$. As such, there may be a mismatch between the material of the optical waveguide 132 and the surrounding environment of the optical waveguide 132 (e.g., air). This material mismatch may also correspond to a mismatch in relative dielectric constants ($\varepsilon_r$)/refractive indices ($\eta$). For example, in embodiments where the optical waveguide 132 is fabricated from $SiO_2$ and the surrounding environment is air, the mismatch of relative dielectric constants may be ~3.9 ($\varepsilon_r$ of $SiO_2$) to ~1 ($\varepsilon_r$ of air). It is understood that these values are given solely as examples, and that other materials may be used and/or the materials listed may have different relative dielectric constants depending on the wavelength of electromagnetic signal propagating within the materials. As a result of Snell's law, such a material mismatch may lead to total internal reflection for a specified range of incidence angles of the electromagnetic waves. It is understood that other materials besides $SiO_2$ for the optical waveguide 132 are also possible and are contemplated herein (e.g., PMMA, polycarbonate, polyetherimide, ZnO, high-index glasses). Further, while the optical waveguide 132 of FIGS. 1A and 1C may not have an optical coating, it is understood that, in other embodiments, the optical waveguide 132 may have one or more portions coated with an optical coating (e.g., a reflective optical coating) to prevent illumination light from escaping the optical waveguide 132 at the coated regions.

Further, as illustrated in FIG. 1A, the optical waveguide 132 may be positioned above (e.g., suspended above, mounted above, cantilevered above, etc.) the second channel 114 and the third channel 116. As such, the optical waveguide 132 may provide illumination light (e.g., illumination light received at the first end of the optical waveguide 132) to the second channel 114 or the third channel 116 (e.g., in order to provide conditions conducive to the growth of plant cells in the second channel 114 and/or the growth of trichome cells in the third channel 116). This is illustrated by the light rays emitted from the bottom of the optical waveguide 132 in FIG. 1A. Providing the illumination light to the second channel 114 and/or the third channel 116 may occur as a result of one or more surface features present on an underside (e.g., a flat bottom surface) of the optical waveguide 132 that allow illumination light to escape the optical waveguide 132 (e.g., that interrupt total internal reflection) as the illumination light propagates in the optical waveguide 132. For example, the bottom surface of the optical waveguide 132 may include diffractive features, longitudinal striations (e.g., running parallel to they-axis illustrated in FIG. 1A), lateral striations (e.g., running parallel to the x-axis illustrated in FIG. 1A), or pits.

In addition, one or more surfaces of the optical waveguide 132 may be tapered. For example, as illustrated in FIG. 1A, a top surface of the optical waveguide 132 (e.g., a surface of the optical waveguide 132 having the greatest z-position) may be tapered (e.g., from a first end of the optical waveguide 132 to a second end of the optical waveguide 132). Such a tapering may provide for a relatively uniform intensity of illumination light provided to the second channel 114 and/or the third channel 116 by the optical waveguide 132. In other embodiments, other shapes of optical waveguide 132 may be used. For example, the intensity of the illumination light provided to the second channel 114 and/or the third channel 116 may substantially vary along the length (e.g., y-position) of the second channel 114 and/or the third channel 116.

It is understood that other positions of the optical waveguide 132 are also possible and are contemplated herein. For example, the optical waveguide 132 may be positioned adjacent to, below, or otherwise near one or more of the channels 112, 114, 116. It is also understood that other numbers of optical waveguides within the bioreactor tile 100 (e.g., two optical waveguides, three optical waveguides, four optical waveguides, etc.) are also possible and are contemplated herein. Such alternative possibilities are further shown and described with reference to FIGS. 2, 3A, and 4.

Figure 1C:
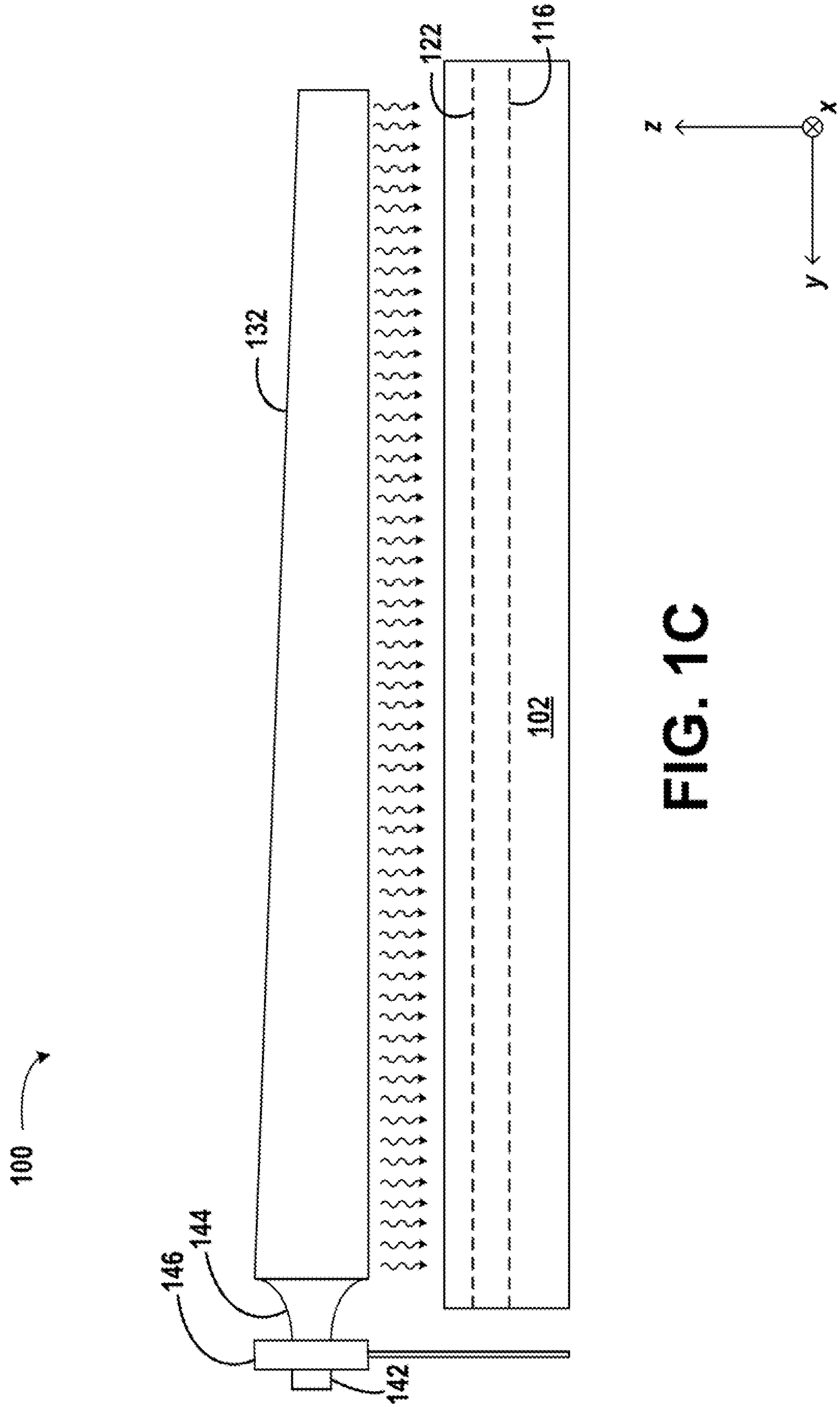
FIG. 1C is a side-view illustration of a bioreactor tile, according to example embodiments.

FIG. 1C is a side-view illustration (i.e., parallel to the y-z plane, as illustrated) of the bioreactor tile 100 illustrated and described with reference to FIGS. 1A and 1B. As illustrated by dashed lines in FIG. 1C, the third channel 116 and the second partial wall structure 124 may be defined within and obscured by a side of the substrate 102. As further illustrated in FIG. 1C, the optical waveguide 132 of the bioreactor tile 100 may also include a mixing region 142 and a coupling region 144. The mixing region 142 of the optical waveguide 132 may receive illumination light from an illumination source (e.g., a LED or other light emitter of an illumination system that is part of a multi-tile bioreactor, as described above). Further, the bioreactor tile 100 may include a mounting structure 146 used to support the optical waveguide 132. The mixing region 142, the coupling region 144, and the mounting structure 146 may each be components present in FIG. 1A, for example, but that are obscured by other components based on the isometric view of FIG. 1A.

The mixing region 142 may be configured to homogenize modes or wavelengths present within the illumination light received at the first end of the optical waveguide. For example, the mixing region 142 may combine illumination light having different modes into a single mode (e.g., by modifying modes that correspond to modes other than a predetermined mode so that they match the predetermined mode). Further, in some embodiments, the mixing region 142 may select only a predefined range of wavelengths from a group of input wavelengths (e.g., from illumination light coming from multiple illumination sources of an illumination system). For example, the mixing region 142 may attenuate, reflect, or otherwise reject light having wavelengths outside of the predefined range of wavelengths, thereby preventing wavelengths outside of the predefined range from propagating through the coupling region 144 and/or the remainder of the optical waveguide 132. In some embodiments, the mixing region 142 may be fabricated of the same material as the rest of the optical waveguide 132 (e.g., as the coupling region 144). Alternatively, though, the mixing region 142 may be fabricated from a different material than the rest of the optical waveguide 132.

The coupling region 144 may be configured to couple illumination light (e.g., the homogenized illumination light from the mixing region 142) into a main body of the optical waveguide. As such, the coupling region 144 may be tapered from the mixing region 142 to the main body of the optical waveguide 132. In various embodiments, the taper of the coupling region 144 may have various shapes 1 lengths (i.e., y-dimensions). For example, the length of the taper of the coupling region 144 may be based on a predetermined range of illumination wavelengths to be used with the optical waveguide 132 (e.g., to be received by the optical waveguide 132 at the mixing region 142 and/or to be provided from the optical waveguide 132 to the second channel 114 and/or the third channel 116). In some embodiments, the coupling region 144 may be fabricated of the same material as the main body of the optical waveguide 132. Alternatively, though, the coupling region 144 may be fabricated from a different material than the rest of the optical waveguide 132.

The mounting structure 146 may be a structure of the bioreactor tile 100 to which one or more optical waveguides (e.g., the optical waveguide 132) is attached/mounted. For example, as illustrated in FIG. 1C, the mounting structure may include a slot through which a portion of the optical waveguide 132 (e.g., the mixing region 142 and/or the coupling region 144) is passed/on which the optical waveguide 132 rests. The optical waveguide 132 may extend from the slot over the substrate 102 (e.g., may be cantilevered over the substrate) as illustrated in FIG. 1C. In some embodiments, the mounting structure 146 may be defined within or attached to the substrate 102. In other embodiments, the mounting structure 146 may be freestanding within the bioreactor tile 100. In some embodiments, there may be multiple mounting structures associated with a single optical waveguide. For example, there may be a first mounting structure positioned at the first end of the substrate to support the optical waveguide from the first end. Additionally, there may be a second mounting structure positioned at a second end of the substrate (e.g., an opposite end of the substrate from the first mounting structure) and configured to support the optical waveguide from the opposite end. In still other embodiments, there may be more than two mounting structures. Still further, it is understood that in some embodiments the mounting structure 146 may have a different shape, size, or position (e.g., the mounting structure 146 may run the length of the substrate 102, the mounting structure 146 may be positioned at the center of the substrate 102 rather than at an edge of the substrate 102, the mounting structure 146 may be taller in z-dimension, the mounting structure 146 may be shorter in z-dimension, the mounting structure 146 may be longer in y-dimension, the mounting structure 146 may be shorter in y-dimension, etc.).

FIG. 1D is a front-view illustration (i.e., parallel to the x-z plane, as illustrated) of the bioreactor tile 100 (e.g., as illustrated and described with reference to FIGS. 1A-1C) while the bioreactor tile 100 is in use (e.g., growing plant cells and trichomes). The optical waveguide 132 of the bioreactor tile 100 has been removed from the illustration of FIG. 1D so as to prevent the illustration from being cluttered. As illustrated, the first channel 112 may supply liquid nutrient media 152 to plant cells 164 contained within a gel 154 in the second channel 114. As also illustrated, the plant cells 164 in the second channel 114 may produce trichomes 166 that extend into the third channel 116.

The liquid nutrient media 152 may be pumped into the bioreactor tile 100 (e.g., by a pump of a fluid management system of a bioreactor 500 and/or from a tank of a fluid management system of a bioreactor 500, as shown and described below with reference to FIG. 5). For example, the liquid nutrient media 152 may enter an inlet or an intake port (e.g., an inlet/intake port that permits fluid communication between the first channel 112 and an exterior of the bioreactor tile 100) at one end of the first channel 112. Likewise, the liquid nutrient media 152 may exit the bioreactor tile 100 (e.g., by being pumped by a fluid management system and/or into a separate tank of a fluid management system of a bioreactor) via an outlet or an outtake port (e.g., an outlet/outtake port that permits fluid communication between the first channel 112 and an exterior of the bioreactor tile 100). For example, the liquid nutrient media 152 may be pumped out of the bioreactor tile 100 (e.g., pumped through and out of the first channel 112) once the nutrients contained in the liquid nutrient media 152 have been depleted/used by the plant cells 164 in the second channel 114.

In some embodiments, the liquid nutrient media 152 may include an inorganic salt, a carbon source, myoinositol, glycine, a vitamin, a growth regulator, a nitrogen compound, an organic acid, a plant extract, aluminum chloride, ammonium nitrate, ammonium phosphate, ammonium hydrogen phosphate, ammonium sulfate, boric acid, calcium chloride, calcium nitrate, calcium phosphate tribasic, cobalt chloride, cupric sulfate, ferric chloride, ferric citrate, ferric ethylenediaminetetraacetic acid (EDTA), ferric sulfate, ferric tartrate, magnesium sulfate, manganese chloride, manganese sulfate, molybdenum trioxide, sodium molybdate, nickel chloride, nickel sulfate, potassium chloride, potassium iodide, potassium nitrate, potassium hydrogen phosphate, potassium sulfate, sodium EDTA, sodium molybdate, sodium nitrate, sodium phosphate, sodium hydrogen phosphate, sodium dihydrogen phosphate, sodium sulfate, zinc nitrate, zinc sulfate, activated charcoal, adenosine hemisulfate, agar, 6-benzylamino purine, alpha naphthalene acetic acid, biotin, dichloro-phenoxy acetic acid, dimethylallylaminopurine, glycine, indole-3-acetic acid, indole-3-butyric acid, isopentenyl adenine, isopentenyl adeninoside, kinetin, MES (buffer), myo-inositol, nicotinic acid, peptone, pyridoxine hydrochloride, sucrose, thiamine, thiamine hydrochloride, auxins, cytokinins, gibberellins, or plant preservatives (e.g., included in the liquid nutrient media 152 at about 1% by volume). It is understood that these are provided solely as examples and that other types of liquid nutrient media 152 are also possible and are contemplated herein. Some of these types of nutrients may be suspended and/or dissolved in a liquid (e.g., water) for easier uptake by the plant cells 164. In some embodiments, the liquid nutrient media 152 may be made into gel formulations In some embodiments, the liquid nutrient media 152 may include a calli-induction media (e.g., including a base of Gamborg's B5 Basal Media combined with 50 mg/L myo-inositol, 10 mg/L of thiamine HCl, 1 g/L of casein hydrolysate, 3% sucrose, 1 mg/L of 1-napthaleneacetic acid, and 1 mg/L benzylamino purine), further, in some embodiments, liquid formulations may be made into gel formulations by adding gel powder prior to autoclaving. Additionally or alternatively, in some embodiments, the liquid nutrient media 152 may include trichome-induction media (e.g., including a base of Gamborg's B5 Basal Media combined with 50 mg/L myo-inositol, 10 mg/L of thiamine HCl, 1 g/L of casein hydrolysate, 3% sucrose, 1 mg/L of 1-napthaleneacetic acid, and 1 mg/L benzylamino purine, as well as 0.5-1.0 mg/L of thidiazuron and 3 mg/L gibberellic acid added after autoclaving).

Additionally or alternatively, the gel 154 may include agar gel, agarose gel, alginate gel, gelatin gel, acrylamide gel, silica gel, cellulose gel, methylcellulose gel, and/or a highly purified, natural heteropolysaccharide that forms stable, agar-like gels when exposed to soluble salts. It is understood that these are provided solely as examples and that other types of gels 154 are also possible and are contemplated herein.

Still further, the plant cells 164 may include parenchymal plant cells (e.g., originally provided in protoplast cell cultures, suspension cell cultures, or micro-calli cell cultures), in some embodiments. The parenchymal cells may include *Cannabis sativa* cells, *Artemisia annua* cells, *Chrysanthemum cinerarifolium* cells, *Chrysanthemum coccineum* cells, *Gossypium hirsutum* cells, *Gossypium barbadense* cells, *Gossypium arboreum* cells, *Gossypium herbaceum* cells, *Lavandula angustifolia* cells, *Arabidopsis thaliana* cells, *Mentha* x *piperita* cells, and/or *Mentha haplocalyx* cells, in various embodiments. It is understood that these are provided solely as examples and that other types of plant cells 164 are also possible and are contemplated herein (e.g., spongey mesenchymal cells or palisade cells).

The plant cells 164 may be interspersed throughout the gel 154 matrix (or cultured in a neighboring channel, based on embodiment). While only one plant cell 164 is illustrated in FIG. 1D, it is understood that this is done solely for illustration and that, in many embodiments, tens, hundreds, thousands, millions, etc. of plant cells may be present within the gel 154 of the second channel 114. In some embodiments, the plant cells 164 may have been seeded into an unset gel mixture (e.g., an unset version of the gel 154, sometimes referred to as a gel precursor media). That unset gel mixture with the seeded plant cells 164 therein may be referred to as a cellular precursor. The cellular precursor may have been infused into the second channel 114 and then allowed to solidify (e.g., over a predetermined amount of time, such as between 0.25 hours and 2.0 hours) or caused to solidify (e.g., by infusing a solidifying agent, such as $CaCl_2$) to form the gel 154 with the plant cells therein 164. The gel 154 may have a low enough density so as to permit the plant cells 164 to grow, multiply, and generate the trichomes 166 that extend into the third channel 116. In some embodiments, prior to infusing the cellular precursor into the second channel 114, a sterilization procedure may be performed (e.g., to sterilize the bioreactor tile 100). The sterilization procedure may include heating the substrate 102 (with the channels 112, 114, 116 defined therein) and/or the optical waveguide 132 to a first predetermined temperature (e.g., to between 175° C. and 185° C.) for a first predetermined time period (e.g., 5 minutes, 10 minutes, 15 minutes, 30 minutes, 45 minutes, 1 hour, 2 hours, 3 hours, etc.), followed by cooling the substrate 102 (with the channels 112, 114, 116 defined therein) and/or the optical waveguide 132 to a second predetermined temperature (e.g., between 20° C. and 25° C.). Such a heating and/or cooling may be performed using an environmental control system of a bioreactor that houses the bioreactor tile (e.g., the bioreactor 500 shown and described below with reference to FIG. 5). Additionally or alternatively, the sterilization procedure may include a radiation procedure (e.g., illumination with ultraviolet light) and/or a chemical sterilization procedure (e.g., using one or more cleaning solutions or gases). A radiation sterilization procedure may be performed using an illumination system of a bioreactor that houses the bioreactor tile (e.g., the bioreactor 500 shown and described below with reference to FIG. 5). Similarly, a chemical sterilization procedure may be performed using a fluid management system of a bioreactor that houses the bioreactor tile (e.g., the bioreactor 500 shown and described below with reference to FIG. 5). For example, the sterilization procedure may be a chemical sterilization procedure that includes applying a 7%-10% bleach solution, followed by autoclaving with distilled water, followed by applying a 80% ethanol solution, followed by autoclaving with distilled water, followed by drying (e.g., using clean air). Other sterilization procedures are also possible and are contemplated herein (e.g., including procedures that apply detergent, $H_2O_2$, plasma, dry heat, and/or steam).

In order to grow the plant cells 164, one or more sets of environmental conditions may be provided (e.g., provided to the second channel 114 or the third channel 116 of the bioreactor tile 100). Such sets of environmental conditions may be provided by an environmental control system of a larger bioreactor (e.g., the bioreactor 500 shown and described below with reference to FIG. 5). Further providing such a set of environmental conditions may include providing a temperature of between 20° C. and 25° C. to the second channel 114 or the third channel 116, providing a periodic lighting condition (e.g., using a illumination source of an illumination system and/or an optical waveguide, such as the optical waveguide 132 illustrated in FIGS. 1A and 1C) that repeatedly alternates from about 16 hours of light to about 8 hours of dark, and providing a calli-induction media (e.g., as part of the liquid nutrient media 152) in the first channel 112. In some embodiments, instead of providing between 20° C. and 25° C. continuously, a temperature may be provided of between 18° C. and 30° C. during the 16 hours of light, while a temperature of between 5° C. and 10° C. is provided during the 8 hours of darkness. Still further, in some embodiments, providing such a set of environmental conditions may also include providing (e.g., by an environmental control system of an associated bioreactor) an air humidity of between 30% and 50% (e.g., in the air supplied to the plant cells 164 through via the third channel 116).

As illustrated in FIG. 11D, the gel 154 and plant cells 164 in the second channel 114 may be separated from the liquid nutrient media 152 in the first channel 112 by the first partial wall structure 122. Based on the first partial wall structure 122 and the surface tension in the liquid nutrient media 152 and the gel 154/plant cell 164 mixture, the two channels may be effectively prevented from mixing within one another while nutrients can still be transported from the liquid nutrient media 152 to the plant cells 164.

The gel 154 (e.g., in liquid form) and plant cell 164 mixture may be pumped into the bioreactor tile 100 (e.g., by a pump and/or from a tank of a fluid management system of a bioreactor 500, as shown and described below with reference to FIG. 5). For example, a cellular precursor that includes the gel 154 and the plant cells 164 may enter an inlet or an intake port (e.g., an inlet/intake port that permits fluid communication between the second channel 114 and an exterior of the bioreactor tile 100) at one end of the second channel 114. Likewise, the gel 154 and plant cell 165 mixture may exit the bioreactor tile 100 (e.g., by being pumped into a separate tank of a fluid management system of a bioreactor) via an outlet or an outtake port (e.g., an outlet/outtake port that permits fluid communication between the second channel 114 and an exterior of the bioreactor tile 100). For example, the gel 154 and plant cell 164 mixture may be pumped out of the bioreactor tile 100 (e.g., pumped through the second channel 114) once the plant cells 164 have ceased producing trichomes and/or once the trichomes 166 in the third channel 116 are harvested. In some embodiments, the gel 154 and plant cell 164 mixture may be used for multiple cycles of producing trichomes/harvesting trichomes prior to being pumped out of the bioreactor tile 100.

As also illustrated in FIG. 1D, the gel 154 and plant cells 164 in the second channel 114 may be separated from the trichomes 166 in the third channel 116 by the second partial wall structure 124. Based on the second partial wall structure 124 and the surface tension in the gel 154/plant cell 164 mixture, the two channels may be effectively prevented from mixing within one another (e.g., the gel 154 does not penetrate into the third channel 116 even when in a liquid state) while trichomes 166 produced by the plant cells 164 in the second channel 114 can still extend into the third channel 116.

The trichomes 166 may be produced by the plant cells 164. For example, *Cannabis sativa* parenchymal cells may produce *Cannabis sativa* trichomes. Further, in some embodiments, the trichomes 166 may contain products (e.g., chemicals) that are ultimately to be harvested from the bioreactor tile 100 (e.g., by being pumped out of the bioreactor tile 100 by a fluid management system using an extractant). For example, the trichomes may produce/contain cannabidiol, tetrahydrocannabinol, artemisinin, pyrethrum, camphor, glucosinolate, linalool, linalyl acetate, menthol, or peppermint camphor.

In order to cause the plant cells 164 to produce the trichomes 166, one or more sets of environmental conditions may be provided (e.g., provided to the second channel 114 or the third channel 116 of the bioreactor tile 100). Such sets of environmental conditions may be provided by an environmental control system of a larger bioreactor (e.g., the bioreactor 500 shown and described below with reference to FIG. 5). Further providing such a set of environmental conditions may include providing a temperature of between 20° C. and 25° C. to the second channel 114 or the third channel 116, providing a periodic lighting condition (e.g., using a illumination source and/or an optical waveguide, such as the optical waveguide 132 illustrated in FIGS. 1A and 1C) that repeatedly alternates from about 12 hours of light to about 12 hours of dark, and providing a trichome-induction media (e.g., as part of the liquid nutrient media 152) in the first channel 112. In some embodiments, the trichome-induction media may include plant hormones that induce callus formation, which results in the production of trichomes by the plant cells 164.

Once the trichomes 166 reach a mature state, the trichomes 166 and/or the products within the trichomes 166 may be harvested from the third channel 116. In some embodiments, one or more sensors, such as one or more optical monitoring systems (e.g., including a camera 402, as shown and described with reference to FIG. 4), may be used to monitor the trichomes 166 in order to determine when the trichomes 166 have reached a mature state for harvesting. For example, hyperspectral representations of the trichomes 166 and/or associated parenchymal cells may be captured. Then, based on a spectral signature of the trichomes 166 and/or associated parenchymal cells contained in the hyperspectral representations, a controller of the bioreactor 500 may determine that the product is to be harvested from the trichomes 166. A similar process may also be performed to determine when the production cycle is to progress from a parenchymal growth stage (e.g., callus-growth phase) to a trichome-production phase. For example, the controller of the bioreactor 500 may evaluate a hyperspectral signature of the parenchymal cells to determine when the parenchymal cells are of sufficient maturity to begin producing trichomes 166.

Harvesting the trichomes 166 and/or the products within the trichomes 166 may include shearing the trichomes from the underlying plant cells 164 (e.g., the underlying parenchymal cells) and extracting the trichomes from the third channel 116 by flushing the third channel 116 with a liquid flow (e.g., by infusing extractant, such as ethanol, ice-cold water, or another solvent, into the third channel 116 using a fluid management system of an associated bioreactor). Thereafter, a separation step may be performed (e.g., within a different region of a bioreactor, such as the bioreactor 500 shown and described below with reference to FIG. 5) to separate the product contained within the trichomes 166 from the trichomes 166 and/or to separate the product (e.g., cannabidiol) from the extractant (e.g., by falling-film evaporation, roto-evaporation, drying, distillation, short-path distillation, and/or lyophilization). Alternatively, in some embodiments the trichomes 166 may be ruptured in order to release the product into the third channel 116, and the product may be retrieved from the third channel 116 (e.g., by flushing the third channel 116 with a liquid flow). In such embodiments, the ruptured trichomes may be sheared/extracted thereafter (e.g., separately from the products).

In some embodiments, harvesting the trichomes 166 or the products within the trichomes 166 may include providing a temperature of less than 4° C. to the second channel 114 and/or the third channel 116 (e.g., using an environmental control system of a bioreactor, such as the bioreactor 500 shown and described with reference to FIG. 5). Further, harvesting the trichomes 166 or the products within the trichomes 166 may include providing no illumination light (e.g., from an illumination system of a bioreactor, such as the bioreactor 500 shown and described with reference to FIG. 5, via the optical waveguide 132) to the second channel 114 or the third channel 116. Additionally, harvesting the trichomes 166 or the products within the trichomes 166 may include flowing low-temperature (e.g., between −75° C. and 0° C.) extractant through the third channel 116 at a sufficient flow rate so as to shear the trichomes 166 from the plant cells 164 (e.g., using a fluid management system of a bioreactor, such as the bioreactor 500 shown and described with reference to FIG. 5). In some embodiments, the extractant may include one or more abrasive components (e.g., glass beads) to assist in shearing the trichomes 166 from the plant cells 164.

In some embodiments, once the trichomes 166 and/or the products within the trichomes 166 are harvested from the third channel 116, the second channel 114 and/or the first channel 112 may also be flushed (e.g., using a fluid management system of a bioreactor, such as the bioreactor 500 shown and described with reference to FIG. 5). For example, the gel 154 and the plant cells 164 within the gel 154 may be flushed from the second channel 114 (e.g., by liquefying the gel 154, such as via heating and/or enzymatic digestion, and using a fluid flow to force the liquefied gel 154 out of an outlet of the second channel 114). Additionally or alternatively, the liquid nutrient media 152 may be flushed from the first channel 112 (e.g., using a fluid flow from a fluid management system of an associated bioreactor to force the liquid nutrient media 152 out of an outlet of the first channel 112).

In other embodiments, once the trichomes 166 and/or the products within the trichomes 166 are harvested from the third channel 116, the plant cells 164 may be caused to regrow trichomes 166. For example, the liquid nutrient media 152 may be replaced with fresh calli-induction media and/or may be replaced with fresh trichome-induction media to cause the plant cells 164 to produce new trichomes 166 for harvesting. Such a process may be repeated multiple times to harvest multiple cycles of trichomes 166 without the need for replacing !regrowing the underlying plant cells 164 (e.g., assuming that the harvesting of the trichomes 166 in each cycle does not damage the underlying plant cells 164/the underlying gel 154 and/or does not compromise sterility within the bioreactor tile 100).

Figure 2:
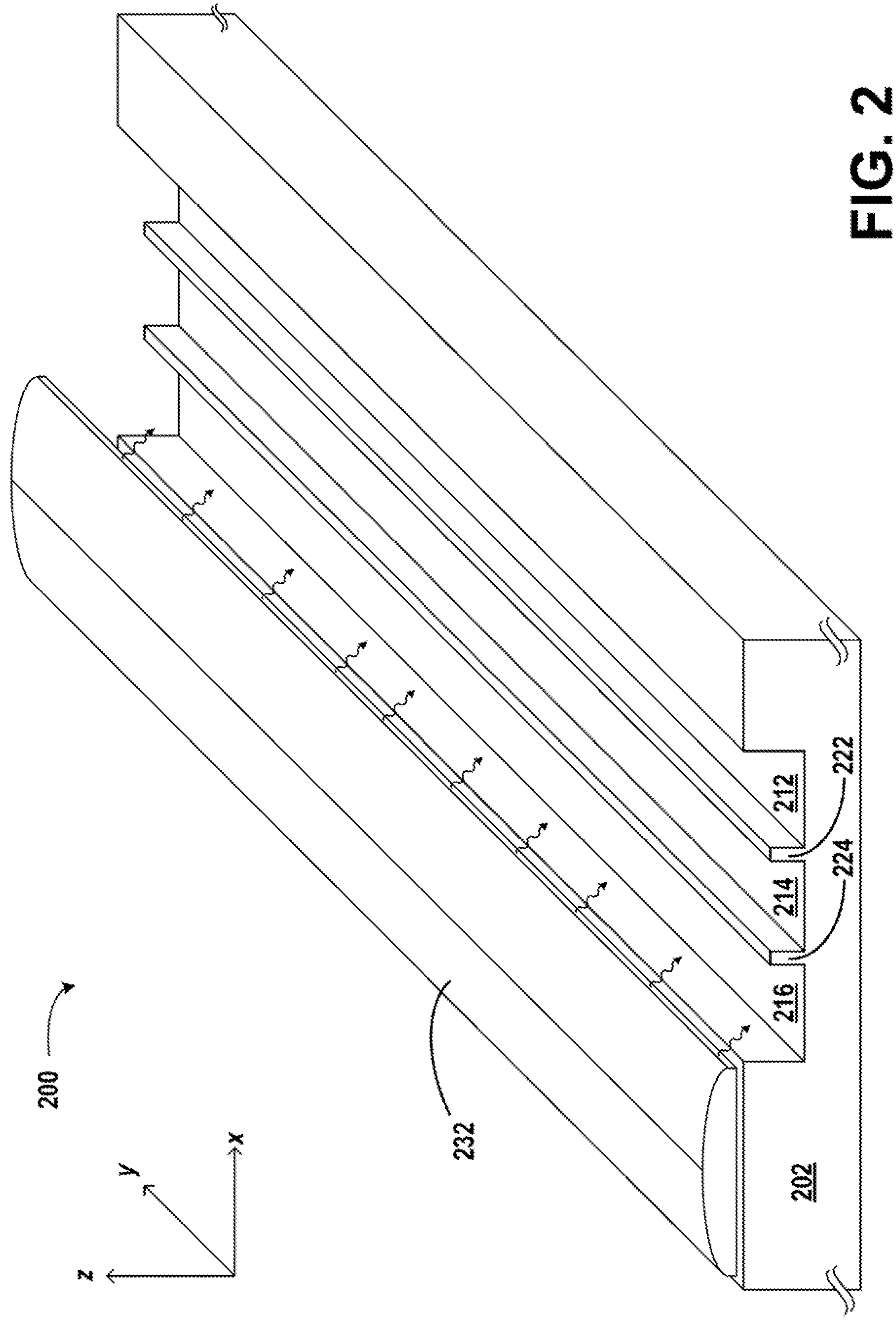
FIG. 2 is an isometric illustration of a bioreactor tile, according to example embodiments.

FIG. 2 is an isometric illustration of a bioreactor tile 200, according to example embodiments. Like the bioreactor tile 100 illustrated in FIGS. 1A-1D, the bioreactor tile 200 may include a substrate 202 having a first channel 212 (i.e., a nutrient channel 212), a second channel 214 (i.e., a plant cell channel 214), and a third channel 216 (i.e., product channel 216) defined therein. The first channel 212 may be separated from the second channel 214 by a first partial wall structure 222 and the second channel 214 may be separated from third channel 216 by a second partial wall structure 224. Also like the bioreactor tile 100 of FIGS. 1A-1D, the bioreactor tile 200 may also include an optical waveguide 232 (e.g., a $SiO_2$ optical waveguide). However, unlike the optical waveguide 132 of FIGS. 1A and 1C, the optical waveguide 232 of the bioreactor tile 200 in FIG. 2 is a surface-integrated optical waveguide.

Because the optical waveguide 232 illustrated in FIG. 2 is a surface-integrated optical waveguide, the optical waveguide 232 may be attached to or fabricated directly onto a surface of the substrate 202 (e.g., a surface of the substrate 202 that is adjacent to the third channel 216). For example, the optical waveguide 232 may be deposited onto the substrate 202 using a CVD process (e.g., a plasma-enhanced chemical vapor deposition process), deposited onto the substrate 202 using a sol-gel deposition process, sputtered onto the substrate 202, or grown on the substrate 202 (e.g., using a dry or wet thermal oxidation process). Also, the optical waveguide 232 may provide illumination light (e.g., illumination light received at the first end of the optical waveguide 232 from an illumination system of a bioreactor) to the second channel 214 or the third channel 216 (in order to provide conditions conducive to the growth of plant cells in the second channel 214 and/or the growth of trichome cells in the third channel 216) from an edge surface (e.g., as opposed to a bottom surface like the optical waveguide 132 illustrated in FIGS. 1A and 1C). This is illustrated in FIG. 2 by the light rays emitted from the edge surface of the optical waveguide 232. Similar to the bottom surface of the optical waveguide 132 in FIGS. 1A and 1C, providing the illumination light via the edge surface to the second channel 214 and/or the third channel 216 may occur based on one or more surface features present on the edge surface of the optical waveguide 232 that allow illumination light to escape the optical waveguide 232 (e.g., that interrupt total internal reflection) as the illumination light propagates in the optical waveguide 232. For example, the edge surface of the optical waveguide 232 may include diffractive features, longitudinal striations (e.g., running parallel to the y-axis illustrated in FIG. 2), lateral striations (e.g., running parallel to the z-axis illustrated in FIG. 2), or pits.

Also like the optical waveguide 132 illustrated in FIGS. 1A and 1C, one or more surfaces of the optical waveguide 232 may be tapered. For example, a top surface of the optical waveguide 232 (e.g., a surface of the optical waveguide 232 having the highest z-position) may be tapered (e.g., from a first end of the optical waveguide 232 to a second end of the optical waveguide 232). Such a tapering may provide for a relatively uniform intensity of illumination light provided to the second channel 214 and/or the third channel 216 by the optical waveguide 232. In other embodiments, other shapes of optical waveguide 232 may be used. For example, the intensity of the illumination light provided to the second channel 214 and/or the third channel 216 may substantially vary along the length (e.g., y-position) of the second channel 214 and/or the third channel 216.

Figure 3A:
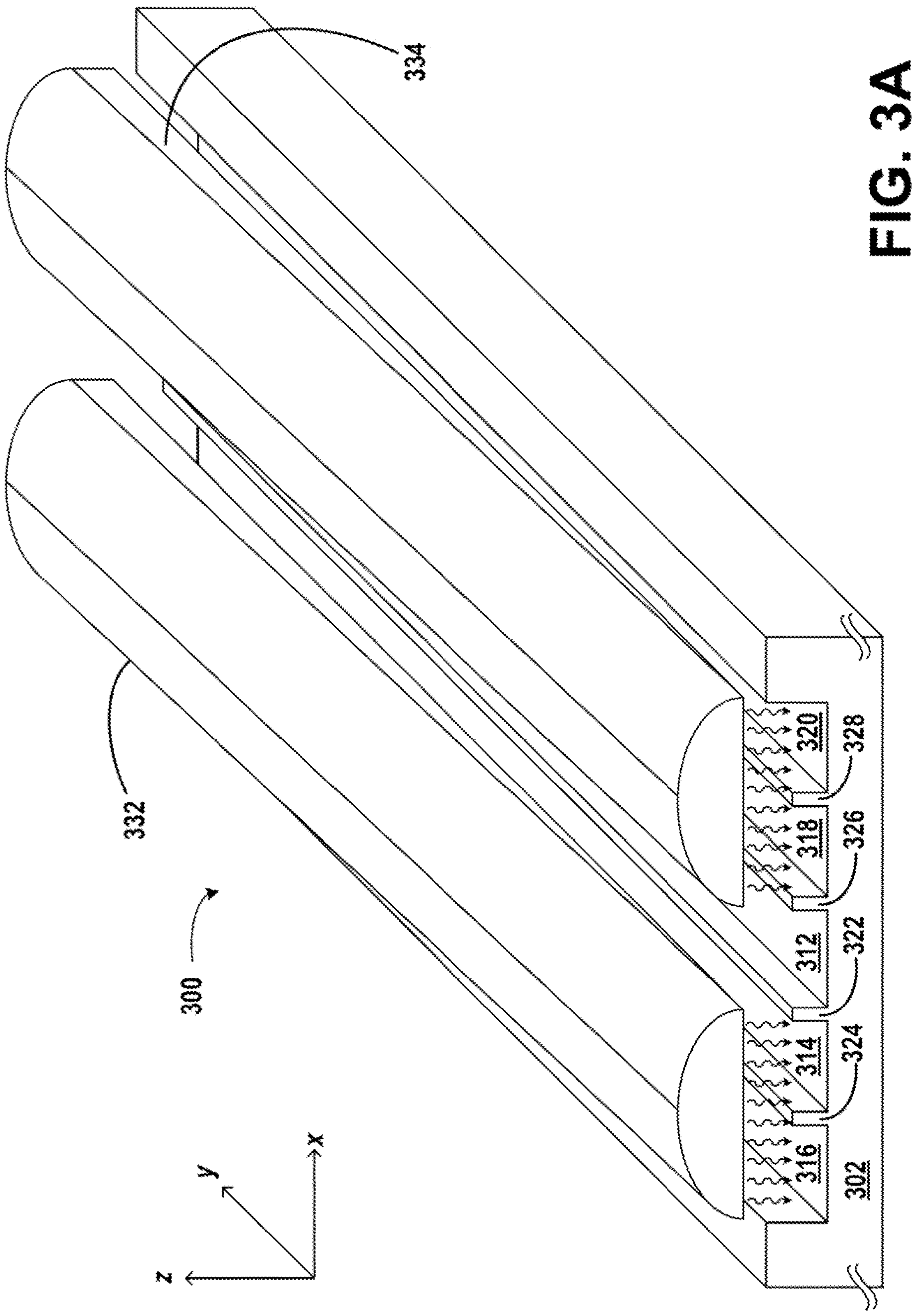
FIG. 3A is an isometric illustration of a bioreactor tile, according to example embodiments.

FIG. 3A is an isometric illustration of a bioreactor tile 300, according to example embodiments. The bioreactor tile 300 may include a substrate 302 having a first channel 312 (i.e., nutrient channel 312), a second channel 314 (i.e., plant cell channel 314), a third channel 316 (i.e., product channel 316), a fourth channel 318 (i.e., plant cell channel 318), and a fifth channel 320 (i.e., product channel 320) defined therein. The first channel 312 may be separated from the second channel 314 by a first partial wall structure 322, the second channel 314 may be separated from third channel 316 by a second partial wall structure 324, the first channel 312 may be separated from the fourth channel 318 by a third partial wall structure 326, and the fourth channel 318 may be separated from the fifth channel 320 by a fourth partial wall structure 328. The bioreactor tile 300 may also include a first optical waveguide 332 and a second optical waveguide 334. The arrangement of the bioreactor tile 300 of FIG. 3A may be referred to as a double-sided arrangement, and may be similar to the single-sided arrangement illustrated in FIGS. 1A-1D (e.g., with the exception that the double-sided arrangement may permit additional production of product per unit time, per unit area on the substrate 302, per unit area within the bioreactor tile 300, and/or per unit volume within an associated bioreactor, when compared to the substrate 102/bioreactor tile 100 of the single-sided arrangement of FIGS. 1A-1D).

Figure 3B:
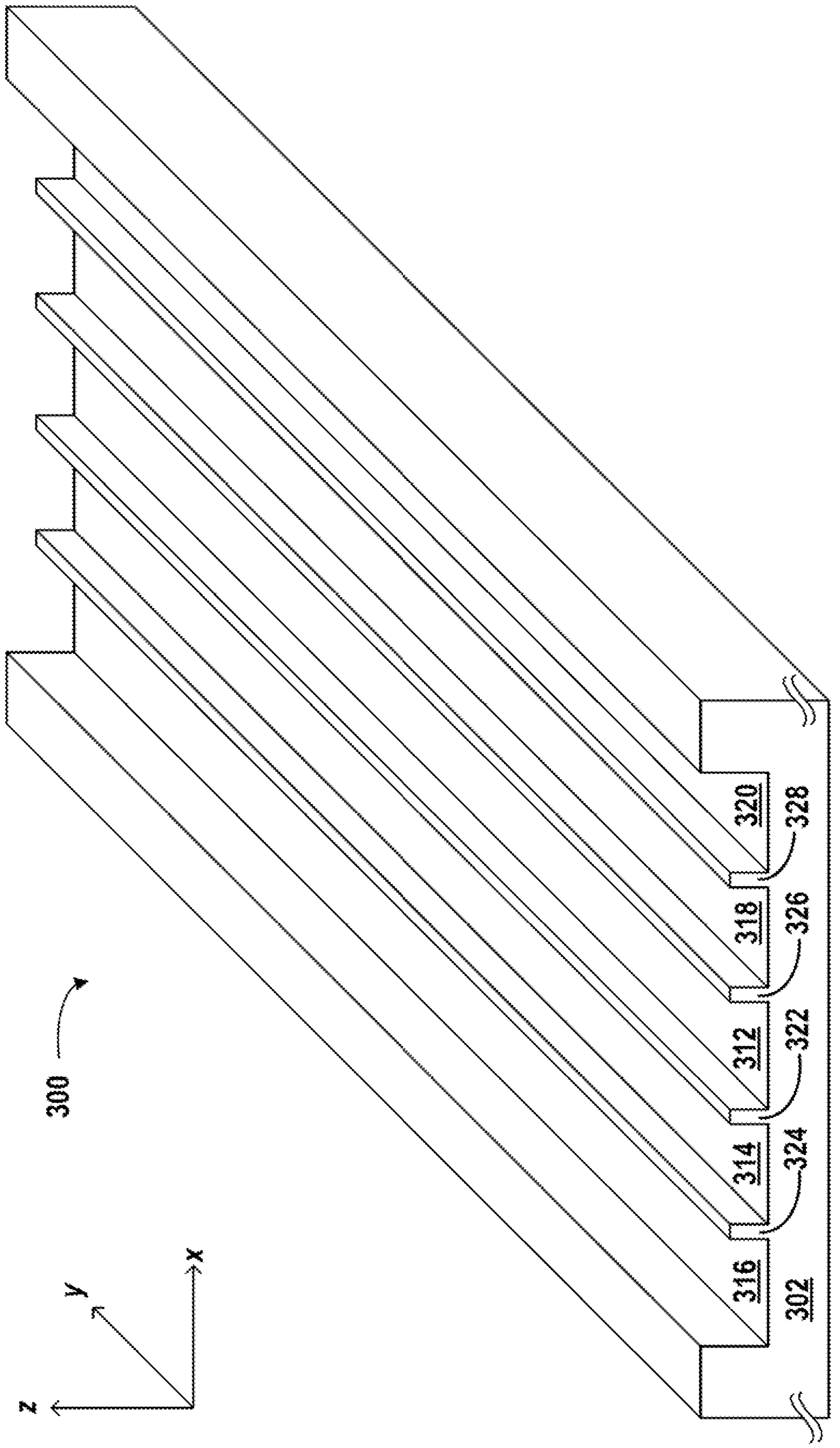
FIG. 3B is an isometric illustration of a bioreactor tile, according to example embodiments.

FIG. 3B is an isometric illustration of the same bioreactor tile 300 as FIG. 3A, with the optical waveguides 332, 334 removed to make the underlying structures of the first channel 312, the second channel 314, the third channel 316, the fourth channel 318, the fifth channel 320, the first partial wall structure 322, the second partial wall structure 324, the third partial wall structure 326, and the fourth partial wall structure 328 more clearly visible. As illustrated in FIG. 3B, the first channel 312, the second channel 314, the third channel 316, the fourth channel 318, and the fifth channel 320 may run substantially parallel to one another (e.g., parallel to they-axis). In some embodiments, the first channel 312, the second channel 314, the third channel 316, the fourth channel 318, and/or the fifth channel 320 may be fluidic channels (e.g., microfluidic channels or larger-scale channels).

The first optical waveguide 332 may be similar to the optical waveguide 132 illustrated and described with reference to FIGS. 1A and 1C. For example, the first optical waveguide 332 may be configured to provided illumination light to the second channel 314 and/or the third channel 316, may have surface features that allow illumination light to escape a bottom surface of the first optical waveguide 332, and/or may be tapered from a first end to a second end of the first optical waveguide 332. Likewise, the second optical waveguide 334 may be similar to the optical waveguide 132 illustrated and described with reference to FIGS. 1A and 1C. For example, the second optical waveguide 334 may be configured to provided illumination light to the fourth channel 318 and/or the fifth channel 320, may have surface features that allow illumination light to escape a bottom surface of the second optical waveguide 334, and/or may be tapered from a first end to a second end of the second optical waveguide 334. It is understood that the arrangement of FIG. 3A is provided solely as an example and that other embodiments are also possible. For example, in some embodiments, each separate channel may have its own respective optical waveguide (e.g., five optical waveguides, one for each of the five channels 312, 314, 316, 318, 320), each of the plant cell channels 314, 318 and the product channels 316, 320 may have its own respective optical waveguide (e.g., four optical waveguides, one for each of the first channel 312, the second channel 314, the fourth channel 318, and the fifth channel 320), or a single waveguide may be used to provide illumination light to all the channels 312, 314, 316, 318, 320. Other embodiments are also possible and are contemplated herein (e.g., embodiments having multiple surface-integrated optical waveguides, similar to the surface-integrated optical waveguide illustrated in FIG. 2).

FIG. 3C is a front-view illustration (i.e., parallel to the x-z plane, as illustrated) of the bioreactor tile 300 illustrated and described with reference to FIGS. 3A and 3B while the bioreactor tile 300 is in use (e.g., growing plant cells and trichomes). The optical waveguides 332, 334 of the bioreactor tile 300 have been removed from the illustration of FIG. 3C so as to prevent clutter. As illustrated, the first channel 312 may supply liquid nutrient media 352 to plant cells 364 contained within a gel 354 in the second channel 314 and to plant cells 374 contained within a gel 356 in the fourth channel 318. As also illustrated, the plant cells 364 in the second channel 314 may produce trichomes 366 that extend into the third channel 316 and the plant cells 374 in the fourth channel 318 may produce trichomes 376 that extend into the fifth channel 320. The substances contained within and the actions performed using the first channel 312 may be similar to that of the first channel 112 as shown and described with reference to FIG. 1D. Similarly, the substances contained within and the actions performed using the second channel 314 and the fourth channel 318 may be similar to that of the second channel 114 as shown and described with reference to FIG. 1D. Additionally, the substances contained within and the actions performed using the third channel 316 and the fifth channel 320 may be similar to that of the third channel 116 as shown and described with reference to FIG. 1D.

Figure 4:
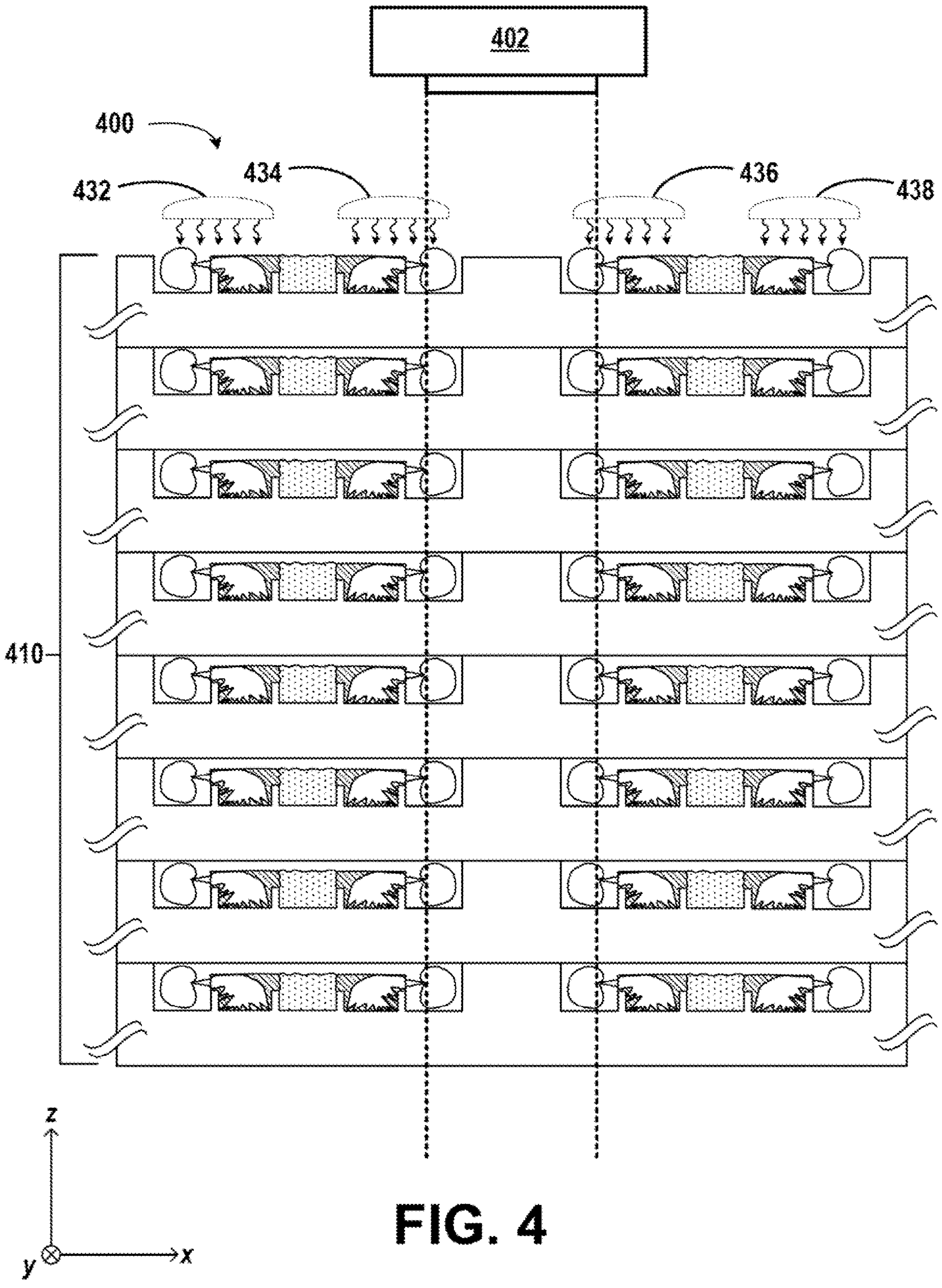
FIG. 4 is a front-view illustration of a multilayer bioreactor tile, according to example embodiments.

FIG. 4 is a front-view illustration (i.e., parallel to the x-z plane, as illustrated) of a bioreactor tile 400. The bioreactor tile 400 may include a plurality of layers 410 (e.g., each layer including a substrate with multiple channels defined therein, similar to the substrate 102 of FIGS. 1A-1D, the substrate 202 of FIG. 2, or the substrate 302 of FIGS. 3A-3C). As such, the bioreactor tile 400 may be referred to as a multi-layer bioreactor tile. Further, the bioreactor tile 400 may include a plurality of optical waveguides (e.g., a first optical waveguide 432, a second optical waveguide 434, a third optical waveguide 436, and a fourth optical waveguide 438). The optical waveguides 432, 434, 436, 438 may direct illumination light to the channels positioned underneath the respective optical waveguides 432, 434, 436, 438. For example, the plant cells, trichomes, gel, liquid nutrient media, and substrate in the various layers 410 may be transparent or substantially translucent, thereby allowing illumination light from the optical waveguides 432, 434, 436, 438 to be provided vertically (e.g., along the z-direction) to all layers 410. Though not labeled with reference numerals (to avoid unnecessary clutter of the drawing), the respective channels in each of the plurality of layers 410 may be providing nutrients, growing plant cells, or housing produced trichomes, as illustrated. Also illustrated in FIG. 4 (though not necessarily a component of the bioreactor tile 400, itself) is a camera 402 positioned above at least some subset of the channels in the plurality of layers 410. The camera 402 may represent one of a plurality of sensors of an associated bioreactor (e.g., the bioreactor 500 shown and described with reference to FIG. 5). The camera 402 may be used only to monitor the bioreactor tile 400 illustrated in FIG. 4 or to monitor multiple bioreactor tiles within the bioreactor (e.g., sequentially or simultaneously).

Each layer within the plurality of layers 410 in the bioreactor tile 400 may be used to produce product (e.g., contained within the trichomes produced in that respective layer). As such, the bioreactor tile 400 may have higher throughput (e.g., production of product per unit volume or per unit time) than the bioreactor tiles 100, 200, 300 illustrated in FIGS. 1A-3C. In some embodiments, each of the layers 410 may be growing the same types of plant cells and producing the same products (e.g., contained within trichomes). However, this need not be the case. In some embodiments, different layers could be growing different plant cells and/or producing different products from one another. Further, in some embodiments, each of the channels that contain the same substances (e.g., within the same layer and/or across multiple layers) may be supplied/controlled together. For example, each of the liquid nutrient media channels in all layers of the bioreactor tile 400 may receive liquid nutrient media from inlets of the respective channels, and each of the inlets of the respective channels may be fed by the same supply (e.g., a tank of a fluid management system of a bioreactor that contains liquid nutrient media) and/or connected to the same pump (e.g., of a fluid management system within a bioreactor, such as the bioreactor 500 shown and described below within reference to FIG. 5). Similarly, outlets of the same types of channels may also be connected. For example, outlets of the product channels may provide harvested trichomes to the same product storage (e.g., product tank of a fluid management system of a bioreactor, such as the bioreactor 500 shown and described below with reference to FIG. 5). Other examples of the various layers being tied to one another are also possible and are contemplated herein. For example, in some embodiments, a bioreactor tile may include one or more separate dilution channels (e.g., one dilution channel per layer, multiple dilution channels per layer, or a single dilution channel for the entire bioreactor tile) that is usable to evaluate the content of a mixture in the tile (e.g., a chemical composition of a liquid nutrient media that is flowed through the dilution channel(s)). It is also understood that in some embodiments (e.g., embodiments where the plant cells being grown and/or the product being produced in the different layers are different) the layers may be operated independently.

The camera 402 may be a component of the bioreactor tile 400 or of a larger bioreactor (e.g., the bioreactor 500 illustrated and described below with reference to FIG. 5), in various embodiments. As illustrated in FIG. 4, the camera 402 may be positioned above the plurality of layers 410. For example, the camera 402 may be positioned above the product channels in an adjacent double-sided arrangements of channels (e.g., based on the product channels being defined within the substrates such that there is sufficient spacing between the product channels in the adjacent double-sided arrangements so as to permit imaging of the trichomes within the product channels). As such, the camera 402 may be configured to capture images (e.g., red-green-blue (RGB) images) of trichomes within the product channels (e.g., both of the trichomes in the product channels in the top bioreactor tile layer and trichomes in lower bioreactor tile layers). In some embodiments, the camera 402 may include one or more lenses or mirrors (e.g., may be integrated within an optical microscope) to capture images at the appropriate scale. Using images captured by the camera 402 (e.g., multiple images captured over time), the maturity state of the trichomes may be monitored. In some embodiments, there may be additional cameras (e.g., placed above additional product channels). Further, in some embodiments, the camera 402 (or additional cameras) may be positioned and configured to capture images of other channels (e.g., the plant cell channels to monitor the growth of the plant cells). While the camera 402 described herein may be an optical camera used to capture RGB images, it is understood that other types of imaging devices (e.g., to monitor the growth of the plant cells and/or trichomes) using other imaging modalities are also possible and are contemplated herein. For example, in some embodiments, the camera 402 may be replaced by or augmented by one or more devices capable of performing hyperspectral imaging, Raman spectroscopy, and/or fluorescence spectroscopy. Other imaging modalities are also possible and are contemplated herein.

Figure 5:
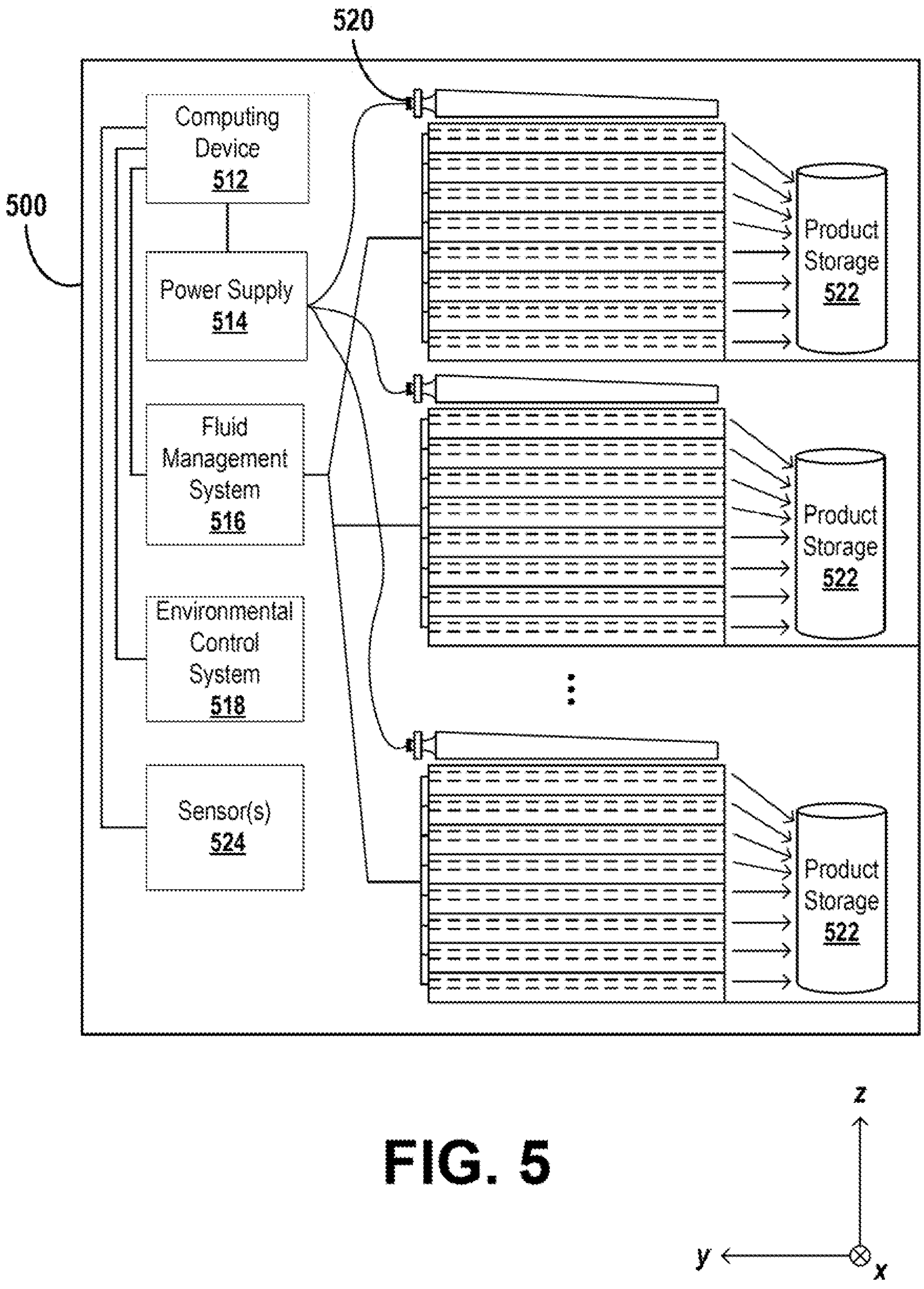
FIG. 5 is a schematic illustration of a bioreactor, according to example embodiments.

FIG. 5 is a schematic illustration of a bioreactor 500, according to example embodiments. The bioreactor 500 may include a housing (e.g., a cabinet) that includes a plurality of bioreactor tiles (e.g., the bioreactor tile 100 illustrated in FIGS. 1A-1D, the bioreactor tile 200 illustrated in FIG. 2, the bioreactor tile 300 illustrated in FIGS. 3A-3C, or the bioreactor tile 400 illustrated in FIG. 4), a computing device 512 (e.g., a controller), a power supply 514, a fluid management system 516, an environmental control system 518, a plurality of illumination sources 520, product storage 522 (e.g., a product storage 522 associated with each bioreactor tile), and one or more sensors 524. For example, there may be a plurality of multi-layer bioreactor tiles (e.g., a plurality of copies of the bioreactor tile 400 illustrated in FIG. 4) that are arranged on various shelves of the bioreactor 500 (e.g., each shelf being individually retractable/removable/swappable in order to swap out bioreactor tiles). It is understood that, in some embodiments, multiple components may be combined. For example, in some embodiments, the power supply 514 and the illumination sources 520 may be combined (e.g., in a single packaged device) to formed an illumination system of the bioreactor 500. Likewise, in some embodiments, the product storage 522 may actually be just one component of the fluid management system 516 (e.g., along with other pumps, tubes, vats, etc.), rather than the fluid management system 516 and the product storage 522 being distinct components.

As illustrated by the three vertical dots in FIG. 5, while only three bioreactor tiles/three product storage 522 are illustrated, it is understood that additional bioreactor tiles/product storage 522 may also be present within the bioreactor 500 (e.g., four bioreactor tiles, five bioreactor tiles, seven bioreactor tiles, eight bioreactor tiles, nine bioreactor tiles, ten bioreactor tiles, sixteen bioreactor tiles, twenty bioreactor tiles, thirty bioreactor tiles, thirty six bioreactor tiles, forty bioreactor tiles, fifty bioreactor tiles, sixty bioreactor tiles, sixty four bioreactor tiles, seventy bioreactor tiles, eighty bioreactor tiles, ninety bioreactor tiles, one hundred bioreactor tiles, one hundred and ten bioreactor tiles, one hundred and twenty bioreactor tiles, one hundred and twenty eight bioreactor tiles, etc.).

The computing device 512 may serve as a controller for one or more components of the bioreactor 500. For example, as illustrated by the lines connected to the computing device 512 (e.g., representing one or more communicative connections, such as wireline connections or wireless connections), the computing device 512 may receive (and possibly store) information from and/or provide instructions to the power supply 514, the fluid management system 516, the environmental control system 518, and/or the sensor(s) 524. In some embodiments, the computing device 512 may also be connected to one or more sensors within one or more of the other components (e.g., sensors that are located within the power supply 514, the fluid management system 516, the environmental control system 518, the illumination sources, or the product storage 522). For example, the computing device 512 may also be connected to one or more sensors within one or more of the product storage 522 (e.g., to monitor an amount of product contained in the one or more product storage 522). In order to perform such tasks, the computing device 512 may execute (e.g., using a processor) instructions stored in a memory (e.g., a non-transitory computer-readable medium). An example computing device 600 is described below with reference to FIG. 6. The computing device 600 may be used as or a component of the computing device 512 illustrated in FIG. 5, in some embodiments. Further, while the computing device 512 is shown as integrated into the bioreactor 500 in FIG. 5, it is understood that other embodiments are also possible and are contemplated herein (e.g., the computing device 512 may be a remote computing device, such as a cloud computing device, that communicates with one or more components of the bioreactor 500 from a remote location, such as over the public Internet, over WiFi, or using BLUETOOTH®).

In some embodiments, the computing device 512 may cause an illumination system to provide illumination light to the plant cells and/or trichomes in the bioreactor tiles. For example, the computing device 512 may cause the power supply 514 to provide power to one or more (e.g., a selected subset) of the illumination sources 520 such that the illumination sources 520 provide illumination light to the plant cells and/or trichomes in the bioreactor tiles (e.g., via optical waveguides of the bioreactor tiles). This may be triggered based on imaging (e.g., optical monitoring using the sensor(s) 524, such as the camera 402 illustrated in FIG. 4, connected to the computing device 512) of the trichomes and/or the plant cells. For example, at a given maturity level of the plant cells, the computing device 512 may cause the power supply 514 to provide power to one or more of the illumination sources 520 in 12 hour increments (e.g., a periodic lighting condition of 12 hours of light followed by 12 hours of darkness). The computing device 512 may also receive feedback from an illumination system (e.g., from the power supply 514 or illumination sources 520) regarding the status of the illumination system. For example, the computing device 512 may receive data from the power supply 514 indicative of power consumption and/or receive data from the illumination sources 520 indicative of illumination power or illumination wavelength.

Likewise, the computing device 512 may cause the fluid management system 516 to supply various fluids (e.g., pressurized air, air mixtures/various gases with predefined concentrations, liquid nutrient media, extractant, etc.) to the bioreactor tiles of the bioreactor 500 (e.g., using one or more pumps, tanks, pipes, tubes, etc. of the fluid management system 516). This may also be triggered based on imaging (e.g., optical monitoring using the sensor(s) 524, such as the camera 402 illustrated in FIG. 4, connected to the computing device 512) of the trichomes and/or the plant cells. For example, at a given maturity level of the trichomes during a production cycle, the computing device 512 may cause the fluid management system 516 to flow extractant through product channels of the bioreactor tiles in order to harvest product from the product channels. The computing device 512 may also receive feedback from the fluid management system 516 regarding the status of the fluid management system 516. For example, the computing device 512 may receive data from the fluid management system 516 indicative of amount of fluid remaining in a given reservoir (e.g., volume of reserve liquid nutrient media remaining within a given tank), indicative of fluid flow rate (e.g., flow rate of one or more fluids being provided to the bioreactor tiles and/or extracted from the bioreactor tiles using one or more tubes/pipes of the fluid management system 516), indicative of valve status (e.g., whether a solenoid within the fluid management system 516 is open or closed), etc.

Similarly, the computing device 512 may cause the environmental control system 518 to modify various aspects of the environment of the bioreactor 500 (e.g., a temperature within a housing of the bioreactor, a humidity within a housing of the bioreactor, an air pressure within a housing of the bioreactor, etc.) using one or more elements of the environmental control system 518 (e.g., a humidifier, a heater, a cooling device, etc.). This may likewise be triggered based on imaging (e.g., optical monitoring using the sensor(s) 524, such as the camera 402 illustrated in FIG. 4, connected to the computing device 512) of the trichomes and/or the plant cells. For example, at a given maturity level of the plant cells during the production cycle (e.g., during a seeding stage of the plant cells or during a growth stage of the plant cells), the computing device 512 may cause the environmental control system 518 to provide a given set of environmental conditions (e.g., predetermined temperature and/or humidity) to foster plant cell growth. Providing a given set of environmental conditions may include providing cycles of certain environmental conditions. For example, the computing device 512 may cause the environmental control system 518 to repeatedly provide a higher temperature for 12 hours followed by a lower temperature for 12 hours during a growth stage of the plant cells (e.g., to mimic natural day/night cycles). The computing device 512 may also receive feedback from the environmental control system 518 regarding the status of the environmental control system 518. For example, the computing device 512 may receive data from the environmental control system 518 indicative of a current temperature and/or humidity being provided by the environmental control system 518.

As illustrated, the computing device 512 of FIG. 5 is connected to and configured to communicate with the power supply 514, the fluid management system 516, the environmental control system 518, and the sensor(s) 524. Additionally, in some embodiments, the computing device 512 may be configured to communicate with computing devices of other bioreactors (e.g., other bioreactors within the same bioreactor facility as the bioreactor 500 and/or in different bioreactor facilities). For example, the computing device 512 may transmit data to and/or receive data from other bioreactors (e.g., over the public Internet, over a local area network (LAN), using WiFi, using cellular communication, using BLUETOOTH®, etc.) in order to optimize the production cycle of the bioreactor 500 (e.g., by comparing the operating parameters/production results of one or more other bioreactors to the operating parameters/production results of the bioreactor 500). Further, the computing device 512 may be configured to communicate with a facility-management server (e.g., as shown and described relative to FIGS. 8A and 8B).

The power supply 514 may be connected to the computing device 512 (e.g., to receive instructions from the computing device 512) and/or to the illumination sources 520 (e.g., as illustrated by the wired connections in FIG. 5 and/or as part of a larger illumination system of the bioreactor 500). In some embodiments, the power supply 514 may include a capacitor, a battery, a connection to an external power supply (e.g., via a wall outlet), a generator, a converter/rectifier (e.g., to convert from an alternating current (AC) to a direct current (DC) power supply), etc. The power supply 514 (e.g., as part of an illumination system of the bioreactor 500) may also include one or more switches (e.g., transistors) capable of selecting a subset of illumination sources 520 within the bioreactor 500 to which to apply power. In this way, the power supply 514 can cause subsets of the illumination sources 520 to selectively provide illumination light to the respective bioreactor tiles.

The fluid management system 516 may include one or more fluid supplies (e.g., tanks including fluid mixtures and/or tanks including single fluid components which can be mixed by the fluid management system 516 to generated fluid mixtures). Such fluid supplies may be connected to the channels of the bioreactor tiles (e.g., to inlets of the channels of the bioreactor tiles), which is illustrated in FIG. 5 by the lines connecting the fluid management system 516 to the channels of the bioreactor tiles. The fluid supplies may be connected to the channels of the bioreactor tiles via tubing, pipes, or other fluid lines. In some embodiments, the fluid management system 516 may also include one or more valves (e.g., solenoids or pneumatic valves) usable to open and/or close the respective fluidic connections between the fluid supplies and the bioreactor tiles. In this way, the fluid management system 516 can select a subset of the bioreactor tiles (or even, in some embodiments, a subset of the layers across all bioreactor tiles or, even further, specific channels across all bioreactor tiles) to receive certain fluids (e.g., liquid nutrient media, extractant, cellular precursor, etc.). Still further, in some embodiments, the fluid management system 516 may include one or more pumps (e.g., plunger pumps, diaphragm pumps, piston pumps, hydraulic pumps, peristaltic pumps, rotary vane pumps, screw pumps, gear pumps, etc.) used to cause fluid to flow from the fluid supplies to the bioreactor tiles and/or to force fluid out of the bioreactor tiles into the product storage 522. Additionally or alternatively, in some embodiments, one or more components of the fluid management system 516 may include one or more mass flow controllers (e.g., to measure how much fluid has passed through a certain component of the fluid management system 516). As described above, measurements from sensors internal to the fluid management system 516 (e.g., the one or more mass flow controllers) may be communicated to the computing device 512 in order for the computing device 512 to make control determinations, for example. It is understood that the fluid management system 516 may include other devices, as well, that are configured to assist in providing fluids to the bioreactor tiles, retrieving fluids from the bioreactor tiles, and/or processing fluids prior to or after the fluids have interacted with the bioreactor tiles. For example, the fluid management system 516 could include reservoirs or tanks to store fluids, centrifuges used to separate plant/trichome matter from product produced by trichomes (e.g., in order to purify the product after retrieving the product from one or more bioreactor tiles in the bioreactor 500), one or more metal screens used to obtain the trichomes (e.g., used to separate extractant that is used to harvest the trichomes from the trichomes themselves), and/or one or more evaporators (e.g., falling-film evaporators, wiped-film evaporators, rotary evaporators, etc.) combined with one or more boilers to extract the product (e.g., by separating an extractant used to harvest the trichomes, such as ethanol, butane, or carbon dioxide, from the oil-based product, such as by boiling off and recollecting the extractant for future use at a temperature that is below the boiler point of the oil-based product).

The environmental control system 518 may include one or more heating or cooling devices. Such heating or cooling devices may be controlled by the computing device 512, for example, in order to maintain appropriate environmental conditions within the bioreactor 500 (e.g., appropriate environmental conditions to grow plant cells and/or cause the plant cells to produce trichomes). Additionally or alternatively, in some embodiments, the environmental control system 518 may include a temperature sensor (e.g., a thermometer) configured to measure a current temperature within the bioreactor 500, as a whole, or within one specific region of the bioreactor 500 (e.g., within one of the bioreactor tiles). The temperature sensor may provide temperature measurements to the computing device 512 so the computing device 512 can make control decisions for the bioreactor 500 based on the given temperature within the bioreactor 500/within a given region of the bioreactor 500. Other sensors are also possible within the environmental control system 518 (e.g., humidity sensors) and are contemplated herein. Still further, in some embodiments, the environmental control system 518 may include one or more humidifiers (e.g., configured to be controlled by the computing device 512 so as to maintain the humidity around one or more of the bioreactor tiles or around specific channels within one or more of the bioreactor tiles) or other devices configured to modify environmental conditions within the bioreactor 500.

The illumination sources 520 (e.g., as part of a larger illumination system that includes other components, such as the power supply 514) may provide illumination light to the optical waveguides of the bioreactor tiles in the bioreactor 500 (e.g., when supplied with power from the power supply 514). In some embodiments, the illumination sources 520 may include one or more LEDs, light bulbs, lasers, etc. Wavelengths for the illumination light produced by the illumination sources 520 may be within a range usable for photosynthesis within plant cells in the bioreactor tiles, for example. Additionally, in some embodiments, the illumination sources 520 may produce a wide range of wavelengths, from which one or more optical filters selects a narrower range of wavelengths to provide to the optical waveguides in the bioreactor tiles. Further, in some embodiments, the illumination sources 520 may be located far enough from the bioreactor tiles within the bioreactor 500 so as not to cause heating that adversely affects the environmental conditions within the channels of the bioreactor tiles. In some embodiments, illumination light from the illumination sources 520 may be coupled to the optical waveguides of the bioreactor tiles using free-space coupling. However, it is understood that other optical coupling methods are also possible and are contemplated herein. For example, one or more Bragg gratings, one or more lenses, one or more mirrors, one or more optical fibers, etc. may be used to couple the illumination light from the illumination sources 520 into the respective optical waveguides.

The product storage 522 may include one or more tanks configured to store the product generated by the bioreactor tiles (e.g., generated by trichomes in the bioreactor tiles and extracted from the bioreactor tiles upon the trichomes reaching maturity) and/or used liquid nutrient media/plant cell and gel mixtures from the bioreactor tiles. In some embodiments, one or more fluidic connections (e.g., pipes, tubes, fluid lines, etc.) may connect one or more of the channels in the respective bioreactor tiles to the product storage 522. While a product storage 522 is illustrated in FIG. 5 as corresponding to each bioreactor tile in the bioreactor 500, it is understood that each product storage 522 may represent a series of tanks/containers (e.g., one tank corresponding to product from the respective bioreactor tile and one tank corresponding to used liquid nutrient media). It is also understood that, in other embodiments, other arrangements are also possible. For example, a single product storage may be shared by multiple bioreactor tiles (e.g., all bioreactor tiles within the bioreactor 500). Alternatively, in some embodiments, the bioreactor 500 may not include product storage, at all. In such embodiments, product produced using the bioreactor tiles may instead be stored within a product storage of a bioreactor facility (e.g., within the facility-wide fluid management system 830 of the bioreactor facility 800 shown and described below with reference to FIG. 8A).

As described above, the one or more sensors 524 may provide data to the computing device 512 regarding one or more conditions of the bioreactor 500. The one or more sensors 524 may communicate with the computing device 512 using a wireline interface and/or wirelessly. This data may be used by the computing device 512 to make control decisions for the bioreactor 500. Such control decisions may result in the computing device 512 providing one or more operating parameters to one or more of the components of the bioreactor 500. For example, the computing device 512 may provide one or more operating parameters to an illumination system of the bioreactor 500 (e.g., an illumination system that includes the power supply 514 and the illumination sources 520), the fluid management system 516, the environmental control system 518, etc. Further, providing one or more operating parameters to one or more of the components of the bioreactor 500 may include providing operating parameters to one or more of the components of the bioreactor 500 that cause the one or more components to change conditions within the bioreactor 500 (e.g., temperature, humidity, illumination schedule, illumination intensity, illumination wavelength(s), flow rate, liquid nutrient media composition, etc.). The sensor(s) 524 may include a variety of different sensors positioned in a variety of locations within the bioreactor 500 (e.g., within a housing of the bioreactor 500). For example, the sensor(s) 524 may include one or more temperature sensors, one or more humidity sensors, one or more mass flow controllers, one or more flow sensors, one or more pH sensors, one or more air pressure sensors, one or more cameras (or other imaging sensors/light sensors, such as Raman spectroscopy sensors, hyperspectral imaging sensors, fluorescence spectroscopy sensors, optical microscopes, etc., configured to capture an image or other representation of cells or other components of the bioreactor 500), one or more voltmeters, one or more ammeters, volume meter, etc. Further, the sensor(s) 524 may positioned near or on one or more of the bioreactor tiles. Additionally or alternatively, the sensor(s) 524 may be positioned near, on, or within other components of the bioreactor 500 (e.g., inside pipes/tubing of the fluid management system 516, inside valves of the fluid management system 516, near illumination sources 520, etc.). Further, in some embodiments, the sensor(s) 524 may be fixed within the housing of the bioreactor 500, which in other embodiments the sensor(s) 524 may be movable within the housing of the bioreactor 500 and/or removable from the bioreactor 500.

Figure 6:
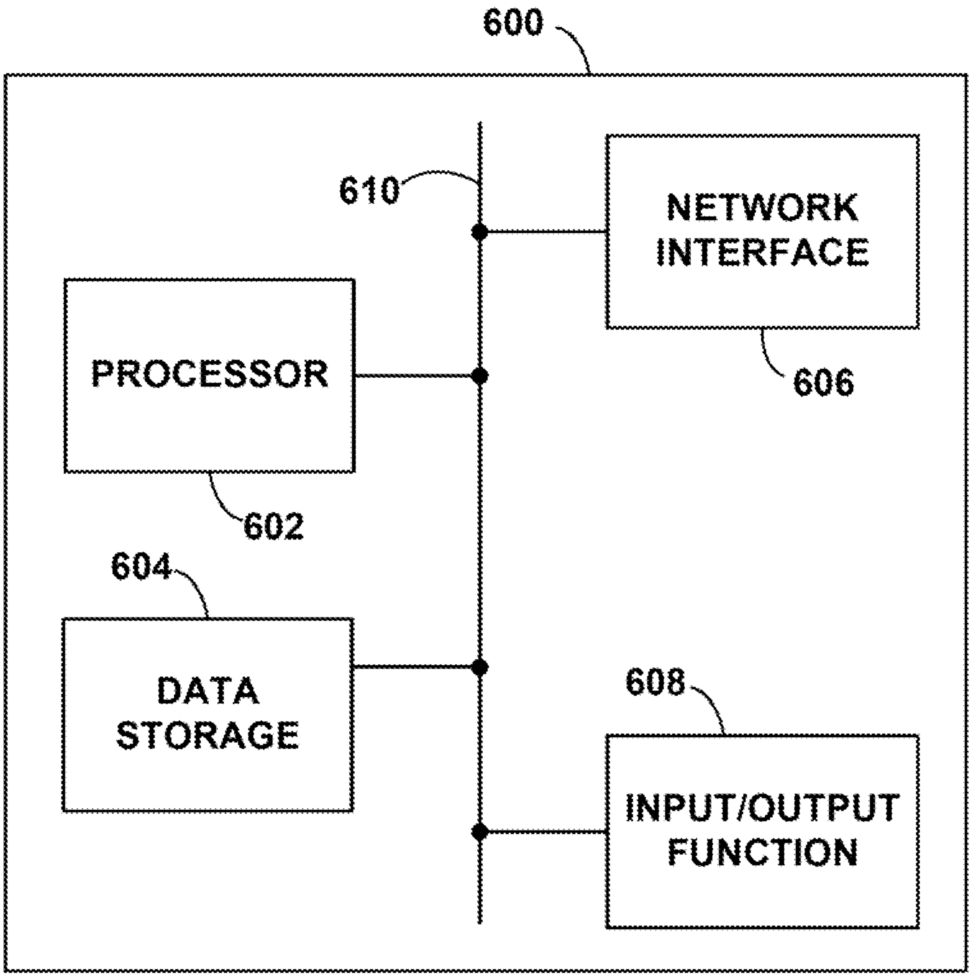
FIG. 6 is a schematic illustration of a computing device, according to example embodiments.

FIG. 6 is a simplified block diagram exemplifying a computing device 600 (e.g., the computing device 512 illustrated and described above with respect to FIG. 5), illustrating some of the functional components that could be included in a computing device arranged to operate in accordance with the embodiments herein. Example computing device 600 could be a client device, a server device, or some other type of computational platform.

In this example, computing device 600 includes a processor 602, a data storage 604, a network interface 606, and an input/output function 608, all of which may be coupled by a system bus 610 or a similar mechanism. Processor 602 can include one or more CPUs, such as one or more general purpose processors and/or one or more dedicated processors (e.g., application specific integrated circuits (ASICs), digital signal processors (DSPs), network processors, etc.).

Data storage 604, in turn, may include volatile and/or non-volatile data storage devices and can be integrated in whole or in part with processor 602. Data storage 604 can hold program instructions, executable by processor 602, and data that may be manipulated by such program instructions to carry out the various methods, processes, or operations described herein. Alternatively, these methods, processes, or operations can be defined by hardware, firmware, and/or any combination of hardware, firmware, and software. By way of example, the data in data storage 604 may contain program instructions, perhaps stored on a non-transitory, computer-readable medium, executable by processor 602 to carry out any of the methods, processes, or operations disclosed in this specification or the accompanying drawings. The data storage 604 may include non-volatile memory (e.g., a read-only memory, ROM) and/or volatile memory (e.g., random-access memory, RAM), in various embodiments. For example, the data storage 604 may include a hard drive (e.g., hard disk), flash memory, a solid-state drive (SSD), electrically erasable programmable read-only memory (EEPROM), dynamic random-access memory (DRAM), and/or static random-access memory (SRAM). It will be understood that other types of transitory or non-transitory data storage devices are possible and contemplated within the scope of the present disclosure.

Network interface 606 may take the form of a wireline connection, such as an Ethernet, Token Ring, or T-carrier connection. Network interface 606 may also take the form of a wireless connection, such as IEEE 802.11 (WiFi), BLUETOOTH®, BLUETOOTH LOW ENERGY (BLE)®, or a wide-area wireless connection. However, other forms of physical layer connections and other types of standard or proprietary communication protocols may be used over network interface 606. Furthermore, network interface 206 may include multiple physical interfaces.

Input/output function 608 may facilitate user interaction with example computing device 600. Input/output function 608 may comprise multiple types of input devices, such as a keyboard, a mouse, a touch screen, and so on. Similarly, input/output function 608 may include multiple types of output devices, such as a screen, monitor, printer, or one or more light emitting diodes (LEDs). Additionally or alternatively, example computing device 600 may support remote access from another device, via network interface 606 or via another interface (not shown), such as a universal serial bus (USB) or high-definition multimedia interface (HDMI) port.

In some embodiments, one or more computing devices may be deployed in a networked architecture. The exact physical location, connectivity, and configuration of the computing devices may be unknown and/or unimportant to client devices. Accordingly, the computing devices may be referred to as "cloud-based" devices that may be housed at various remote locations.

Figure 7:
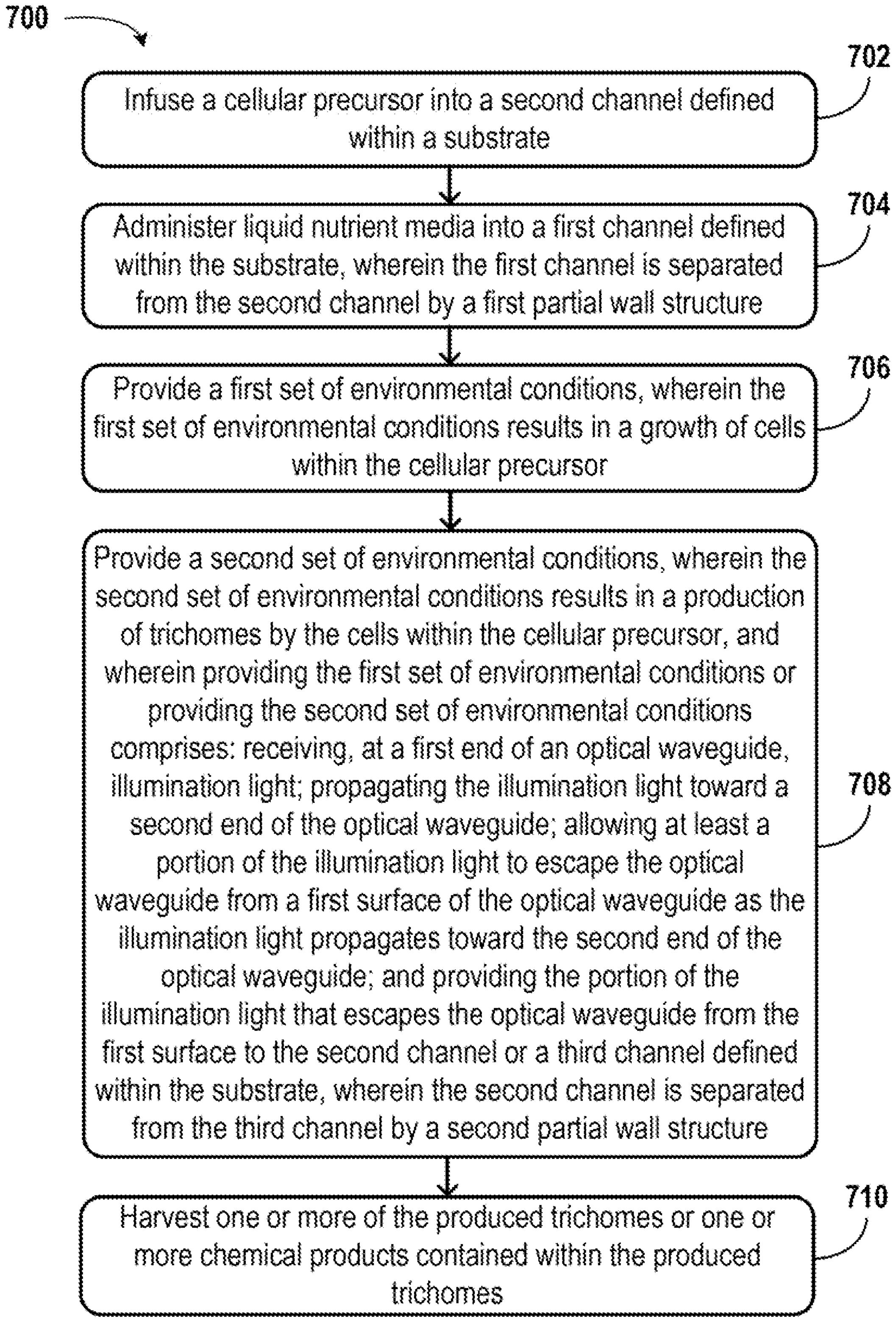
FIG. 7 is a flowchart illustrating a method, according to example embodiments.

FIG. 7 is a flowchart diagram of a method 700, according to example embodiments. The method 700 may be used to grow and harvest trichome cells (e.g., using the bioreactor tile 100 illustrated in FIGS. 1A-1D, the bioreactor tile 200 illustrated in FIG. 2, the bioreactor tile 300 illustrated in FIGS. 3A-3C, the bioreactor tile 400 illustrated in FIG. 4, or the bioreactor 500 illustrated in FIG. 5).

At block 702, the method 700 may include infusing a cellular precursor into a second channel defined within a substrate.

At block 704, the method 700 may include administering liquid nutrient media into a first channel defined within the substrate. The first channel may be separated from the second channel by a first partial wall structure.

At block 706, the method 700 may include providing a first set of environmental conditions. The first set of environmental conditions may result in a growth of cells within the cellular precursor.

At block 708, the method 700 may include providing a second set of environmental conditions. The second set of environmental conditions may result in a production of trichomes by the cells within the cellular precursor. Providing the first set of environmental conditions or providing the second set of environmental conditions may include receiving, at a first end of an optical waveguide, illumination light; propagating the illumination light toward a second end of the optical waveguide; allowing at least a portion of the illumination light to escape the optical waveguide from a first surface of the optical waveguide as the illumination light propagates toward the second end of the optical waveguide; and providing the portion of the illumination light that escapes the optical waveguide from the first surface to the second channel or a third channel defined within the substrate. The second channel may be separated from the third channel by a second partial wall structure.

At block 710, the method 700 may include harvesting one or more of the produced trichomes or one or more chemical products contained within the produced trichomes.

In some embodiments, the method 700 may include performing a sterilization procedure. The sterilization procedure may include heating the substrate or the optical waveguide to a first predetermined temperature for a first predetermined time period. The sterilization procedure may also include cooling the substrate or the optical waveguide to a second predetermined temperature. In some embodiments, the first predetermined temperature may be between 175° C. and 185° C. Further, the second predetermined temperature may be between 20° C. and 25° C.

In some embodiments, the method 700 may include monitoring the growth of cells within the cellular precursor or monitoring the production of trichomes by the cells within the cellular precursor using one or more imaging modalities. The one or more imaging modalities may include capturing one or more red-green-blue (RGB) images using an optical microscope, performing hyperspectral imaging, performing Raman spectroscopy, or performing fluorescence spectroscopy.

In some embodiments of the method 700, the cellular precursor may include a gel precursor media. A gel of the gel precursor media may include agar gel, agarose gel, alginate gel, gelatin gel, acrylamide gel, silica gel, or cellulose gel. The cells within the cellular precursor may include protoplast cell cultures, suspension cell cultures, or micro-calli cell cultures. Further, in some embodiments, infusing the cellular precursor may include waiting a predetermined amount of time for the gel of the gel precursor media to solidify. For example, the predetermined amount of time may be between 0.25 hours and 2.0 hours.

In some embodiments of the method 700, providing the first set of environmental conditions may include providing a temperature of between 20° C. and 25° C. to the second channel or the third channel. Providing the first set of environmental conditions may also include providing the portion of the illumination light that escapes the optical waveguide from the first surface to the second channel or third channel for about 16 hours. Further, providing the first set of environmental conditions may include providing no illumination light to the second channel or third channel for about 8 hours (e.g., providing the first set of environmental conditions may include a periodic administration of illumination light that includes cycles of about 16 hours of illumination light followed by about 8 hours of darkness). Additionally, providing the first set of environmental conditions may include providing a calli-induction media into the first channel.

In some embodiments of the method 700, providing the second set of environmental conditions may include providing a temperature of between 20° C. and 25° C. to the second channel or the third channel. Providing the second set of environmental conditions may also include providing the portion of the illumination light that escapes the optical waveguide from the first surface to the second channel or third channel for about 12 hours. Further, providing the second set of environmental conditions may include providing no illumination light to the second channel or third channel for about 12 hours (e.g., providing the first set of environmental conditions may include a periodic administration of illumination light that includes cycles of about 12 hours of illumination light followed by about 12 hours of darkness). Additionally, providing the second set of environmental conditions may include providing a trichome-induction media into the first channel.

In some embodiments of the method 700, harvesting the one or more trichomes or the one or more chemical products contained within the produced trichomes may include providing a temperature of less than 4° C. to the second channel or the third channel. Harvesting the one or more trichomes or the one or more chemical products contained within the produced trichomes may also include providing no illumination light to the second channel or third channel. Further, harvesting the one or more trichomes or the one or more chemical products contained within the produced trichomes may include flowing low-temperature extractant through the third channel at a sufficient flow rate so as to shear the one or more trichomes from the cells within the cellular precursor. In some embodiments, the low-temperature extractant may include ethanol at a temperature of between −75° C. and 0° C.

Figure 8A:
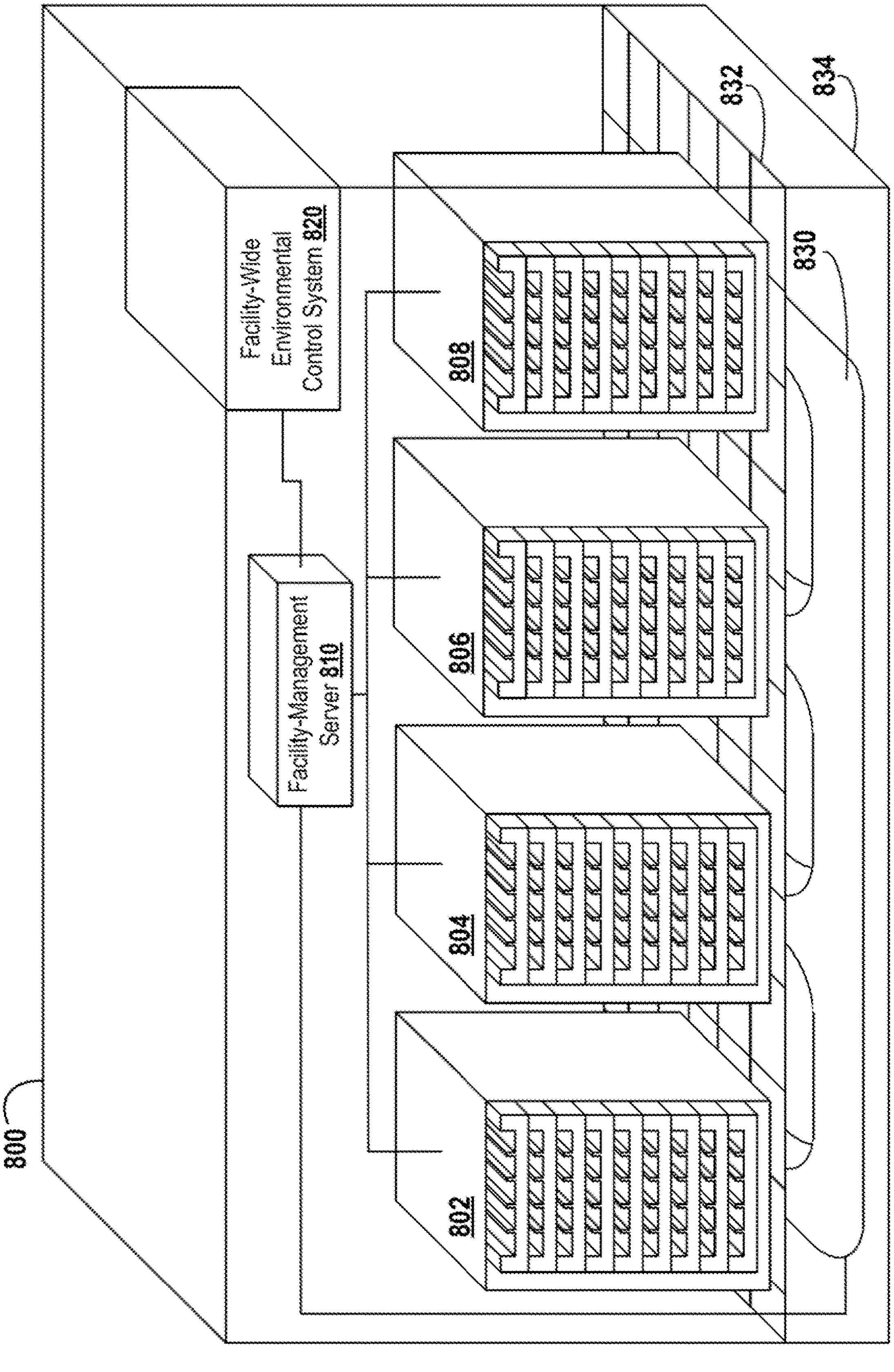
FIG. 8A is an illustration of a system, according to example embodiments.
Figure 8B:
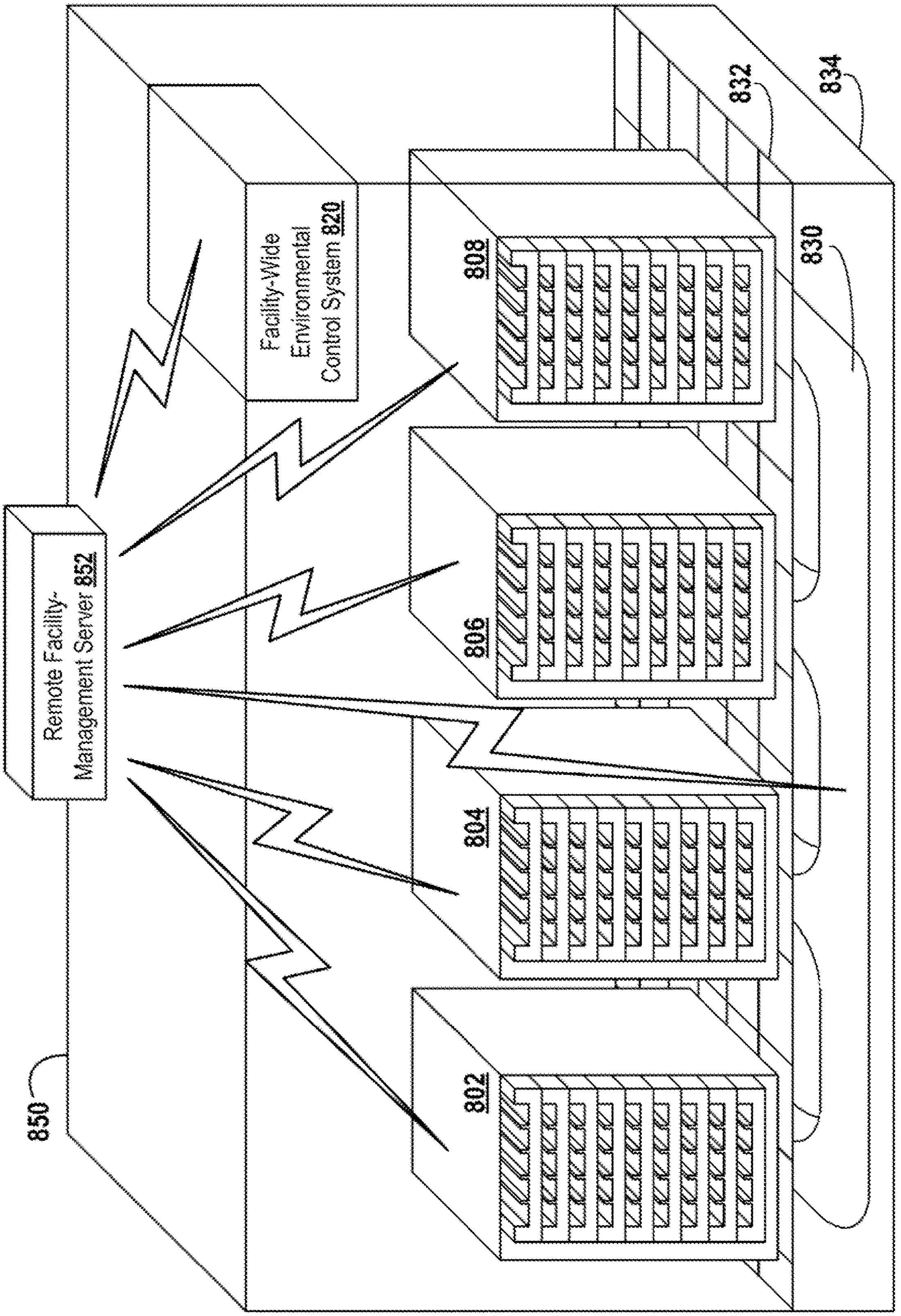
FIG. 8B is an illustration of a system, according to example embodiments.

FIG. 8A is an illustration of a system, according to example embodiments. The system may include a bioreactor facility 800. The bioreactor facility 800 may include a housing. For example, the bioreactor facility 800 may include a warehouse in which all of the other components of the bioreactor facility 800 are located. It is understood that other embodiments are also possible and are contemplated herein (e.g., the system may include multiple bioreactor facilities or multiple bioreactors not contained within bioreactor facilities). As illustrated, the bioreactor facility 800 may include a plurality of bioreactors 802, 804, 806, 808 (e.g., a first bioreactor 802, a second bioreactor 804, a third bioreactor 806, and a fourth bioreactor 808), a facility-management server 810, an environmental control system 820 (e.g., a facility-wide environmental control system 820), and fluid management system 830 (e.g., a facility-wide fluid management system 830) that is at least partially positioned between a floor surface 832 and a subfloor surface 834. Though only four bioreactors 802, 804, 806, 808 are illustrated in FIG. 8A, it is understood that this is provided solely as an example and that other numbers of bioreactors within the bioreactor facility 800 are also possible and are contemplated herein (e.g., one bioreactor, two bioreactors, three bioreactors, five bioreactors, six bioreactors, seven bioreactors, eight bioreactors, nine bioreactors, ten bioreactors, etc.).

Each of the bioreactors 802, 804, 806, 808 illustrated in FIG. 8A may be similar to the bioreactor 500 illustrated in FIG. 5. For example, each of the bioreactors 802, 804, 806, 808 may include a controller (e.g., the computing device 512), an illumination system (e.g., the power supply 514 and the illumination sources 520), a fluid management system (e.g., the fluid management system 516 and the product storage 522), an environmental control system (e.g., the environmental control system 518), and one or more sensors (e.g., sensor(s) 524). Additionally, as illustrated in FIG. 5A, each of the bioreactors 802, 804, 806, 808 may include a series of bioreactor tiles. Such bioreactor tiles may be vertically stack with respect to one another within a housing of the respective bioreactor (e.g., as illustrated in FIGS. 5 and 8A) or may be arranged horizontally adjacent to one another within a housing of the respective bioreactor. Other shapes and/or relative orientations of the bioreactor tiles are also possible and are contemplated herein.

The bioreactors 802, 804, 806, 808 may each simultaneously or sequentially execute production cycles to growth cells and harvest products (e.g., by growing parenchymal plant cells, producing trichomes from the parenchymal cells, and then retrieving products from the trichomes). Further, in some embodiments, each of the bioreactors 802, 804, 806, 808 may be used to grow the same species of cells/produce the same products. However, this need not be the case. In other embodiments, different bioreactors 802, 804, 806, 808 may be used to grow different species of cells and/or produce different products. Still further, in some embodiments, different bioreactor tiles within a single respective bioreactor 802, 804, 806, 808 or across different bioreactors 802, 804, 806, 808 may be used to grow different species of cells/produce different products.

Additionally or alternatively, the bioreactor tiles in each of the bioreactors 802, 804, 806, 808 may include identical layouts and dimensions to one another (e.g., including one or more inlets configured to receive one or more fluids, one or more outlets configured to provide one or more chemical products, and one or more optics configured to receive illumination light). In other embodiments, the bioreactor tiles in the respective bioreactors 802, 804, 806, 808 may have different dimensions/layouts from one another (e.g., to accommodate different cell species being grown in the respective bioreactors 802, 804, 806, 808). Still further, in some embodiments, some bioreactor tiles within a single bioreactor (e.g., bioreactor 802) may have different layouts and/or dimensions than other bioreactor tiles within that bioreactor. This may allow a single bioreactor to be used to execute production cycles on a variety of different cell species (e.g., simultaneously or sequentially). This may also allow for some tiles to be used as monitoring tiles (e.g., optimization tiles) while others are used as production tiles (e.g., tiles used to grow cells and/or produce product). The monitoring tiles may receive fluids (e.g., from a fluid management system of the respective bioreactor) and/or illumination light (e.g., from an illumination system of the respective bioreactor) and may include sensors to monitor the fluids and/or illumination light. However, the monitoring tiles, unlike the production tiles, may not house cells and may not be used to produce product. Instead, the monitoring tiles may provide data (e.g., conditions measured by one or more sensors associated with the monitoring tiles) to a computing device (e.g., controller) of the bioreactor. The computing device may then use the data from the monitoring tiles to inform control decisions about how to manage the production tiles (e.g., how to set operating parameters about one or more of the production tiles).

As illustrated by the connection in FIG. 8A, the bioreactors 802, 804, 806, 808 (e.g., the computing devices of each respective bioreactor) may be configured to communicate with the facility-management server 810. Communicating with the facility-management server 810 may allow the bioreactors 802, 804, 806, 808 to provide data related to conditions of the respective bioreactors 802, 804, 806, 808 (e.g., conditions sensed by one or more sensors of the respective bioreactors 802, 804, 806, 808) to the facility-management server 810 and/or to receive instructions (e.g., that provide operating parameters for the respective bioreactors 802, 804, 806, 808) from the facility-management server 810. In some embodiments, the respective bioreactors 802, 804, 806, 808 may also be configured to communicate with one another or with other components in the bioreactor facility 800 (e.g., with a controller of the facility-wide environmental control system 820 or a controller of the facility-wide fluid management system 830).

Further, each of the bioreactors 802, 804, 806, 808 may exchange fluids with the facility-wide fluid management system 830. For example, liquid nutrient media may be provided to one or more bioreactor tiles of the bioreactors 802, 804, 806, 808. This liquid nutrient media may be partially or wholly supplied to the respective bioreactors by the facility-wide fluid management system 830. Similarly, trichomes housed within bioreactor tiles of the bioreactors 802, 804, 806, 808 may produce products (e.g., cannabidiol oil). Such products may then be removed from the bioreactors 802, 804, 806, 808 by the facility-wide fluid management system 830 and stored (e.g., within a storage tank of the facility-wide fluid managements system 830). It is understood that these fluids are provided solely as an example and that the facility-wide fluid management system 830 may exchange other fluids with the facility-wide fluid management system 830 (e.g., pressurized gases, air mixtures, sterilization/cleaning solutions, sterilization/cleaning gases, etc.).

The facility-management server 810 may communicate with other components in the bioreactor facility 800. For example, the facility-management server 810 may communicate with each of the bioreactors 802, 804, 806, 808, the facility-wide environmental control system 820, and/or the facility-wide fluid management system 830. Communicating with the various components of the bioreactor facility 800 may include receiving data from the respective components (e.g., data relating to conditions of the respective components) or providing instructions (e.g., operating parameters) to the respective components. For example, the facility-management server 810 may instruct one or more of the bioreactors 802, 804, 806, 808 to begin a production cycle, to move onto the next phase of a production cycle, to modify one or more environmental conditions within the respective bioreactor, to modify one or more flow rates of one or more fluids in the respective bioreactor, to modify an illumination schedule in the respective bioreactor, to modify an illumination intensity within the respective bioreactor, to modify an illumination wavelength within the respective bioreactor, etc.

The facility-management server 810 may provide instructions to the other components of the bioreactor facility 800 based on one or more control decisions made by the facility-management server 810. For example, the facility-management server 810 may receive one or more conditions from one or more sensors of one or more of the bioreactors 802, 804, 806, 808. Then, based on those conditions, the facility-management server 810 may determine operating parameters (e.g., one or more revised operating parameters) for one or more of the bioreactors 802, 804, 806, 808 and provide instructions to the one or more bioreactors 802, 804, 806, 808 based on the operating parameters. Additionally or alternatively, the facility-management server 810 may determine operating parameters for components of the facility, at large, such as for the facility-wide environmental control system 820 or the facility-wide fluid management system 830. Still further, the facility-management server 810 may receive data from and/or make determinations based on data from sensors of components of the facility, at large, such as the facility-wide environmental control system 820 or the facility-wide fluid management system 830.

In order to communicate with other components, make control decisions, and provide instructions to the other components, the facility-management server 810 may include a computing device (e.g., the computing device 600 illustrated in FIG. 6). As illustrated in FIG. 8A, the facility-management server 810 may be an on-site computing device (e.g., a computing device located within the bioreactor facility 800). In other embodiments, though, the facility-management server may instead be located remotely from the bioreactor facility. For example, FIG. 88 illustrates a bioreactor facility 850 that includes a remote facility-management server 852. The remote facility-management server 852 may include a cloud server, for example. Whether a facility-management server is on-site or remotely located, though, the facility-management server may still be configured to communicate with the components of the bioreactor facility. In some embodiments, the remote facility-management server 852 illustrated in FIG. 8B may communicate with the components of the bioreactor facility 850 over the public Internet, for example, while the facility-management server 810 illustrated in FIG. 8A may communicate with the components of the bioreactor facility 800 using a wireline interface or over a LAN, BLUETOOTH®, WiFi, etc.

The facility-wide environmental control system 820 may include one or more devices configured to control the climate of the entire bioreactor facility 800 (e.g., the temperature, humidity, air pressure, etc. of the bioreactor facility 800). Such devices may be in a single central location within the bioreactor facility 800 or spread out across the bioreactor facility 800. As illustrated by the connection in FIG. 8A, the facility-wide environmental control system 820 may be configured to communicate to the facility-management server 810 to provide data related to conditions of bioreactor facility 800 to the facility-management server 810 and/or to receive instructions (e.g., that provide operating parameters for the facility-wide environmental control system 820) from the facility-management server 810. Communications between the facility-wide environmental control system 820 and the facility-management server 810 may take place over a wireline interface and/or wirelessly (e.g., over WiFi or BLUETOOTH®). The facility-wide environmental control system 820 may be configured to provide the bioreactors 802, 804, 806, 808 with one or more sets of external environmental conditions. Such external environmental conditions may be augmented by environmental control systems (e.g., the environmental control system 518 illustrated in FIG. 5) to provide environmental conditions to the bioreactor tiles of the bioreactors 802, 804, 806, 808 to support growth of the cells and/or production of trichomes. For example, the facility-wide environmental control system 820 may provide a given temperature within the bioreactor facility 800 as an external temperature for the bioreactors 802, 804, 806, 808 and a heater/cooler within the environmental control system 518 may modify the external temperature for the bioreactors 802, 804, 806, 808 to provide an internal operating temperature for the bioreactors 802, 804, 806, 808 (e.g., to be used by the bioreactor tiles in the respective bioreactors 802, 804, 806, 808).

The facility-wide fluid management system 830 may include one or more components configured to supply fluids to and/or retrieve fluids from the bioreactors 802, 804, 806, 808 that are used for operation of the bioreactors 802, 804, 806, 808 and/or produced by the bioreactors 802, 804, 806, 808 (e.g., fluids that contain products produced by trichomes housed within bioreactor tiles of the bioreactors 802, 804, 806, 808). For example, the facility-wide fluid management system 830 may include valves, pipes, tubes, pressurizers, pumps, etc. Further, in some embodiments, the facility-wide fluid management system 830 may include one or more components configured to store and/or process fluids. For example, the facility-wide fluid management system 830 may include tanks, vats, mixers, centrifuges, chambers, reservoirs, etc.

As illustrated in FIGS. 8A, the bioreactor facility 800 may include a floor surface 832 and a subfloor surface 834. As also illustrated in FIG. 8A, in some embodiments, one or more parts of the facility-wide fluid management system 830 may be located between the floor surface 832 and the subfloor surface 834. For example, tanks may be located between the floor surface 832 and the subfloor surface 834 that store liquid nutrient media or product retrieved from the bioreactors 802, 804, 806, 808. Likewise, pumps and/or pipes may be located between the floor surface 832 and the subfloor surface 834. By locating one or more parts of the facility-wide fluid management system 830 between the floor surface 832 and the subfloor surface 834, fluid exchange between one or more components of the bioreactor facility 800 may occur without requiring additional space between the bioreactors 802, 804, 806, 808 to be occupied with pipes, tanks, pumps, valves, etc. It is understood that the arrangements of FIGS. 8A and 8B, however, are provided solely as non-limiting examples and that other embodiments are also possible. For example, in some embodiments additional components of the bioreactor facility 800 may be positioned beneath the floor surface 832 (e.g., parts of the facility-wide environmental control system 820, the facility-management server 810, electrical connections/communicative connections to the bioreactors 802, 804, 806, 808, etc. could be located beneath the floor surface 832 and above the subfloor surface 834). Alternatively, in some embodiments, there may only exist a floor surface and no subfloor surface. In such embodiments, the components of the facility-wide fluid management system 830 may be positioned above the floor surface.

In some embodiments, the bioreactor facility 800 may include additional components not illustrated in FIG. 8A. For example, in addition to the bioreactors 802, 804, 806, 808, the facility-management server 810, and the facility-wide environmental control system 820, the bioreactor facility 800 may include one or more sensors that can be used to diagnose one or more issues with a bioreactor 802, 804, 806, 808. While each of the bioreactors 802, 804, 806, 808 may include respective sensors (e.g., as shown and described relative to FIG. 5), there may be detachable sensors that can be moved from one bioreactor to another. For example, in some embodiments, monitoring lighting conditions may only be necessary for certain portions of the production cycle. Hence, at any given point in time, only one of the four bioreactors 802, 804, 806, 808 may need to use an optical sensor. Rather than have multiple optical sensors across all bioreactors 802, 804, 806, 808, a single optical sensor may be interchanged between among the bioreactors 802, 804, 806, 808 so as to provide sensing capabilities only when needed. This may reduce the volume required for a given bioreactor 802, 804, 806, 808 and/or reduce the materials used to produce a given bioreactor 802, 804, 806, 808.

Figures 9A, 9B, 9C, 9D:
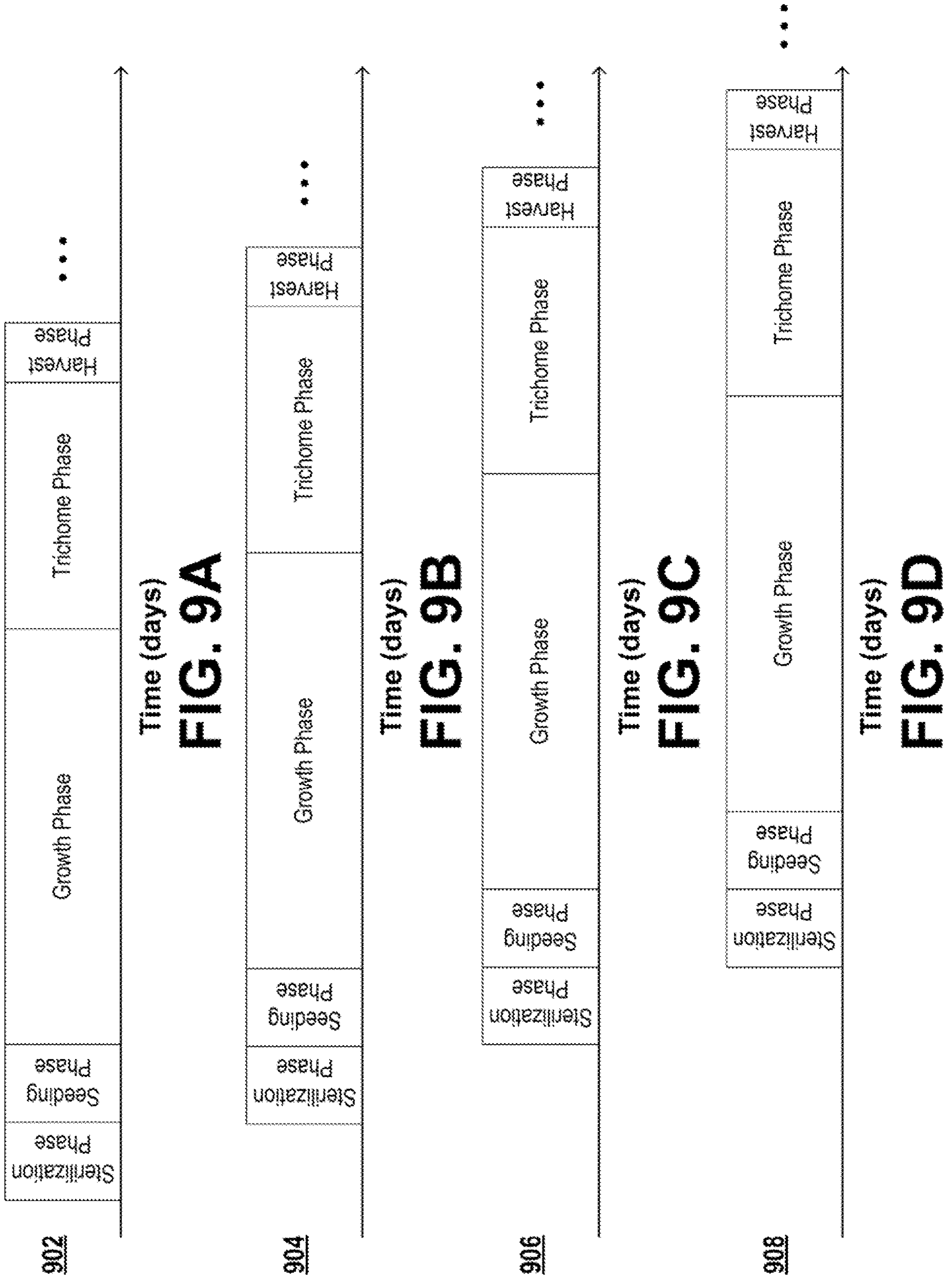
FIG. 9A is an illustration of a production cycle of a bioreactor, according to example embodiments.
FIG. 9B is an illustration of a production cycle of a bioreactor, according to example embodiments.
FIG. 9C is an illustration of a production cycle of a bioreactor, according to example embodiments.
FIG. 9D is an illustration of a production cycle of a bioreactor, according to example embodiments.

FIGS. 9A-9D illustrate production cycles of bioreactors over time (e.g., measured in days). For example, FIG. 9A illustrates a production cycle 902 of a first bioreactor in a bioreactor facility (e.g., bioreactor 802 illustrated and described with reference to FIG. 8A). Similarly, FIG. 9B illustrates a production cycle 904 of a second bioreactor in a bioreactor facility (e.g., bioreactor 804 illustrated and described with reference to FIG. 8A), FIG. 9C illustrates a production cycle 906 of a third bioreactor in a bioreactor facility (e.g., bioreactor 806 illustrated and described with reference to FIG. 8A), and FIG. 9D illustrates a production cycle 908 of a fourth bioreactor in a bioreactor facility (e.g., bioreactor 808 illustrated and described with reference to FIG. 8A). Each of the production cycles 902, 904, 906, 908 may include a sterilization phase, a seeding phase, a growth phase (e.g., a cellular growth phase or a callus-growth phase), a trichome phase, and a harvest phase, for example. Further, as illustrated by the three dots in each production cycle 902, 904, 906, 908, each of the production cycles 902, 904, 906, 908 may be repeated upon completion of the harvest phase.

It is understood that the production cycles 902, 904, 906, 908 illustrated in FIGS. 9A-9D are provided solely as examples and that other production cycles are also possible and are contemplated herein. For example, production cycles could have different numbers of phases and/or different lengths of phases. In some embodiments, for instance, one or more of the production cycles 902, 904, 906, 908 may include an initialization phase. Such an initialization phase may include calibrating one or more sensors within the respective bioreactors, confirming that the one or more sensors and/or one or more other components within the bioreactors are fully operational (e.g., confirming that the illumination system of the bioreactor can provide illumination light, that the environmental control system of the bioreactor can modify temperature/humidity within the bioreactor, that the fluid management system of the bioreactor can provide adequate flow of fluids to the bioreactor tiles, etc.), and/or configuring communications between the respective bioreactor and a facility-management server. Further, in some embodiments, two production cycles executed by different bioreactors in the same bioreactor facility may be different from one another (e.g., have a different number of phases, different lengths of time for different phases, etc.).

Figure 9E:
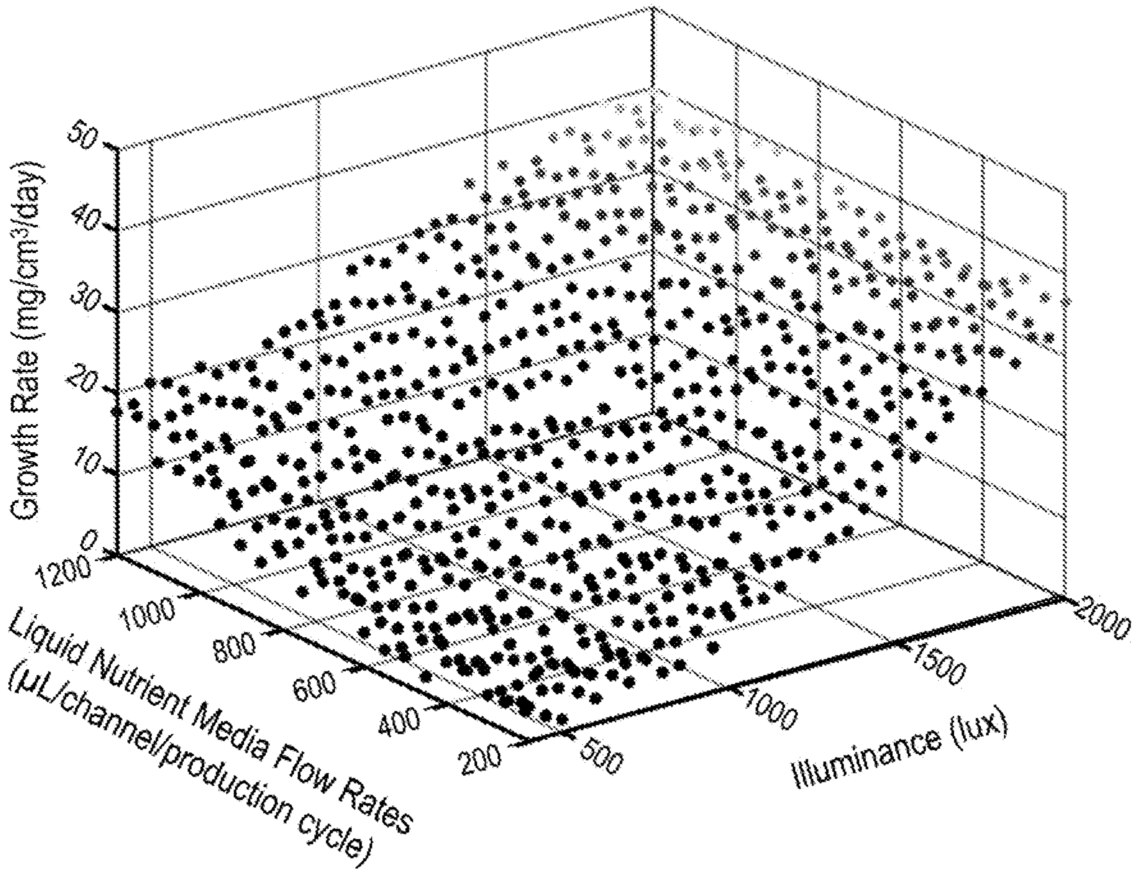
FIG. 9E is an illustration of a plot used for optimization, according to example embodiments.

As illustrated in FIGS. 9A-9D, the production cycles 902, 904, 906, 908 may be staggered in time such that the same phases in the various production cycles 902, 904, 906, 908 being at different points in time. Coordination of the staggering of production cycles may be performed by a facility-management server (e.g., the facility-management server 810 illustrated and described with reference to FIG. 8A). This may allow the facility-management server 810 to use the data from a given phase of one production cycle to optimize the related phase in another production cycle. For example, the facility-management server 810 may use data from the seeding phase of the first production cycle 902 (e.g., as measured by sensor(s) of the first bioreactor 802) to modify operating parameters of the fourth bioreactor 808 during the seeding phase of the fourth production cycle 908. As just one optimization example, the facility-management server 810 may survey liquid nutrient media flow rates (e.g., in μL per channel within the respective bioreactor tiles per production cycle) and illuminance values (e.g., in lux) used during the growth phases across various bioreactors within the bioreactor facility 800. Based on the corresponding growth rates of the plant cells (e.g., measured in $mg/cm^3$/day) within the bioreactors associated with the respective liquid nutrient media flow rates/illuminance values, the facility-management server 810 may generate a plot such as the plot illustrated in FIG. 9E. In some embodiments, the facility-management server 810 may interpolate between measured data points (e.g., by fitting a curve to the measured data) to generate a plot that includes a two-dimensional surface rather than discrete data points as illustrated in FIG. 9E. Based on the plot (e.g., based on the combination of media flow rate and illuminance value that provide the highest corresponding growth rate), the facility-management server 810 may modify the illuminance recipe used for future growth phases in bioreactors across the bioreactor facility 800. It is understood that similar optimizations could be performed by the facility-management server 810 for other variables, for other phases of the production cycle, and/or using different units of measure. Such alternative optimizations are also contemplated herein.

Each of the phases illustrated in FIGS. 9A-9D may include different recipes/configurations when it comes to illumination light (e.g., supplied by an illumination system of the respective bioreactors 802, 804, 806, 808), environmental conditions (e.g., supplied by an environmental control system of the respective bioreactors 802, 804, 806, 808), and/or fluid supply (e.g., supplied by the fluid management system of the respective bioreactors 802, 804, 806, 808). For example, as illustrated in the process 910 of FIG. 9F, a bioreactor 802, 804, 806, 808 may include one or more bioreactor tile configurations 912. For example, a bioreactor 802, 804, 806, 808 may include one bioreactor tile configuration 912 used for all bioreactor tiles within the respective bioreactor 802, 804, 806, 808. Alternatively, in some embodiments, a bioreactor 802, 804, 806, 808 may include a separate bioreactor tile configuration for each bioreactor tile within the bioreactor 802, 804, 806, 808 (e.g., based on which plant cells are growing within a given bioreactor tile and/or which products are being produced by that bioreactor tile). Such bioreactor tile configurations may be stored within a memory of the bioreactor (e.g., in a controller of the bioreactor). Further, the bioreactor tile configuration 912 may be provided to the bioreactor 802, 804, 806, 808 by the facility-management server 810, in some embodiments.

Figure 9F:
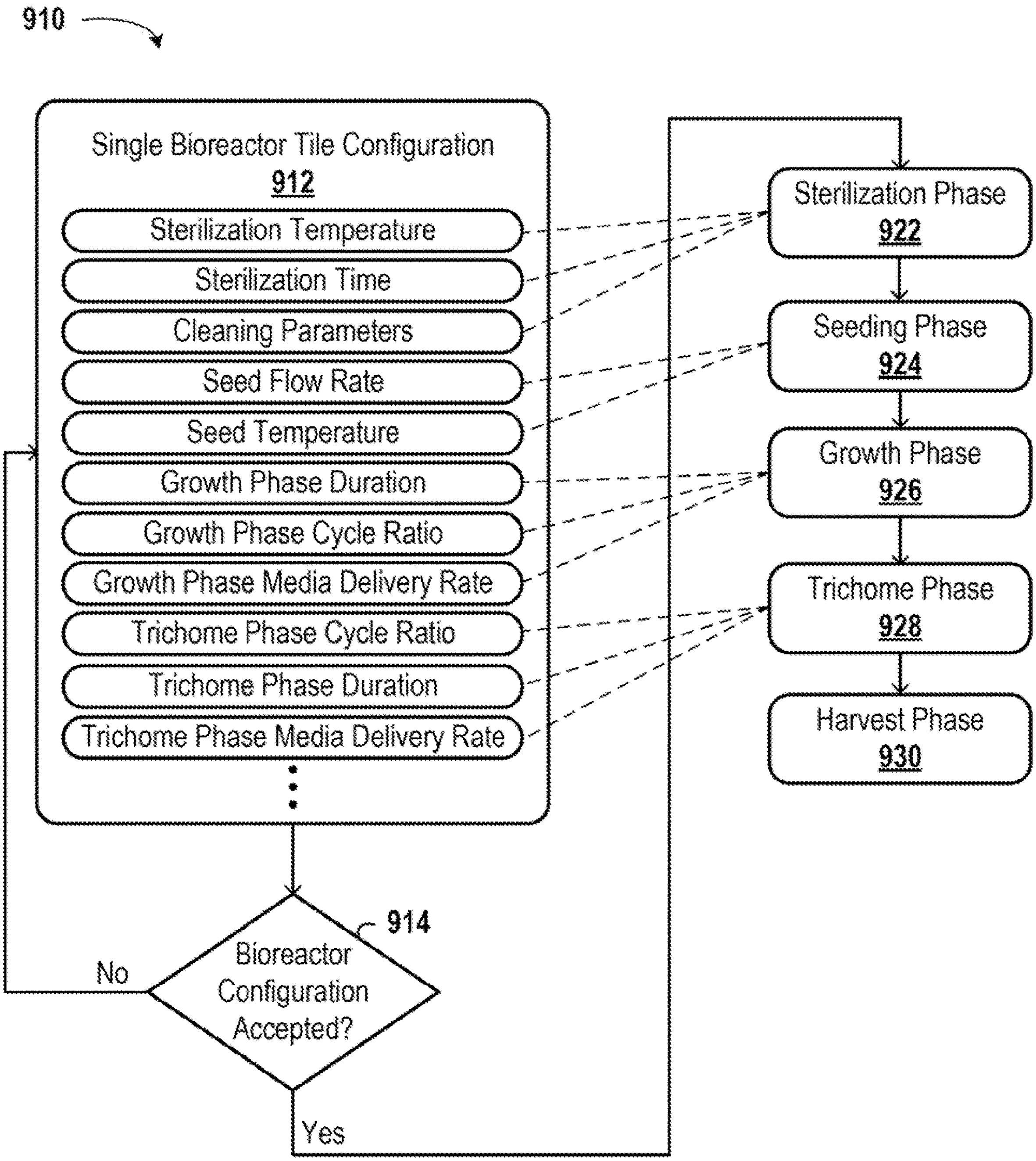
FIG. 9F is an illustration of a process of using a bioreactor tile configuration to perform a production cycle, according to example embodiments.

As illustrated in FIG. 9F, the bioreactor tile configuration 912 may include a number of operating parameters. For example, the bioreactor tile configuration 912 may include a sterilization temperature, a sterilization time, cleaning parameters, seed flow rate, seed temperature, growth phase duration, growth phase cycle ratio (e.g., the period/frequency of illumination light used during the growth phase), growth phase media delivery rate, trichome phase cycle ratio (e.g., the period/frequency of illumination light used during the trichome phase), trichome phase duration, and trichome phase media delivery rate. As illustrated by the three dots in FIG. 9F, it is understood that additional or alternative operating parameters are also possible and are contemplated herein. Once the single bioreactor tile configuration 912 is loaded by the bioreactor 802, 804, 806, 808 (e.g., by a controller of the bioreactor 802, 804, 806, 808), the process 910 may proceed to step 914. As illustrated in FIG. 9F, the operating parameters may influence various phases of a production cycle. For example, the sterilization temperature, the sterilization time, and the cleaning parameters may influence operation of the sterilization phase 922 of the production cycle. Further, the seed flow rate and the seed temperature may influence operation of the seeding phase 924 of the production cycle. Likewise, the growth phase duration, the growth phase cycle ratio, and the growth phase media delivery rate may influence operation of the growth phase 926 of the production cycle. Similarly, the trichome phase cycle ratio, the trichome phase duration, and the trichome phase media delivery rate may influence the trichome phase 928 of the production cycle.

At step 914, the process 910 may include determining whether a complete bioreactor configuration has been accepted. This determination may be made by the controller of the bioreactor 802, 804, 806, 808, for example. If the complete bioreactor configuration has been accepted, the process 910 may proceed to performing the production cycle using the bioreactor 802, 804, 806, 808. As illustrated, the production cycle may include the sterilization phase 922, the seeding phase 924, the growth phase 926, the trichome phase 928, and the harvest phase 930 (e.g., as shown and described with reference to FIGS. 9A-9D. If the complete bioreactor configuration has not been accepted (e.g., indicating that one or more tiles do not have an assigned bioreactor tile configuration yet), the process 910 may proceed loading in additional bioreactor tile configurations (e.g., like the bioreactor tile configuration 912 already loaded in for one or more bioreactor tiles).

One operating parameter that may be included in recipes/bioreactor tile configurations may be illumination settings for illumination light provided by an illumination system of the bioreactor 802, 804, 806, 808. For example, the seeding phase and/or the growth phase may include repeatedly providing 16 hours of illumination light followed by 8 hours of darkness, whereas the trichome phase may include repeatedly providing 12 hours of illumination light followed by 12 hours of darkness and/or the sterilization phase and harvest phase may include providing constant darkness. While lighting conditions may be presented throughout the disclosure as X hours of light followed by Y hours of darkness, it is understood that intermediate lighting conditions are also possible and are contemplated herein. For example, lighting conditions such as 8 hours of 0% intensity, followed by 8 hours of 50% intensity, followed by 8 hours of 100% intensity are also possible. Likewise, ramping up or down of intensity over time is also possible (e.g., a linear ramp up or ramp down of intensity, a quadratic ramp up or ramp down of intensity, an exponential ramp up or ramp down of intensity, etc.).

Figure 9G:
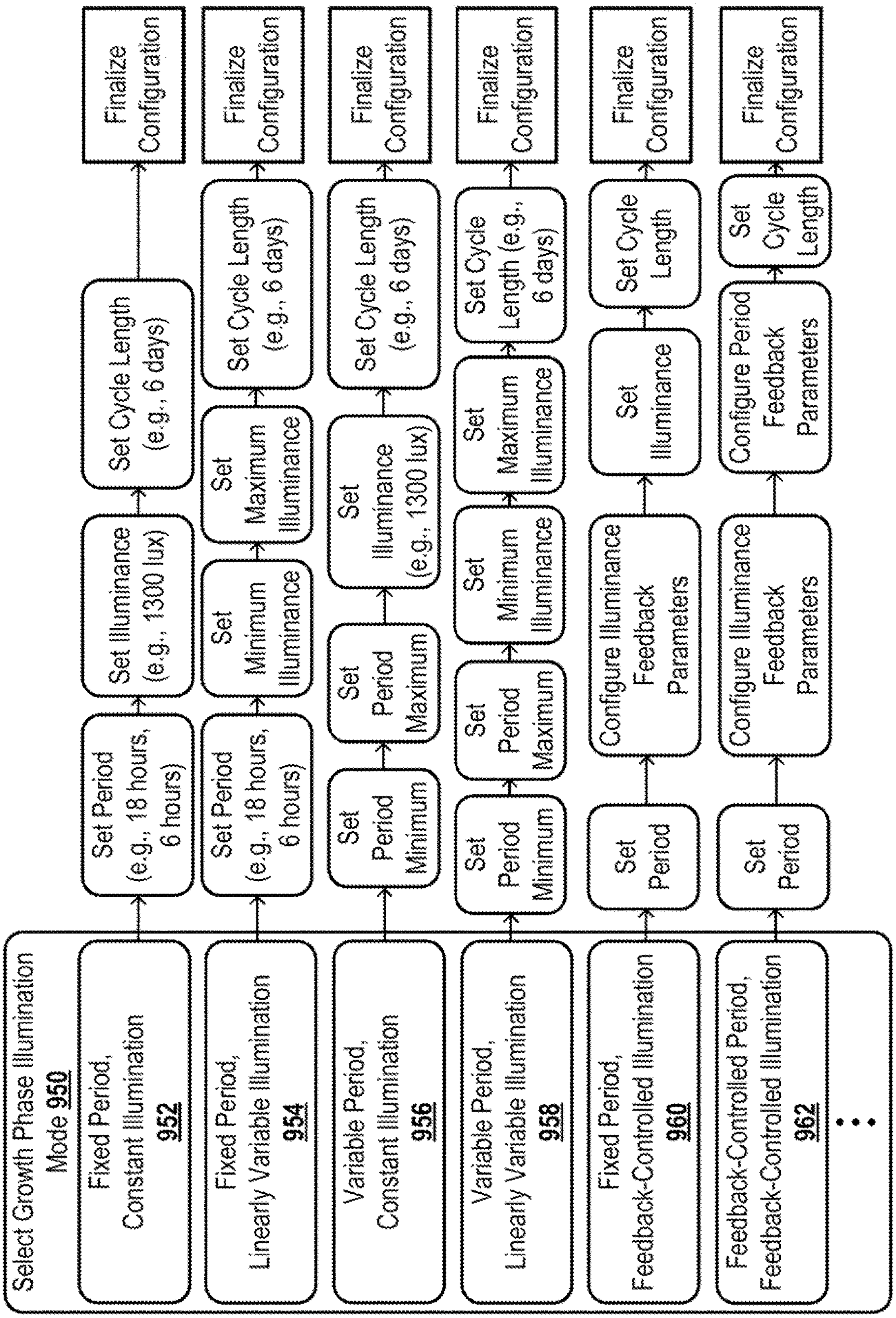
FIG. 9G is an illustration of illumination modes used by an illumination system in a bioreactor, according to example embodiments.

In some embodiments, the operating parameters related to illumination by the illumination system may be selected from a prescribed set of operating parameters. Then, the operating parameters that are selected from the prescribed set may be assigned values. For example, as illustrated in FIG. 9G, an illumination mode may be selected from a set of prescribed illumination modes. In the example of FIG. 9G, an illumination mode 950 is being selected for a growth phase. It is understood that this is provided solely as an example and that other phases within the production cycle may also have selectable illumination modes. As illustrated, the illumination mode 950 for the growth phase may be selected from: fixed period, constant illumination 952; fixed period, linearly variable illumination 954; variable period, constant illumination 956; variable period, linearly variable illumination 958; fixed period, feedback-controlled illumination 960; and feedback-controlled period, feedback-controlled illumination 962. As indicated by the three vertical dots in FIG. 9G, it is understood that additional or alternative illumination modes are also possible and are contemplated herein.

Figure 9H:
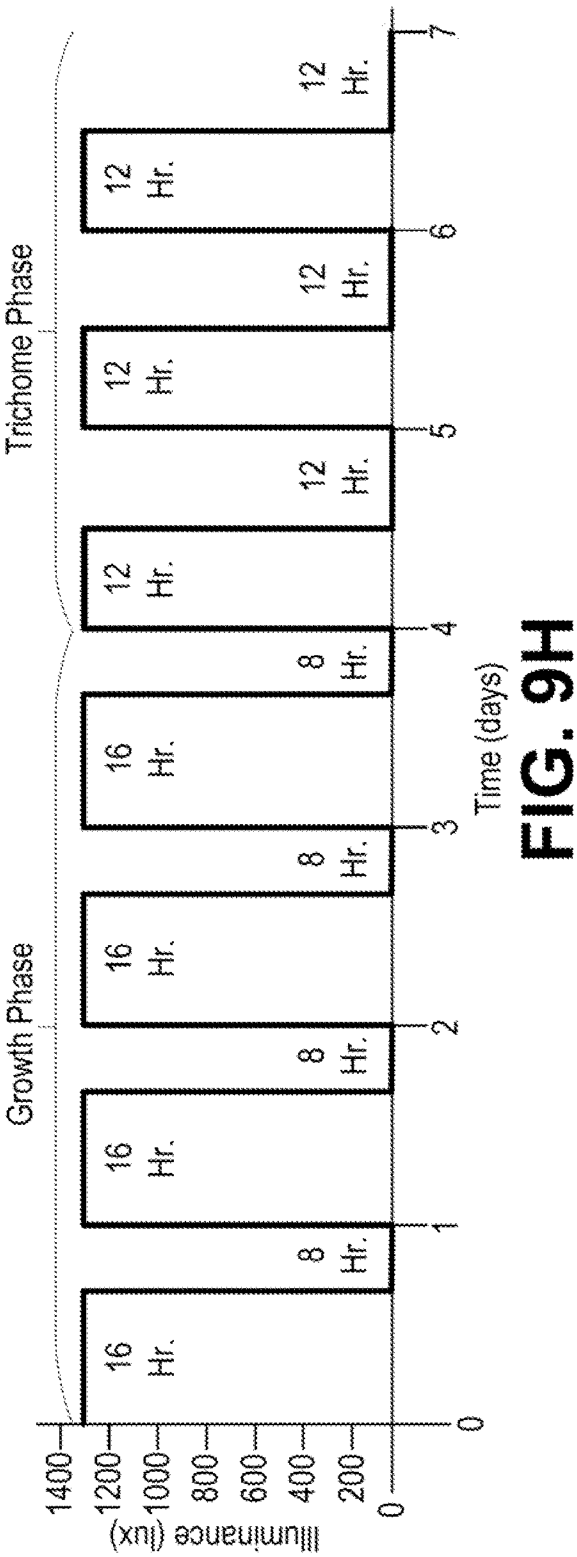
FIG. 9H is an illustration of an illuminance provided by an illumination system in a bioreactor during various phases of a production cycle, according to example embodiments.

The fixed period, constant illumination 952 mode may include providing illumination light (e.g., using the illumination system of the bioreactor 802, 804, 806, 808) at an assigned illuminance (e.g., measured in lux, such as 1300 lux) for an assigned duration (e.g., 16 hours) and then providing no illumination light for another assigned duration (e.g., 8 hours). These assigned durations may then be repeated according to a certain period (e.g., every 24 bouts). Further, such a cycle may last for an assigned number of cycles/cycle length (e.g., 6 days), at which point the growth phase may end and the production cycle may proceed to the next phase (e.g., a trichome phase that includes providing illumination light at an assigned illuminance for 12 hours and then providing no illumination light for 12 hours). An example plot of illumination versus time for such a growth phase followed by a trichome phase is illustrated in FIG. 9H.

Figure 9I:
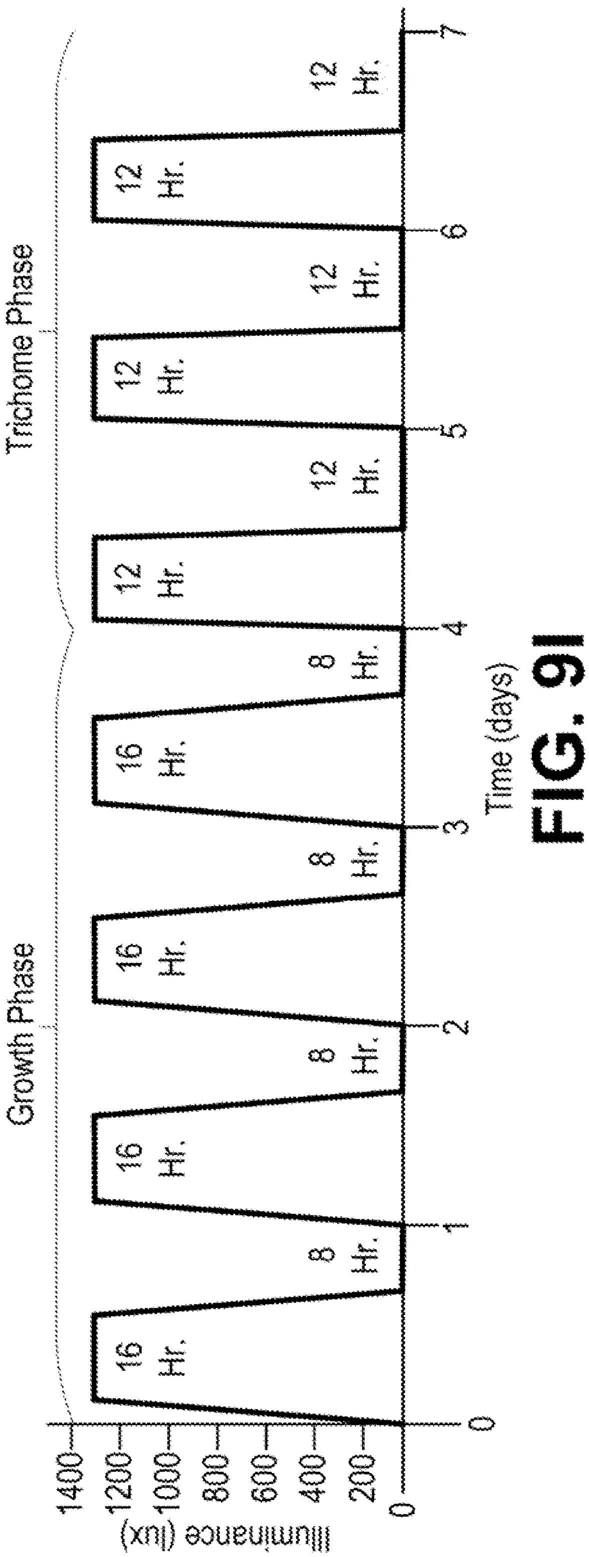
FIG. 9I is an illustration of an illuminance provided by an illumination system in a bioreactor during various phases of a production cycle, according to example embodiments.

The fixed period, linearly variable illumination 954 mode may include providing illumination light (e.g., using the illumination system of the bioreactor 802, 804, 806, 808) at an assigned minimum illuminance (e.g., measured in lux, such as 0 lux or 200 lux) for an assigned duration (e.g., 6 hours) and then providing illumination light at an assigned maximum illuminance (e.g., measured in lux, such as 1300 lux or 1500 lux) for another assigned duration (e.g., 14 hours). However, when transitioning between these two extremes, the illuminance of the illumination light may be ramped (e.g., linearly) up or down (e.g., over the course of two hours). These assigned durations may then be repeated according to a certain period (e.g., every 24 hours). Further, such a cycle may last for an assigned number of cycles/cycle length (e.g., 6 days), at which point the growth phase may end and the production cycle may proceed to the next phase (e.g., a trichome phase that includes providing illumination light at an assigned illuminance for 10 hours and then providing no illumination light for 10 hours, with a linear ramping up or down of illumination between the two). An example plot of illumination versus time for such a growth phase followed by a trichome phase is illustrated in FIG. 9I.

The variable period, constant illumination 956 mode may include providing illumination light (e.g., using the illumination system of the bioreactor 802, 804, 806, 808) at an assigned illuminance (e.g., measured in lux, such as 1300 lux) for an adjustable duration (e.g., between an assigned period minimum and an assigned period maximum) and then providing no illumination light for the remaining duration (e.g., 24 hours minus the duration for which the assigned illuminance was provided). These assigned durations may then be repeated according to a certain period (e.g., every 24 hours). Further, such a cycle may last for an assigned number of cycles/cycle length (e.g., 6 days), at which point the growth phase may end and the production cycle may proceed to the next phase (e.g., a trichrome phase that includes providing illumination light at an assigned illuminance for 12 hours and then providing no illumination light for 12 hours).

The variable period, linearly variable illumination 958 mode may include providing illumination light (e.g., using the illumination system of the bioreactor 802, 804, 806, 808) at an assigned maximum illuminance (e.g., measured in lux, such as 1300 lux or 1500 lux) for an adjustable duration (e.g., between an assigned period minimum and an assigned period maximum) and then providing illumination light at an assigned minimum illuminance (e.g., measured in lux, such as 0 lux or 200 lux) for the remaining duration (e.g., 24 hours minus the duration for which the assigned maximum illuminance was provided). However, when transitioning between these two extremes, the illuminance of the illumination light may be ramped (e.g., linearly) up or down (e.g., over the course of two hours). These assigned durations may then be repeated according to a certain period (e.g., every 24 hours). Further, such a cycle may last for an assigned number of cycles/cycle length (e.g., 6 days), at which point the growth phase may end and the production cycle may proceed to the next phase (e.g., a trichome phase that includes providing illumination light at an assigned illuminance for 12 hours and then providing no illumination light for 12 hours).

The fixed period, feedback-controlled illumination 960 mode may include providing illumination light (e.g., using the illumination system of the bioreactor 802, 804, 806, 808) at an assigned illuminance (e.g., 1300 lux) for an assigned duration (e.g., 16 hours) and then providing no illumination light for another assigned duration (e.g., 8 hours). The conditions of one or more bioreactor tiles (e.g., growth rate of cells within the bioreactor tiles) may be monitored by the controller of the respective bioreactor 802, 804, 806, 808 (e.g., based on data captured by one or more sensors of the respective bioreactor 802, 804, 806, 808). Then, based on the monitored conditions and the assigned duration, the controller of the respective bioreactor 802, 804, 806, 808 may adjust illuminance parameters (e.g., wavelength, illuminance, etc.) for future cycles. These assigned durations may then be repeated according to a certain period (e.g., every 24 hours). Further, such a cycle may last for an assigned number of cycles/cycle length (e.g., 6 days), at which point the growth phase may end and the production cycle may proceed to the next phase (e.g., a trichome phase that includes providing illumination light at an assigned illuminance for 12 hours and then providing no illumination light for 12 hours).

The feedback-controlled period, feedback-controlled illumination 962 mode may include providing illumination light (e.g., using the illumination system of the bioreactor 802, 804, 806, 808) at an assigned illuminance (e.g., 1300 lux) for an assigned duration (e.g., 16 hours) and then providing no illumination light for another assigned duration (e.g., 8 hours). The conditions of one or more bioreactor tiles (e.g., growth rate of cells within the bioreactor tiles) may be monitored by the controller of the respective bioreactor 802, 804, 806, 808 (e.g., based on data captured by one or more sensors of the respective bioreactor 802, 804, 806, 808). Then, based on the monitored conditions, the controller of the respective bioreactor 802, 804, 806, 808 may adjust illuminance parameters (e.g., wavelength(s), spectral profile, illuminance, etc.) and illuminance duration (e.g., hours at which the illuminance is at a maximum value) for future cycles. Then, using the adjusted illuminance parameters and illuminance durations, the cycle of providing illumination followed by no illumination light may be repeated. Further, such a cycle may last for an assigned number of cycles/cycle length (e.g., 6 days), at which point the growth phase may end and the production cycle may proceed to the next phase (e.g., a trichome phase that includes providing illumination light at an assigned illuminance for 12 hours and then providing no illumination light for 12 hours).

Figure 9J:
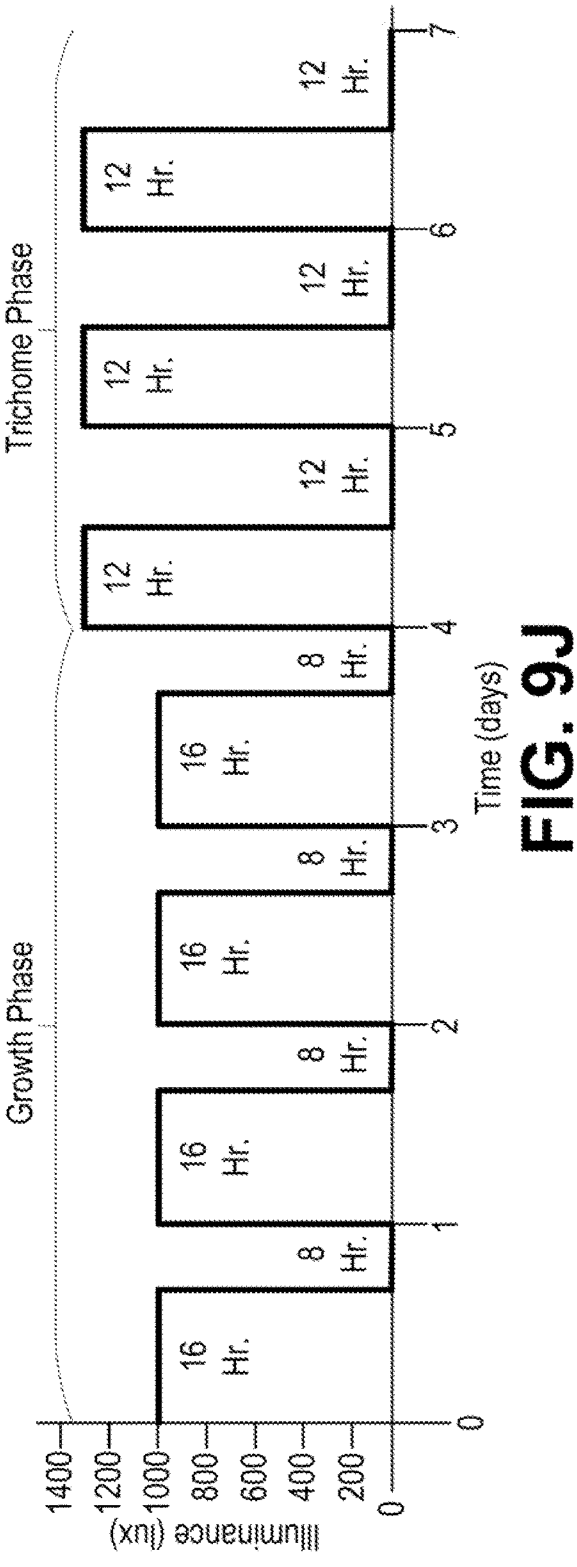
FIG. 9J is an illustration of an illuminance provided by an illumination system in a bioreactor during various phases of a production cycle, according to example embodiments.
Figure 9K:
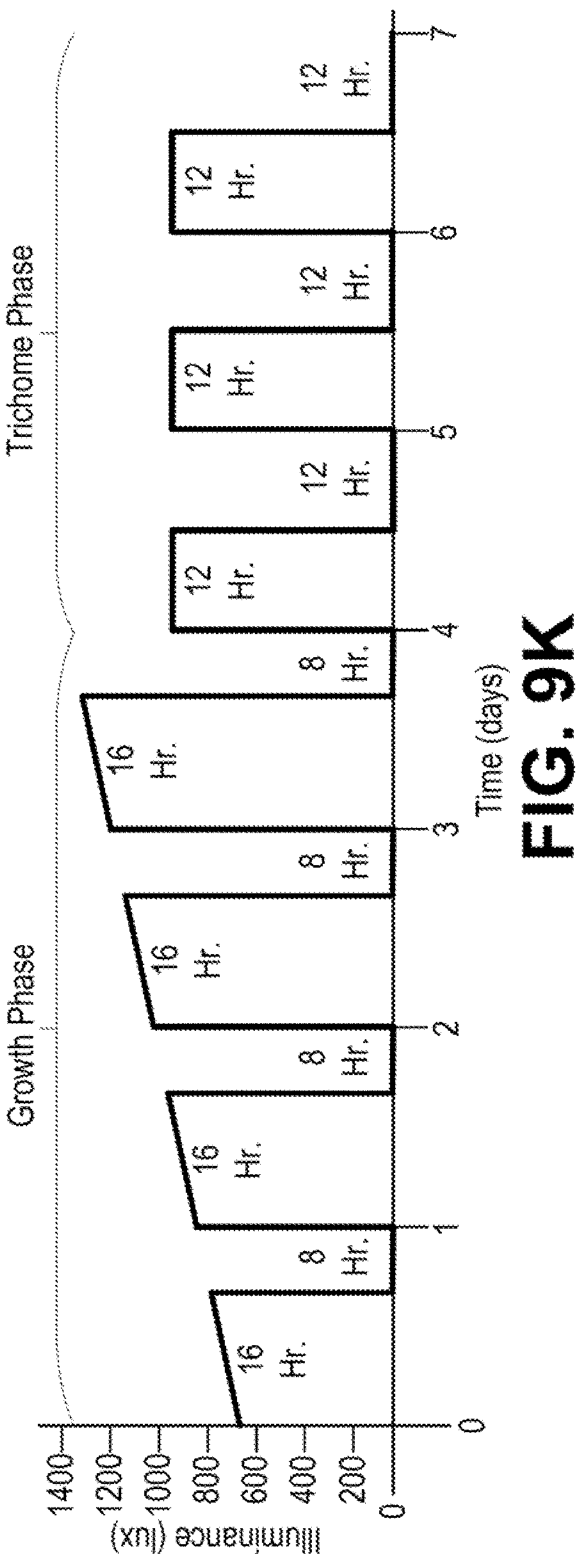
FIG. 9K is an illustration of an illuminance provided by an illumination system in a bioreactor during various phases of a production cycle, according to example embodiments.

FIGS. 9J and 9K illustrate alternative illumination schemes (e.g., according to one or more bioreactor tile configurations) for both growth phases and trichome phases of a production cycle. As illustrated in FIG. 9J, in some embodiments, the illuminance for the growth phase (e.g., about 1000 lux) may be less than the illuminance for the trichome phase (e.g., about 1300 lux). As illustrated in FIG. 9K, in some embodiments, the illuminance may be ramped up, cycle over cycle, during the growth phase. As such, the illuminance during the growth phase may be less than the illuminance of the trichome phase for portions (e.g., about 650 lux compared to about 950 lux) and more than the illuminance of the trichome phase for portions (e.g., about 1300 lux compared to about 950 lux). It is understood that additional or alternative illumination schemes (e.g., other than those presented in FIGS. 9G-9K) are also possible and are contemplated herein.

While FIGS. 9G-9K illustrate operating parameters related to the illumination system of a bioreactor, it is understood that other types of operating parameters for other components of the bioreactor may also be used in recipes/bioreactor tile configurations. For example, the harvest phase may include the fluid management system of the respective bioreactor infusing extractant (e.g., at a temperature of between −5° C. and 0° C.) into the bioreactor tiles and removing the infused extractant from the bioreactor tiles (e.g., along with the one or more chemical products resulting from shearing trichomes produced by parenchymal cells or puncturing trichomes produced by parenchymal cells), while the growth phase may include the fluid management system providing liquid nutrient media that induces callus growth and the trichome phase may include the fluid management system providing liquid nutrient media that induces trichome production. Still further, the sterilization phase may include the fluid management system flowing sterilization solution through one or more portions of the bioreactor tiles. Other illumination light conditions and/or fluid conditions are also possible and are contemplated herein. In addition, the different phases may include different environmental conditions (e.g., different temperatures, humidities, air pressures, etc.) from one another.

Further, a computing device of a respective bioreactor (e.g., the computing device 512 of the first bioreactor 802 for the first production cycle 902) may determine when to progress from one phase to another within a given production cycle. For example, the computing device 512 of the first bioreactor 802 may review data captured by one or more sensors of the first bioreactor 802 (e.g., data relating to conditions of the bioreactor and/or conditions of the cells within the bioreactor) and, based on the captured data, providing operating parameters to one or more components of the first bioreactor 802 (e.g., the fluid management system, the environmental control system, and/or the illumination system) that correspond to the next phase in the production cycle 902. For example, once the sensors of the first bioreactor 802 measure data that represents that the first bioreactor 802 is clean, the computing device 512 of the first bioreactor 802 may determine that it is time to progress to the seeding phase. This may involve providing instructions: to the fluid management system to being flowing a seed solution into one or more of the bioreactor tiles of the first bioreactor 802, to the environmental control system to adjust the heat and humidity that promote growth of the seeded cell stock, and to the illumination system to provide lighting conditions that promote growth of the seeded cell precursor.

Figure 10:
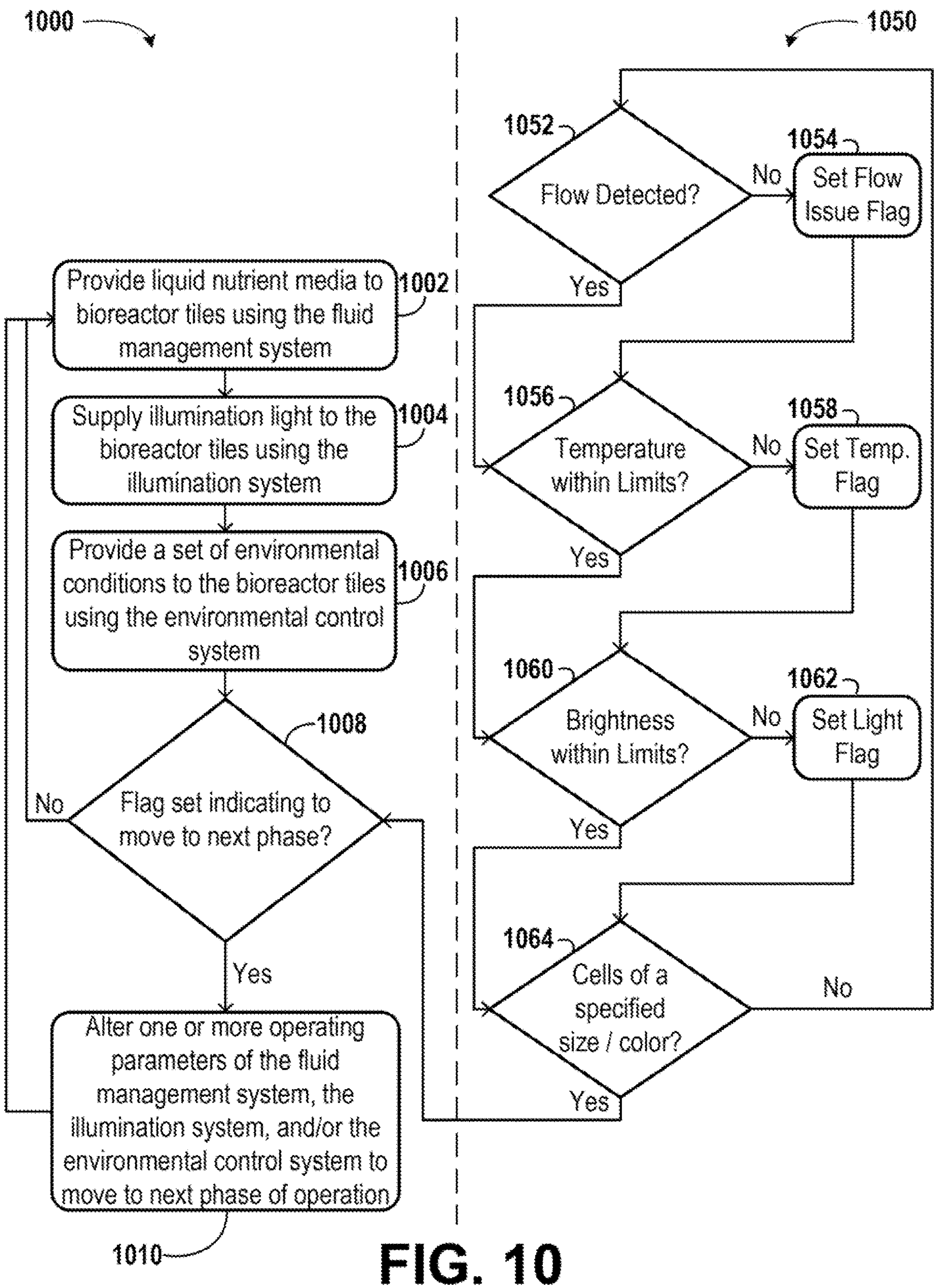
FIG. 10 is a flowchart illustrating parallel processes, according to example embodiments.

While monitoring the conditions of each phase of the respective production cycles 902, 904, 906, 908, the computing device of the respective bioreactor 802, 804, 806, 808 may also periodically communicate with a facility-management server (e.g., the facility-management server 810 shown and described with respect to FIG. 8A) of an associated bioreactor facility (e.g., the bioreactor facility 800 shown and described with respect to FIG. 8A). Such communication may be performed by the computing device of the respective bioreactor 802, 804, 806, 808 in order to assure that synchronization (e.g., as shown and described with reference to FIGS. 9A-9D) of related production cycles does not get out of step and/or to receive instructions from the facility-management server based on one or more flags raised in response to one or more trigger conditions being identified within the respective bioreactor 802, 804, 806, 808 (e.g., based on conditions sensed by one or more sensors within the respective bioreactor 802, 804, 806, 808). For example, FIG. 10 is a flowchart illustrated parallel processes that may be executed by a computing device of a bioreactor to monitor the progression of a given phase of a production cycle while simultaneously communicating with a facility-management server if one or more trigger conditions are met (e.g., threshold conditions stored within a memory of the computing device of the bioreactor). As such, FIG. 10 includes a phase monitoring process 1000 and a trigger condition monitoring process 1050. The phase of the production cycle illustrated in FIG. 10 may be a growth phase (e.g., the growth phase illustrated in FIGS. 9A-9D). However, it is understood that FIG. 10 is generally applicable to all phases of the production cycle and that similar parallel processes could be equally executed for other phases of the production cycle.

At step 1002, the phase monitoring process 1000 may include providing liquid nutrient media to the bioreactor tiles of the bioreactor using the fluid management system of the bioreactor. The liquid nutrient media may be provided to the bioreactor tiles according to one or more operating parameters of the fluid management system (e.g., flow rate, composition of fluid, etc.) set by the computing device of the bioreactor. After step 1002, the phase monitoring process 1000 may proceed to step 1004.

At step 1004, the phase monitoring process 1000 may include supplying illumination light to the bioreactor tiles of the bioreactor using the illumination system of the bioreactor. The illumination light may be supplied to the bioreactor tiles according to one or more operating parameters of the illumination system (e.g., illumination schedule, illumination wavelength(s), spectral profiles, illumination intensity, etc.) set by the computing device of the bioreactor. After step 1004, the phase monitoring process 1000 may proceed to step 1006.

At step 1006, the phase monitoring process 1000 may include providing a set of environmental conditions to the bioreactor tiles using the environmental control system. The environmental conditions may be provided to the bioreactor tiles according to one or more operating parameters of the environmental control system (e.g., temperature, humidity, air pressure, etc.) set by the computing device of the bioreactor. After step 1006, the phase monitoring process 1000 may proceed to step 1008.

At step 1008, the phase monitoring process 1000 may include the computing device of the bioreactor determining whether a flag has been set that indicates that the production cycle should proceed to a next phase of the production cycle or whether the current phase of the production cycle should continue (e.g., if the flag indicating to proceed to the need phase of the production cycle has not been set). Such a flag may be set according to step 1064 of the trigger condition monitoring process 1050, for example. If the computing device of the bioreactor determines that a flag has not been set that indicates to move to the next phase of the production cycle, the phase monitoring process 1000 may proceed to step 1002. If the computing device of the bioreactor determines that a flag has been set that indicates to move to the next phase of the production cycle, the phase monitoring process 1000 may proceed to step 1010.

At step 1010, the phase monitoring process 1000 may include the computing device providing instructions to the fluid management system, the illumination system, and/or the environmental control system of the bioreactor in order to alter one or more operating parameters of the fluid management system, the illumination system, and/or the environmental control system to move to the next phase of operation (e.g., next phase of the production cycle). For example, the operating temperature, operating humidity, illumination light intensity, illumination light wavelength, composition of the liquid nutrient media used, flow rate for air being provided to the bioreactor tiles, flow rate for liquid nutrient media being provided to the bioreactor tiles, and/or illumination schedule may be modified to move from one phase of the production cycle to the next. After step 1010, the phase monitoring process 1000 may proceed to step 1002 (e.g., to repeat the phase monitoring process 1000 with a new/revised set of operating parameters).

At step 1052, the trigger condition monitoring process 1050 may include determining whether a threshold flow is detected (e.g., by comparing data from a flow detector that is transmitted to the computing device and indicates flow rate to a threshold flow rate). If a threshold flow is not detected (e.g., indicating a clog in the bioreactor tile or in the tubing/pipes/flow lines of the bioreactor), the trigger condition monitoring process 1050 may proceed to step 1054. If a threshold flow is detected, the trigger condition monitoring process 1050 may proceed to step 1056. It is understood that other statuses related to the fluid management system could also be monitored for flags, as well (e.g., jammed valves, full tanks, empty tanks, contaminated fluid mixtures, etc.).

At step 1054, the trigger condition monitoring process 1050 may include setting a flow issue flag. The flow issue flag could indicate the exact issue (e.g., clog detected in a specific fluid line within the bioreactor), a general issue (e.g., clog detected somewhere within the bioreactor), or an unknown issue (e.g., flow rate below expected flow rate; source of decreased flow rate undetermined). The flow issue flag may be transmitted to the facility-management server, for example. Additionally or alternatively, the flow issue flag may be set in a memory (e.g., a volatile memory) of the computing device of the bioreactor, which may be readable by the facility-management server. In some embodiments, the facility-management server may provide additional instructions to the computing device of the bioreactor upon determining that the flow issue flag is set. Such additional instructions may include operating parameters to attempt to fix and/or mitigate the issue and/or instructions indicating to pause the production cycle until a technician can be dispatched to the bioreactor. After step 1054, the trigger condition monitoring process 1050 may proceed to step 1056.

At step 1056, the trigger condition monitoring process 1050 may include determining whether a threshold temperature is detected (e.g., by comparing data from a temperature sensor that is transmitted to the computing device and indicates temperature within the bioreactor to a temperature range). If the temperature is determined to not be within the limits of the temperature range (e.g., indicating an overheating or an overcooling of the bioreactor), the trigger condition monitoring process 1050 may proceed to step 1058. If the temperature is determined to be within the limits of the temperature range, the trigger condition monitoring process 1050 may proceed to step 1060. It is understood that other statuses related to the environmental control system could also be monitored for flags, as well (e.g., humidities, air pressures, threshold changes in temperature or humidity over a given time period, etc.).

At step 1058, the trigger condition monitoring process 1050 may include setting a temperature flag. The temperature flag could indicate the exact issue (e.g., temperature too high within the bioreactor), a general issue (e.g., temperature not within acceptable range in bioreactor), or an unknown issue (e.g., temperature putatively detected by temperature sensor is outside of an acceptable range). The temperature flag may be transmitted to the facility-management server, for example. Additionally or alternatively, the temperature flag may be set in a memory (e.g., a volatile memory) of the computing device of the bioreactor, which may be readable by the facility-management server. In some embodiments, the facility-management server may provide additional instructions to the computing device of the bioreactor upon determining that the temperature flag is set. Such additional instructions may include operating parameters to attempt to fix and/or mitigate the issue and/or instructions indicating to pause the production cycle until a technician can be dispatched to the bioreactor. After step 1058, the trigger condition monitoring process 1050 may proceed to step 1060.

At step 1060, the trigger condition monitoring process 1050 may include determining whether a threshold brightness is detected (e.g., by comparing data from an optical sensor that is transmitted to the computing device and indicates intensity of the illumination light within the bioreactor to an intensity range). If the intensity of the illumination light is determined to not be within the limits of the intensity range, the trigger condition monitoring process 1050 may proceed to step 1062. If the intensity of the illumination light is determined to be within the limits of the intensity range, the trigger condition monitoring process 1050 may proceed to step 1064. It is understood that other statuses related to the illumination system could also be monitored for flags, as well (e.g., wavelength of illumination light, period of time associated with light portions or dark portions of an illumination schedule, etc.).

At step 1062, the trigger condition monitoring process 1050 may include setting an illumination light flag. The illumination light flag could indicate the exact issue (e.g., illumination light is too bright within the bioreactor), a general issue (e.g., intensity of the illumination light is not within an acceptable range in bioreactor), or an unknown issue (e.g., intensity of illumination light putatively detected by optical sensor is outside of an acceptable range). The illumination light flag may be transmitted to the facility-management server, for example. Additionally or alternatively, the illumination light flag may be set in a memory (e.g., a volatile memory) of the computing device of the bioreactor, which may be readable by the facility-management server. In some embodiments, the facility-management server may provide additional instructions to the computing device of the bioreactor upon determining that the illumination light flag is set. Such additional instructions may include operating parameters to attempt to fix and/or mitigate the issue and/or instructions indicating to pause the production cycle until a technician can be dispatched to the bioreactor. After step 1062, the trigger condition monitoring process 1050 may proceed to step 1064.

At step 1064, the trigger condition monitoring process 1050 may include determining whether cells of a specified size and/or color are detected (e.g., by analyzing hyperspectral images captured by a hyperspectral imaging device of the bioreactor that is transmitted to the computing device). If cells of a specified color and/or size are present (e.g., indicating that the cells are ready to begin producing trichomes), the trigger condition monitoring process 1050 may set a flag indicating that the production cycle should move to a next phase (e.g., from the growth phase illustrated in FIGS. 9A-9D to the trichome phase illustrated in FIGS. 9A-9D). This flag may influence step 1008 of the phase monitoring process 1000, for example. If cells of a specified color and/or size are not present (e.g., indicating that the cells are not ready to begin producing trichomes), the trigger condition monitoring process 1050 may not set a flag indicating that the production cycle should move to a next phase and may instead proceed to step 1052 (to repeat the cycle of monitoring trigger conditions).

It is understood that while four trigger conditions are provided in FIG. 10, other numbers of trigger conditions could be monitored by the computing device. Additionally, numerous trigger conditions other than those listed in FIG. 10 (e.g., other than flow, temperature, brightness/intensity, and size/color of cells) are also possible and are contemplated herein. Further, in some embodiments, how many and which trigger conditions are being monitored by the computing device may depend on which phase of the production cycle the bioreactor/bioreactor tiles are currently in.

Figure 11:
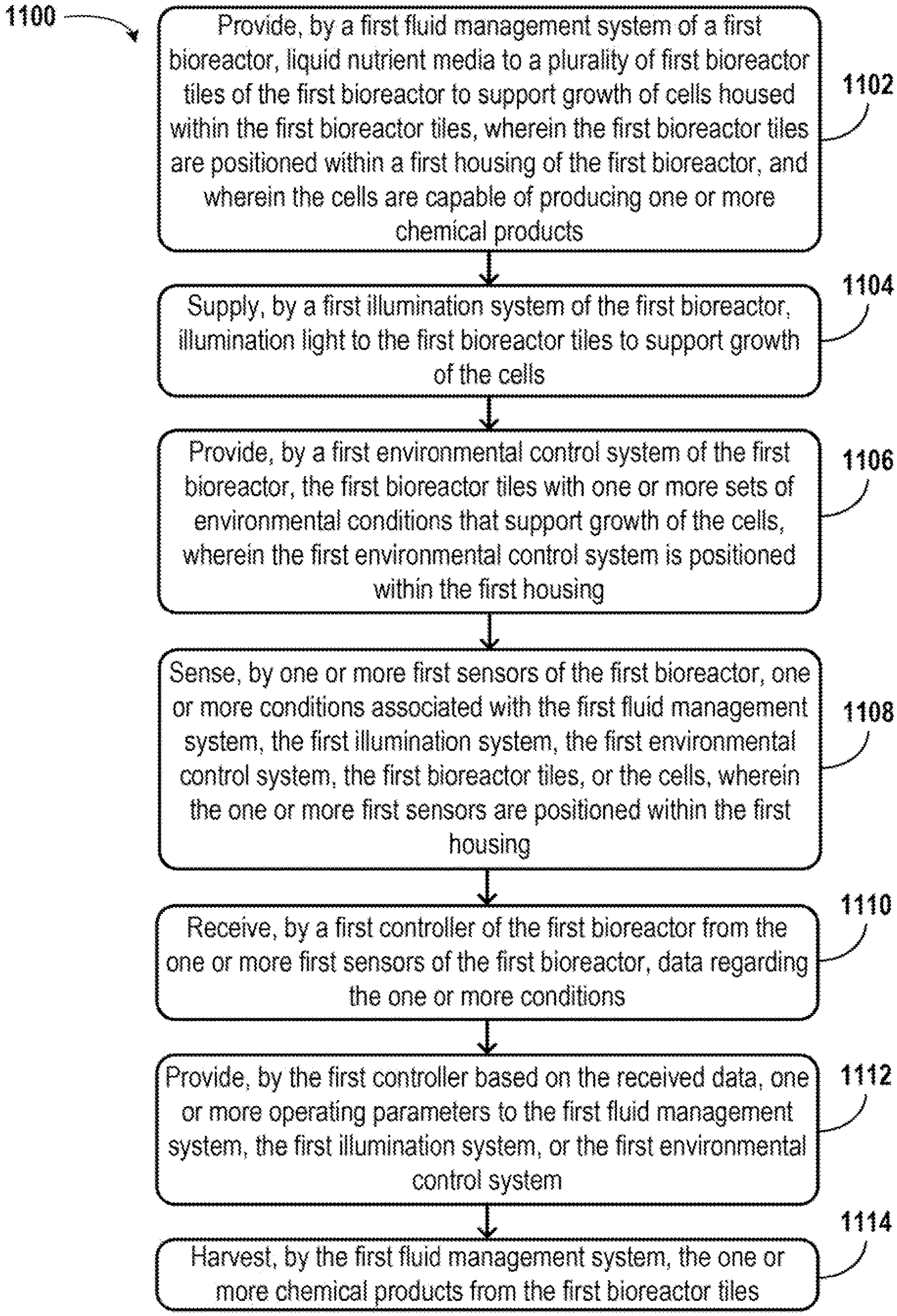
FIG. 11 is a flowchart illustrating a method, according to example embodiments.

FIG. 11 is a flowchart diagram of a method 1100, according to example embodiments. The method 1100 may be used to produce and harvest one or more chemical products (e.g., produced by one or more trichomes). The method 1100 may be performed by a system (e.g., the system illustrated in FIG. 8A). For example, a bioreactor of the bioreactor facility 800 may perform the method 1100.

At block 1102, the method 1100 may include providing, by a first fluid management system of a first bioreactor, liquid nutrient media to a plurality of first bioreactor tiles of the first bioreactor to support growth of cells housed within the first bioreactor tiles. The first bioreactor tiles may be positioned within a first housing of the first bioreactor. The cells may be capable of producing one or more chemical products.

At block 1104, the method 1100 may include supplying, by a first illumination system of the first bioreactor, illumination light to the first bioreactor tiles to support growth of the cells.

At block 1106, the method 1100 may include providing, by a first environmental control system of the first bioreactor, the first bioreactor tiles with one or more sets of environmental conditions that support growth of the cells. The first environmental control system may be positioned within the first housing.

At block 1108, the method 1100 may include sensing, by one or more first sensors of the first bioreactor, one or more conditions associated with the first fluid management system, the first illumination system, the first environmental control system, the first bioreactor tiles, or the cells. The one or more first sensors may be positioned within the first housing.

At block 1110, the method 1100 may include receiving, by a first controller of the first bioreactor from the one or more first sensors of the first bioreactor, data regarding the one or more conditions.

At block 1112, the method 1100 may include providing, by the first controller based on the received data, one or more operating parameters to the first fluid management system, the first illumination system, or the first environmental control system.

At block 1114, the method 1100 may include harvesting, by the first fluid management system, the one or more chemical products from the first bioreactor tiles.

In some embodiments of the method 1100, the cells may include parenchymal plant cells. Additionally, providing the liquid nutrient media to the plurality of first bioreactor tiles may include providing calli-induction media to the first bioreactor tiles. Further, supplying the illumination light to the first bioreactor tiles to support growth of the cells may include: supplying illumination light for about 16 hours and then supplying no illumination light for about 8 hours. In addition, providing the first bioreactor tiles with the one or more sets of environmental conditions that support growth of the cells may include providing a temperature of between 20° C. and 25° C.

In some embodiments, the method 1100 may also include determining, by the first controller based on the received data, that the cells are ready to begin production of trichomes. Providing the one or more operating parameters to the first fluid management system, the first illumination system, or the first environmental control system may include providing operating parameters to the first fluid management system, the first illumination system, and the first environmental control system that correspond to trichome production by the cells. Further, the method 1100 may include providing, by the first fluid management system, liquid nutrient media to the first bioreactor tiles to support trichome production according to the operating parameters provided by the first controller. In addition, the method 1100 may include providing, by the first illumination system, illumination light to the first bioreactor tiles to support trichome production according to the operating parameters provided by the first controller. Yet further, the method 1100 may include providing, by the first environmental control system, the first bioreactor tiles with one or more sets of environmental conditions that support trichome production according to the operating parameters provided by the first controller.

In some embodiments of the method 1100, providing by the first fluid management system, the liquid nutrient media to support trichome production may include providing trichome-induction media to the first bioreactor tiles. Further, providing, by the first illumination system, illumination light to support trichome production may include providing illumination light for about 12 hours and then supplying no illumination light for about 12 hours. Additionally, providing, by the first environmental control system, the first bioreactor tiles with the one or more sets of environmental conditions that support trichome production may include providing a temperature of between 20° C. and 25° C.

In some embodiments of the method 1100, the one or more first sensors may include one or more imaging sensors. Additionally, the received data may include an image or other representation captured by the one or more imaging sensors of the cells.

In some embodiments of the method 1100, the one or more imaging sensors may include a hyperspectral imaging sensor. Further, the image or other representation captured by the one or more imaging sensors of the cells may include a hyperspectral representation of a spectral signature of the cells. Additionally, determining, by the first controller based on the received data, that the cells are ready to begin production of trichomes may include determining, based on the spectral signature of the cells in the hyperspectral representation, that the cells are ready to progress from a callus-growth phase to a trichome-production phase.

In some embodiments, the method 1100 may also include determining, by the first controller based on the received data, that the one or more chemical products are ready to be harvested. Providing the one or more operating parameters to the first fluid management system, the first illumination system, or the first environmental control system may include providing operating parameters to the first fluid management system that correspond to harvesting the one or more chemical products from the first bioreactor tiles.

In some embodiments of the method 1100, harvesting, by the first fluid management system, the one or more chemical products from the first bioreactor tiles may include infusing extractant into the first bioreactor tile. Further, harvesting, by the first fluid management system, the one or more chemical products from the first bioreactor tiles may include removing the infused extractant along with the one or more chemical products from the first bioreactor tiles.

In some embodiments of the method 1100, infusing extractant into the first bioreactor tiles may include shearing trichomes produced by the cells. The trichomes may contain the one or more chemical products. Alternatively, infusing extractant into the first bioreactor tiles may include puncturing the trichomes produced by the cells in order to release the one or more chemical products.

In some embodiments of the method 1100, the one or more first sensors may include one or more imaging sensors. Additionally, the received data may include an image or other representation captured by the one or more imaging sensors of the trichomes.

In some embodiments of the method 1100, the one or more imaging sensors may include a hyperspectral imaging sensor. In addition, the image or other representation captured by the one or more imaging sensors of the trichomes may include a hyperspectral representation of a spectral signature of the trichomes. Further, determining, by the first controller based on the received data, that the one or more chemical products are ready to be harvested may include determining, based on the spectral signature of the trichomes in the hyperspectral representation, that the trichomes have matured to a state such that they contain a sufficient amount of the one or more chemical products.

In some embodiments, the method 1100 may also include performing a sterilization procedure. The sterilization procedure may include providing, by the first fluid management system, one or more cleaning solutions or gases to the first bioreactor tiles. Alternatively, the sterilization procedure may include supplying, by the first illumination system, the first bioreactor tiles with illumination light within a range of ultraviolet wavelengths in order sterilize the first bioreactor tiles. In still other embodiments, the sterilization procedure may include heating, by the first environmental control system, the first bioreactor tiles to a first temperature and subsequently cooling the first bioreactor tiles to a second temperature.

In some embodiments of the method 1100, performing the sterilization procedure may include heating, by the first environmental control system, the first bioreactor tiles to the first temperature and subsequently cooling the first bioreactor tiles to the second temperature. The first temperature may be between 175° C. and 185° C. The second temperature may be between 20° C. and 25° C.

In some embodiments, the method 1100 may also include supplying, by the first fluid management system of the first bioreactor, an air mixture to the first bioreactor tiles to support growth of the cells.

Figure 12:
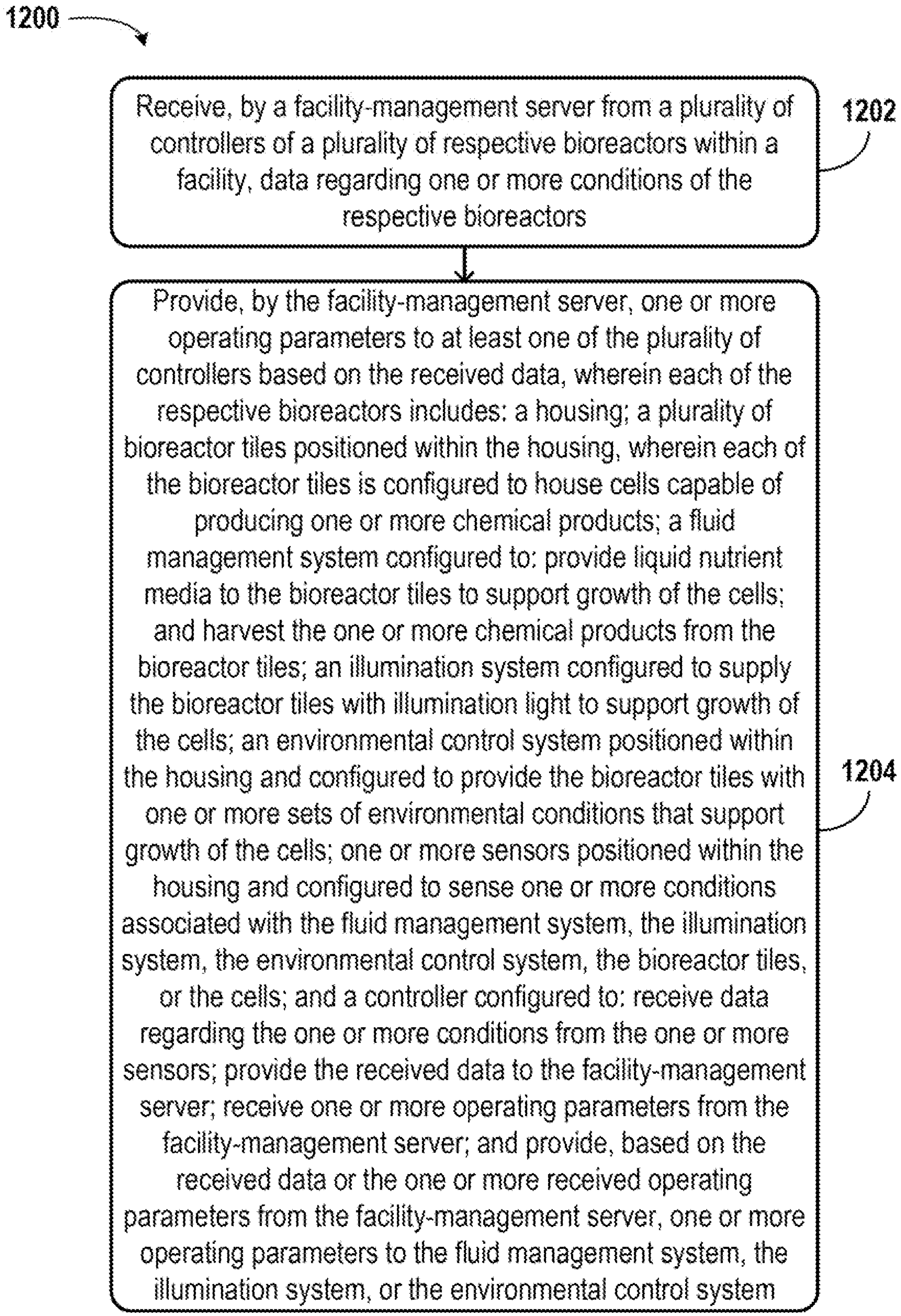
FIG. 12 is a flowchart illustrating a method, according to example embodiments.

FIG. 12 is a flowchart diagram of a method 1200, according to example embodiments. The method 1200 may be used to produce and harvest one or more chemical products (e.g., produced by one or more trichomes). The method 1200 may be performed by a system (e.g., the system illustrated in FIG. 8A). For example, the bioreactor facility 800 may perform the method 1200.

At block 1202, the method 1200 may include receiving, by a facility-management server from a plurality of controllers of a plurality of respective bioreactors within a facility, data regarding one or more conditions of the respective bioreactors.

At block 1204, the method 1200 may include providing, by the facility-management server, one or more operating parameters to at least one of the plurality of controllers based on the received data. Each of the respective bioreactors may include a housing. Each of the respective bioreactors may also include a plurality of bioreactor tiles positioned within the housing. Each of the bioreactors tiles may be configured to house cells capable of producing one or more chemical products. Additionally, each of the respective bioreactors may include a fluid management system. The fluid management system may be configured to provide liquid nutrient media to the bioreactor tiles to support growth of the cells. The fluid management system may also be configured to harvest the one or more chemical products from the bioreactor tiles. Further, each of the respective bioreactors may include an illumination system configured to supply the bioreactor tiles with illumination light used to support growth of the cells. In addition, each of the respective bioreactors may include an environmental control system positioned within the housing and configured to provide the bioreactor tiles with one or more sets of environmental conditions that support growth of the cells. Yet further, each of the respective bioreactors may include one or more sensors positioned within the housing and configured to sense one or more conditions associated with the fluid management system, the illumination system, the environmental control system, the bioreactor tiles, or the cells. Still further, each of the respective bioreactors may include a controller. The controller may be configured to receive data regarding the one or more conditions from the one or more sensors. The controller may also be configured to provide the received data to the facility-management server. Additionally, the controller may be configured to receive one or more operating parameters from the facility-management server. Further, the controller may be configured to provide, based on the received data or the one or more received operating parameters from the facility-management server, one or more operating parameters to the fluid management system, the illumination system, or the environmental control system.

In some embodiments of the method 1200, providing, by the facility-management server, the one or more operating parameters to at least one of the plurality of controllers based on the received data may include providing a first set of operating parameters to a first controller of a first bioreactor. Additionally, providing, by the facility-management server, the one or more operating parameters to at least one of the plurality of controllers based on the received data may include providing a second set of operating parameters to a second controller of a second bioreactor. The first set of operating parameters may cause one or more of the bioreactor tiles in the first bioreactor to begin a predetermined production phase at a first time. The second set of operating parameters may cause one or more of the bioreactor tiles in the second bioreactor to begin the same predetermined production phase at a second time. The second time may be after the first time.

In some embodiments of the method 1200, the predetermined production phase may be a sterilization phase, a seeding phase, a cellular growth phase, a callus-growth phase, a trichome-production phase, or a harvesting phase.

In some embodiments, the method 1200 may also include providing, by the facility-management server, a first set of operating parameters to a first controller of a first bioreactor within the facility. Further, the method 1200 may include providing, by the facility-management server, a second set of operating parameters to a second controller of a second bioreactor within the facility. Receiving, by the facility-management server, data regarding the one or more conditions of the respective bioreactors may include receiving, from the first controller, one or more conditions of the first bioreactor. Receiving, by the facility-management server, data regarding the one or more conditions of the respective bioreactors may also include receiving from the second controller, one or more conditions of the second bioreactor. Additionally, the method 1200 may include determining, by the facility-management server, one or more optimized operating parameters for the second bioreactor based on: the first set of operating parameters, the second set of operating parameters, the one or more conditions of the first bioreactor, and the one or more conditions of the second bioreactor. Providing, by the facility-management server, the one or more operating parameters to at least one of the plurality of controllers based on the received data may include providing the one or more optimized operating parameters to the first controller of the first bioreactor, the second controller of the second bioreactor, or a third controller of a third bioreactor.

In some embodiments of the method 1200, the facility-management server may be a server device that is located remotely from the facility.

In some embodiments of the method 1200, the facility-management server may be a server device located within the facility.

In some embodiments of the method 1200, receiving data regarding one or more conditions of the respective bioreactors may include receiving an indication that a first flag has been raised by a first controller of a first bioreactor within the facility. The first controller of the first bioreactor may be configured to raise the first flag when the data regarding the one or more conditions from the one or more sensors of the first bioreactor corresponds to a first trigger condition. Further, the method 1200 may include determining, by the facility-management server based on received indication that the first flag has been raised, the one or more operating parameters. Additionally, providing the one or more operating parameters to at least one of the plurality of controllers may include providing the one or more operating parameters to the first controller of the first bioreactor.

In some embodiments of the method 1200, the first trigger condition may represent a clog, a threshold change in temperature over a predetermined period of time, a threshold change in humidity over a predetermined period of time, a threshold change in pressure over a predetermined period of time, a threshold change in pH within a solution over a predetermined period of time, a threshold change in illumination intensity over a predetermined period of time, a threshold change in illumination wavelength over a predetermined period of time, a growth milestone relating to the cells in the first bioreactor, or a chemical production milestone.

III. CONCLUSION

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those described herein, will be apparent to those skilled in the art from the foregoing descriptions. Such modifications and variations are intended to fall within the scope of the appended claims.

The above detailed description describes various features and operations of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations.

With respect to any or all of the message flow diagrams, scenarios, and flow charts in the figures and as discussed herein, each step, block, operation, and/or communication can represent a processing of information and/or a transmission of information in accordance with example embodiments. Alternative embodiments are included within the scope of these example embodiments. In these alternative embodiments, for example, operations described as steps, blocks, transmissions, communications, requests, responses, and/or messages can be executed out of order from that shown or discussed, including substantially concurrently or in reverse order, depending on the functionality involved. Further, more or fewer blocks and/or operations can be used with any of the message flow diagrams, scenarios, and flow charts discussed herein, and these message flow diagrams, scenarios, and flow charts can be combined with one another, in part or in whole.

A step, block, or operation that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical operations or actions in the method or technique. The program code and/or related data can be stored on any type of computer-readable medium such as a storage device including RAM, a disk drive, a solid state drive, or another storage medium.

The computer-readable medium can also include non-transitory computer-readable media such as computer-readable media that store data for short periods of time like register memory and processor cache. The computer-readable media can further include non-transitory computer-readable media that store program code and/or data for longer periods of time. Thus, the computer-readable media may include secondary or persistent long term storage, like ROM, optical or magnetic disks, solid state drives, compact-disc read-only memory (CD-ROM), for example. The computer-readable media can also be any other volatile or non-volatile storage systems. A computer-readable medium can be considered a computer-readable storage medium, for example, or a tangible storage device.

Moreover, a step, block, or operation that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

Embodiments of the present disclosure may thus relate to one of the enumerated example embodiments (EEEs) listed below.

EEE 1 is a system comprising a first bioreactor, wherein the first bioreactor comprises:
- a first housing;
- a plurality of first bioreactor tiles positioned within the first housing, wherein each of the first bioreactor tiles is configured to house cells capable of producing one or more chemical products;
- a first fluid management system configured to:
  - provide liquid nutrient media to the first bioreactor tiles to support growth of the cells; and
  - harvest the one or more chemical products from the first bioreactor tiles;
- a first illumination system configured to supply the first bioreactor tiles with illumination light used to support growth of the cells;
- a first environmental control system positioned within the first housing and configured to provide the first bioreactor tiles with one or more sets of environmental conditions that support growth of the cells;
- one or more first sensors positioned within the first housing and configured to sense one or more conditions associated with the first fluid management system, the first illumination system, the first environmental control system, the first bioreactor tiles, or the cells; and
- a first controller configured to:
  - receive data regarding the one or more conditions from the one or more first sensors; and
  - provide, based on the received data, one or more operating parameters to the first fluid management system, the first illumination system, or the first environmental control system.

EEE 2 is the system of EEE 1, wherein each of the first bioreactor tiles comprises:
- a substrate having a first channel, a second channel, and a third channel defined therein, wherein the first channel is separated from the second channel by a first partial wall structure, wherein the second channel is separated from the third channel by a second partial wall structure, wherein the first channel is configured to receive the liquid nutrient media from the first fluid management system, wherein the second channel is configured to house the cells capable of producing the one or more chemical products, and wherein the third channel is configured to house the one or more chemical products produced by the cells; and
- an optical waveguide configured to:
  - receive the illumination light from the first illumination system at a first end of the optical waveguide;
  - propagate the illumination light toward a second end of the optical waveguide;
  - allow at least a portion of the illumination light to escape the optical waveguide from a first surface of the optical waveguide as the illumination light propagates toward the second end of the optical waveguide; and
  - provide the portion of the illumination light that escapes the optical waveguide from the first surface to the second channel or the third channel to support growth of the cells or production, by the cells, of the one or more chemical products.

EEE 3 is the system of EEE 2, wherein the third channel is further configured to house an air mixture, and wherein the air mixture is configured to enable gas exchange for the cells.

EEE 4 is the system of any of EEEs 1-3, wherein the plurality of first bioreactor tiles of the first bioreactor are arranged horizontally adjacent to one another within the first housing or are vertically stacked with respect to one another within the first housing.

EEE 5 is the system of any of EEEs 1-4, further comprising a second bioreactor, wherein the second bioreactor comprises:
- a second housing;
- a plurality of second bioreactor tiles positioned within the second housing, wherein each of the second bioreactor tiles is configured to house cells capable of producing one or more chemical products;
- a second fluid management system configured to:
  - provide liquid nutrient media to the second bioreactor tiles to support growth of the cells in the second bioreactor; and
  - harvest the one or more chemical products from the second bioreactor tiles;
- a second illumination system configured to supply the second bioreactor tiles with illumination light used to support growth of the cells in the second bioreactor,
- a second environmental control system positioned within the second housing and configured to provide the second bioreactor tiles with one or more sets of environmental conditions that support growth of the cells in the second bioreactor;
- one or more second sensors positioned within the second housing and configured to sense one or more conditions associated with the second fluid management system, the second illumination system, the second environmental control system, the second bioreactor tiles, or the cells in the second bioreactor, and
- a second controller configured to:
  - receive data regarding the one or more conditions from the one or more second sensors; and
  - provide, based on the received data, one or more operating parameters to the second fluid management system, the second illumination system, or the second environmental control system.

EEE 6 is the system of EEE 5, further comprising a bioreactor facility, wherein the first bioreactor and the second bioreactor are located within the bioreactor facility.

EEE 7 is the system of EEE 6, further comprising a facility-management server, wherein the facility-management server is configured to:

communicate with the first controller to:
receive data regarding the one or more conditions from the one or more first sensors; and
receive the one or more operating parameters provided to the first fluid management system, the first illumination system, or the first environmental control system;
communicate with the second controller to:
receive data regarding the one or more conditions from the one or more second sensors; and
receive the one or more operating parameters provided to the second fluid management system, the second illumination system, or the second environmental control system;
determine, based on: (i) the one or more conditions from the one or more first sensors; (ii) the one or more operating parameters provided to the second fluid management system, the second illumination system, or the second environmental control system; or (iii) the one or more conditions from the one or more second sensors, one or more revised operating parameters for the first fluid management system, the first illumination system, or the first environmental control system;
determine, based on: (i) the one or more conditions from the one or more second sensors; (ii) or the one or more operating parameters provided to the first fluid management system, the first illumination system, or the first environmental control system; or (iii) the one or more conditions from the one or more first sensors, one or more revised operating parameters for the second fluid management system, the second illumination system, or the second environmental control system;
provide, to the first controller, the one or more revised operating parameters for the first fluid management system, the first illumination system, or the first environmental control system; and
provide, to the second controller, the one or more revised operating parameters for the second fluid management system, the second illumination system, or the second environmental control system.

EEE 8 is the system of EEE 7,
wherein the first controller is configured to raise a first flag when the data regarding the one or more conditions from the one or more first sensors corresponds to a first trigger condition,
wherein the second controller is configured to raise a second flag when the data regarding the one or more conditions from the one or more second sensors corresponds to a second trigger condition,
wherein:
receiving the data regarding the one or more conditions from the one or more first sensors comprises identifying that the first flag is raised; or
receiving the data regarding the one or more conditions from the one or more second sensors comprises identifying that the second flag is raised.

EEE 9 is the system of EEE 8, wherein the first trigger condition or the second trigger condition represents: a clog, a threshold change in temperature over a predetermined period of time, a threshold change in humidity over a predetermined period of time, a threshold change in pressure over a predetermined period of time, a threshold change in pH within a solution over a predetermined period of time, a threshold change in illumination intensity over a predetermined period of time, a threshold change in illumination wavelength over a predetermined period of time, a growth milestone relating to the cells in the first bioreactor, a growth milestone relating to the cells in the second bioreactor, or a chemical production milestone.

EEE 10 is the system of any of EEEs 7-9, further comprising a facility-wide environmental control system positioned within the facility and configured to provide the first bioreactor and the second bioreactor with one or more sets of external environmental conditions, wherein the facility-management server is configured to provide one or more operating parameters to the facility-wide environmental control system, wherein the first environmental control system is configured to augment the one or more sets of external environmental conditions to provide the first bioreactor tiles with the one or more sets of environmental conditions that support growth of the cells, and wherein the second environmental control system is configured to augment the one or more sets of external environmental conditions to provide the second bioreactor tiles with the one or more sets of environmental conditions that support growth of the cells.

EEE 11 is the system of any of EEEs 7-10, further comprising a facility-wide fluid management system positioned within the facility and configured to provide the first bioreactor and the second bioreactor with one or more fluids used for operation or retrieve the one or more chemical products from the products from the first bioreactor and the second bioreactor.

EEE 12 is the system of EEE 11, wherein the facility comprises a floor surface and a subfloor surface, and wherein the facility-wide fluid management system comprises pipes, pumps, chambers, reservoirs, tanks, or valves located between the floor surface and the subfloor surface.

EEE 13 is the system of any of EEEs 5-12, wherein a species of the cells grown in at least one of the first bioreactor tiles is different from a species of the cells grown in at least one of the second bioreactor tiles.

EEE 14 is the system of any of EEEs 1-13, wherein a species of the cells grown in at least one of the first bioreactor tiles is different from a species of the cells grown in another of the first bioreactor tiles.

EEE 15 is the system of any of EEEs 1-14, wherein the one or more first sensors comprise a temperature sensor, a humidity sensor, a flow sensor, a camera, an optical microscope, a device configured to perform Raman spectroscopy, a device configured to perform hyperspectral imaging, or a device configured to perform fluorescence spectroscopy.

EEE 16 is the system of any of EEEs 1-15, wherein the one or more first sensors are movable within the housing or are removable from the housing.

EEE 17 is the system of any of EEEs 1-16, wherein the first fluid management system comprises a pump, a valve, a tube, a pipe a chamber, a reservoir, or a tank.

EEE 18 is the system of any of EEEs 1-17, wherein each of the first bioreactor tiles include an identical layout, and wherein the identical layout comprises:
one or more inlets configured to receive one or more fluids from the first fluid management system, wherein the one or more inlets are located at one or more first positions in the first bioreactor tiles;
one or more outlets configured to provide the one or more chemical products to the first fluid management system, wherein the one or more outlets are located at one or more second positions in the first bioreactor tiles; and
one or more optics configured to receive the illumination light from the first illumination system, wherein the one or more optics are located at one or more third positions in the first bioreactor tiles.

EEE 19 is the system of any of EEEs 1-18, wherein the first bioreactor further comprises one or more monitoring tiles configured to provide the first controller with data relating to an operation of the first fluid management system, the first illumination system, and the first environmental control system without cells present in the monitoring tiles, wherein the first fluid management system is further configured to provide fluids to the one or more monitoring tiles, wherein the first illumination system is configured to supply the one or more monitoring tiles with illumination light, and wherein the first environmental control system is configured to provide the one or more sets of environmental conditions to the one or more monitoring tiles.

EEE 20 is the system of any of EEEs 1-19, wherein the cells comprise parenchymal plant cells that produce trichomes, and wherein the parenchymal plant cells comprise *Cannabis sativa* cells, *Artemisia annua* cells, *Chrysanthemum cinerariifolium* cells, *Chrysanthemum coccineum* cells, *Gossypium hirsutum* cells, *Gossypium barbadense* cells, *Gossypium arboreum* cells, *Gossypium herbaceum* cells, *Lavandula angustifolia* cells, *Arabidopsis thaliana* cells, *Mentha* x *piperita* cells, or *Mentha haplocalyx* cells.

EEE 21 is the system of any of EEEs 1-20, wherein the one or more chemical products comprise cannabidiol, tetrahydrocannabinol, artemisinin, pyrethrum, camphor, glucosinolate, linalool, linalyl acetate, menthol, or peppermint camphor.

EEE 22 is the system of any of EEEs 1-21, wherein the liquid nutrient media comprise an inorganic salt, a carbon source, myoinositol, glycine, a vitamin, a growth regulator, a nitrogen compound, an organic acid, or a plant extract.

EEE 23 is the system of any of EEEs 1-22, wherein harvesting the one or more chemical products from the first bioreactor tiles comprises:

infusing extractant into the first bioreactor tiles; and removing the infused extractant along with the one or more chemical products from the first bioreactor tiles.

EEE 24 is the system of EEE 23, wherein the extractant comprises ethanol at a temperature of between −5° C. and 0° C.

EEE 25 is the system of any of EEEs 1-24, wherein the first fluid management system is further configured to provide liquid nutrient media to the first bioreactor tiles to support production of trichomes by the cells, wherein the first illumination system is further configured to supply the first bioreactor tiles with illumination light used to support production of trichomes by the cells, and wherein the first environmental control system is further configured to provide the first bioreactor tiles with one or more sets of environmental conditions that support production of trichomes by the cells.

EEE 26 is the system of any of EEEs 1-25, wherein the first fluid management system is further configured to provide one or more cleaning solutions or gases to the first bioreactor tiles in order to sterilize the first bioreactor tiles, wherein the first illumination system is further configured to supply the first bioreactor tiles with illumination light within a range of ultraviolet wavelengths in order sterilize the first bioreactor tiles, and wherein the first environmental control system is configured to heat the first bioreactor tiles to a first temperature and subsequently cool the first bioreactor tiles to a second temperature in order to sterilize the first bioreactor tiles.

EEE 27 is the system of EEE 26, wherein the first temperature is between 175° C. and 185° C., and wherein the second temperature is between 20° C. and 25° C.

EEE 28 is the system of any of EEEs 1-27, wherein the fluid management system is further configured to supply an air mixture to the first bioreactor tiles to support growth of the cells.

EEE 29 is the system of EEE 28, wherein the air mixture comprises one or more gases in one or more corresponding predefined concentrations.

EEE 30 is a method comprising:

providing, by a first fluid management system of a first bioreactor, liquid nutrient media to a plurality of first bioreactor tiles of the first bioreactor to support growth of cells housed within the first bioreactor tiles, wherein the first bioreactor tiles are positioned within a first housing of the first bioreactor, and wherein the cells are capable of producing one or more chemical products;

supplying, by a first illumination system of the first bioreactor, illumination light to the first bioreactor tiles to support growth of the cells;

providing, by a first environmental control system of the first bioreactor, the first bioreactor tiles with one or more sets of environmental conditions that support growth of the cells, wherein the first environmental control system is positioned within the first housing;

sensing, by one or more first sensors of the first bioreactor, one or more conditions associated with the first fluid management system, the first illumination system, the first environmental control system, the first bioreactor tiles, or the cells, wherein the one or more first sensors are positioned within the first housing;

receiving, by a first controller of the first bioreactor from the one or more first sensors of the first bioreactor, data regarding the one or more conditions;

providing, by the first controller based on the received data, one or more operating parameters to the first fluid management system, the first illumination system, or the first environmental control system; and harvesting, by the first fluid management system, the one or more chemical products from the first bioreactor tiles.

EEE 31 is the method of EEE 30, wherein the cells comprise parenchymal plant cells, wherein providing the liquid nutrient media to the plurality of first bioreactor tiles comprises providing calli-induction media to the first bioreactor tiles, wherein supplying the illumination light to the first bioreactor tiles to support growth of the cells comprises: supplying illumination light for about 16 hours and then supplying no illumination light for about 8 hours, and wherein providing the first bioreactor tiles with the one or more sets of environmental conditions that support growth of the cells comprises providing a temperature of between 20° C. and 25° C.

EEE 32 is the method of EEE 31, further comprising:

determining, by the first controller based on the received data, that the cells are ready to begin production of trichomes, wherein providing the one or more operating parameters to the first fluid management system, the first illumination system, or the first environmental control system comprises providing operating parameters to the first fluid management system, the first illumination system, and the first environmental control system that correspond to trichome production by the cells;

providing, by the first fluid management system, liquid nutrient media to the first bioreactor tiles to support trichome production according to the operating parameters provided by the first controller;

providing, by the first illumination system, illumination light to the first bioreactor tiles to support trichome production according to the operating parameters provided by the first controller; and providing, by the first environmental control system, the first bioreactor tiles with one or more sets of environmental conditions that support trichome production according to the operating parameters provided by the first controller.

EEE 33 is the method of EEE 32, wherein providing, by the first fluid management system, the liquid nutrient media to support trichome production comprises providing trichome-induction media to the first bioreactor tiles, wherein providing, by the first illumination system, illumination light to support trichome production comprises providing illumination light for about 12 hours and then supplying no illumination light for about 12 hours, and wherein providing, by the first environmental control system, the first bioreactor tiles with the one or more sets of environmental conditions that support trichome production comprises providing a temperature of between 20° C. and 25° C.

EEE 34 is the method of either EEE 32 or EEE 33, wherein the one or more first sensors comprise one or more imaging sensors, and wherein the received data comprises an image or other representation captured by the one or more imaging sensors of the cells.

EEE 35 is the method of EEE 34, wherein the one or more imaging sensors comprise a hyperspectral imaging sensor, wherein the image or other representation captured by the one or more imaging sensors of the cells comprises a hyperspectral representation of a spectral signature of the cells, and wherein determining, by the first controller based on the received data, that the cells are ready to begin production of trichomes comprises determining, based on the spectral signature of the cells in the hyperspectral representation, that the cells are ready to progress from a callus-growth phase to a trichome-production phase.

EEE 36 is the method of any of EEEs 30-35, further comprising determining, by the first controller based on the received data, that the one or more chemical products are ready to be harvested, wherein providing the one or more operating parameters to the first fluid management system, the first illumination system, or the first environmental control system comprises providing operating parameters to the first fluid management system that correspond to harvesting the one or more chemical products from the first bioreactor tiles.

EEE 37 is the method of EEE 36, wherein harvesting, by the first fluid management system, the one or more chemical products from the first bioreactor tiles comprises:

infusing extractant into the first bioreactor tile; and removing the infused extractant along with the one or more chemical products from the first bioreactor tiles.

EEE 38 is the method of EEE 37, wherein infusing extractant into the first bioreactor tiles comprises:

shearing trichomes produced by the cells, wherein the trichomes contain the one or more chemical products; or puncturing the trichomes produced by the cells in order to release the one or more chemical products.

EEE 39 is the method of EEE 38, wherein the one or more first sensors comprise one or more imaging sensors, and wherein the received data comprises an image or other representation captured by the one or more imaging sensors of the trichomes.

EEE 40 is the method of EEE 39, wherein the one or more imaging sensors comprise a hyperspectral imaging sensor, wherein the image or other representation captured by the one or more imaging sensors of the trichomes comprises a hyperspectral representation of a spectral signature of the trichomes, and wherein determining, by the first controller based on the received data, that the one or more chemical products are ready to be harvested comprises determining, based on the spectral signature of the trichomes in the hyperspectral representation, that the trichomes have matured to a state such that they contain a sufficient amount of the one or more chemical products.

EEE 41 is the method of any of EEEs 30-40, further comprising performing a sterilization procedure, wherein the sterilization procedure comprises:

providing, by the first fluid management system, one or more cleaning solutions or gases to the first bioreactor tiles;

supplying, by the first illumination system, the first bioreactor tiles with illumination light within a range of ultraviolet wavelengths in order sterilize the first bioreactor tiles; or heating, by the first environmental control system, the first bioreactor tiles to a first temperature and subsequently cooling the first bioreactor tiles to a second temperature.

EEE 42 is the method of EEE 41, wherein performing the sterilization procedure comprises heating, by the first environmental control system, the first bioreactor tiles to the first temperature and subsequently cooling the first bioreactor tiles to the second temperature, wherein the first temperature is between 175° C. and 185° C., and wherein the second temperature is between 20° C. and 25° C.

EEE 43 is the method of any of EEEs 30-42, further comprising supplying, by the first fluid management system of the first bioreactor, an air mixture to the first bioreactor tiles to support growth of the cells.

EEE 44 is a method comprising:

receiving, by a facility-management server from a plurality of controllers of a plurality of respective bioreactors within a facility, data regarding one or more conditions of the respective bioreactors; and providing, by the facility-management server, one or more operating parameters to at least one of the plurality of controllers based on the received data, wherein each of the respective bioreactors comprises:
a housing;
a plurality of bioreactor tiles positioned within the housing, wherein each of the bioreactor tiles is configured to house cells capable of producing one or more chemical products;
a fluid management system configured to:
provide liquid nutrient media to the bioreactor tiles to support growth of the cells; and
harvest the one or more chemical products from the bioreactor tiles;
an illumination system configured to supply the bioreactor tiles with illumination light used to support growth of the cells;
an environmental control system positioned within the housing and configured to provide the bioreactor tiles with one or more sets of environmental conditions that support growth of the cells;
one or more sensors positioned within the housing and configured to sense one or more conditions associated with the fluid management system, the illumination system, the environmental control system, the bioreactor tiles, or the cells; and
a controller configured to:
receive data regarding the one or more conditions from the one or more sensors;
provide the received data to the facility-management server;
receive one or more operating parameters from the facility-management server; and
provide, based on the received data or the one or more received operating parameters from the facility-management server, one or more operating parameters to the fluid management system, the illumination system, or the environmental control system.

EEE 45 is the method of EEE 44,
wherein providing, by the facility-management server, the one or more operating parameters to at least one of the plurality of controllers based on the received data comprises:
providing a first set of operating parameters to a first controller of a first bioreactor; and
providing a second set of operating parameters to a second controller of a second bioreactor,
wherein the first set of operating parameters causes one or more of the bioreactor tiles in the first bioreactor to begin a predetermined production phase at a first time,
wherein the second set of operating parameters causes one or more of the bioreactor tiles in the second bioreactor to begin the same predetermined production phase at a second time, and
wherein the second time is after the first time.

EEE 46 is the method of EEE 45, wherein the predetermined production phase is a sterilization phase, a seeding phase, a cellular growth phase, a callus-growth phase, a trichome-production phase, or a harvesting phase.

EEE 47 is the method of any of EEEs 44-46, further comprising:
providing, by the facility-management server, a first set of operating parameters to a first controller of a first bioreactor within the facility;
providing, by the facility-management server, a second set of operating parameters to a second controller of a second bioreactor within the facility, wherein receiving, by the facility-management server, data regarding the one or more conditions of the respective bioreactors comprises:
receiving, from the first controller, one or more conditions of the first bioreactor; and
receiving from the second controller, one or more conditions of the second bioreactor; and
determining, by the facility-management server, one or more optimized operating parameters for the second bioreactor based on:
the first set of operating parameters;
the second set of operating parameters;
the one or more conditions of the first bioreactor; and
the one or more conditions of the second bioreactor,
wherein providing, by the facility-management server, the one or more operating parameters to at least one of the plurality of controllers based on the received data comprises providing the one or more optimized operating parameters to the first controller of the first bioreactor, the second controller of the second bioreactor, or a third controller of a third bioreactor.

EEE 48 is the method of any of EEEs 44-47, wherein the facility-management server is a server device that is located remotely from the facility.

EEE 49 is the method of any of EEEs 44-48, wherein the facility-management server is a server device located within the facility.

EEE 50 is the method of any of EEEs 44-49,
wherein receiving data regarding one or more conditions of the respective bioreactors comprises receiving an indication that a first flag has been raised by a first controller of a first bioreactor within the facility,
wherein the first controller of the first bioreactor is configured to raise the first flag when the data regarding the one or more conditions from the one or more sensors of the first bioreactor corresponds to a first trigger condition,
wherein the method further comprises determining, by the facility-management server based on received indication that the first flag has been raised, the one or more operating parameters, and
wherein providing the one or more operating parameters to at least one of the plurality of controllers comprises providing the one or more operating parameters to the first controller of the first bioreactor.

EEE 51 is the method of EEE 50, wherein the first trigger condition represents a clog, a threshold change in temperature over a predetermined period of time, a threshold change in humidity over a predetermined period of time, a threshold change in pressure over a predetermined period of time, a threshold change in pH within a solution over a predetermined period of time, a threshold change in illumination intensity over a predetermined period of time, a threshold change in illumination wavelength over a predetermined period of time, a growth milestone relating to the cells in the first bioreactor, or a chemical production milestone.

EEE 52 is a system comprising a first bioreactor, wherein the first bioreactor comprises:
a first housing;
a plurality of first bioreactor tiles positioned within the first housing, wherein each of the first bioreactor tiles is configured to house cells capable of producing one or more chemical products;
a first fluid management system configured to:
provide liquid nutrient media to the first bioreactor tiles to support growth of the cells or production, by the cells, of the one or more chemical products;

supply an air mixture to the first bioreactor tiles to support growth of the cells or production, by the cells, of the one or more chemical products; and harvest the one or more chemical products from the first bioreactor tiles;

a first illumination system configured to supply the first bioreactor tiles with illumination light used to support growth of the cells or production, by the cells, of the one or more chemical products;

a first environmental control system positioned within the first housing and configured to provide the first bioreactor tiles with one or more sets of environmental conditions that support growth of the cells or production, by the cells, of the one or more chemical products;

one or more first sensors positioned within the first housing and configured to sense one or more conditions associated with the first fluid management system, the first illumination system, the first environmental control system, the first bioreactor tiles, or the cells; and a first controller configured to:

receive data regarding the one or more conditions from the one or more first sensors; and provide, based on the received data, one or more operating parameters to the first fluid management system, the first illumination system, or the first environmental control system, wherein each of the first bioreactor tiles comprises:

a substrate having a first channel, a second channel, and a third channel defined therein, wherein the first channel is separated from the second channel by a first partial wall structure, wherein the second channel is separated from the third channel by a second partial wall structure, wherein the first channel is configured to receive the liquid nutrient media from the first fluid management system, wherein the second channel is configured to house the cells capable of producing the one or more chemical products, and wherein the third channel is configured to house the one or more chemical products produced by the cells or the air mixture that supports growth of the cells or production, by the cells, of the one or more chemical products; and an optical waveguide configured to:

receive the illumination light from the first illumination system at a first end of the optical waveguide;

propagate the illumination light toward a second end of the optical waveguide;

allow at least a portion of the illumination light to escape the optical waveguide from a first surface of the optical waveguide as the illumination light propagates toward the second end of the optical waveguide; and provide the portion of the illumination light that escapes the optical waveguide from the first surface to the second channel or the third channel to support growth of the cells or production, by the cells, of the one or more chemical products.

EEE 53 is a method comprising:

providing, by a first fluid management system of a first bioreactor, liquid nutrient media to a plurality of first bioreactor tiles of the first bioreactor to support growth of cells housed within the first bioreactor tiles or production, by the cells housed within the first bioreactor tiles, one or more chemical products, and wherein the first bioreactor tiles are positioned within a first housing of the first bioreactor;

supplying, by the first fluid management system, an air mixture to the first bioreactor tiles to support growth of the cells or production, by the cells, of the one or more chemical products;

supplying, by a first illumination system of the first bioreactor, illumination light to the first bioreactor tiles to support growth of the cells or production, by the cells, of the one or more chemical products;

providing, by a first environmental control system of the first bioreactor, the first bioreactor tiles with one or more sets of environmental conditions that support growth of the cells or production, by the cells, of the one or more chemical products, wherein the first environmental control system is positioned within the first housing;

sensing, by one or more first sensors of the first bioreactor, one or more conditions associated with the first fluid management system, the first illumination system, the first environmental control system, the first bioreactor tiles, or the cells, wherein the one or more first sensors are positioned within the first housing;

receiving, by a first controller of the first bioreactor from the one or more first sensors of the first bioreactor, data regarding the one or more conditions;

providing, by the first controller based on the received data, one or more operating parameters to the first fluid management system, the first illumination system, or the first environmental control system; and harvesting, by the first fluid management system, the one or more chemical products from the first bioreactor tiles, wherein each of the first bioreactor tiles comprises:

a substrate having a first channel, a second channel, and a third channel defined therein, wherein the first channel is separated from the second channel by a first partial wall structure, wherein the second channel is separated from the third channel by a second partial wall structure, wherein the first channel is configured to receive the liquid nutrient media from the first fluid management system, wherein the second channel is configured to house the cells capable of producing the one or more chemical products, and wherein the third channel is configured to house the one or more chemical products produced by the cells or the air mixture that supports growth of the cells or production, by the cells, of the one or more chemical products; and an optical waveguide configured to:

receive the illumination light from the first illumination system at a first end of the optical waveguide;

propagate the illumination light toward a second end of the optical waveguide;

allow at least a portion of the illumination light to escape the optical waveguide from a first surface of the optical waveguide as the illumination light propagates toward the second end of the optical waveguide; and provide the portion of the illumination light that escapes the optical waveguide from the first surface to the second channel or the third channel to support growth of the cells or production, by the cells, of the one or more chemical products.

EEE 54 is a method comprising:

receiving, by a facility-management server from a plurality of controllers of a plurality of respective bioreactors within a facility, data regarding one or more conditions of the respective bioreactors; and providing, by the facility-management server, one or more operating parameters to at least one of the plurality of controllers based on the received data, wherein each of the respective bioreactors comprises:

a housing;

a plurality of bioreactor tiles positioned within the housing, wherein each of the bioreactor tiles is configured to house cells capable of producing one or more chemical products;

a fluid management system configured to:

provide liquid nutrient media to the bioreactor tiles to support growth of the cells or production, by the cells, of the one or more chemical products;

supply an air mixture to the bioreactor tiles to support growth of the cells or production, by the cells, of the one or more chemical products; and harvest the one or more chemical products from the bioreactor tiles;

an illumination system configured to supply the bioreactor tiles with illumination light used to support growth of the cells or production, by the cells, of the one or more chemical products;

an environmental control system positioned within the housing and configured to provide the bioreactor tiles with one or more sets of environmental conditions that support growth of the cells or production, by the cells, of the one or more chemical products;

one or more sensors positioned within the housing and configured to sense one or more conditions associated with the fluid management system, the illumination system, the environmental control system, the bioreactor tiles, or the cells; and a controller configured to:

receive data regarding the one or more conditions from the one or more sensors;

provide the received data to the facility-management server;

receive one or more operating parameters from the facility-management server; and provide, based on the received data or the one or more received operating parameters from the facility-management server, one or more operating parameters to the fluid management system, the illumination system, or the environmental control system, wherein each of the bioreactor tiles comprises:

a substrate having a first channel, a second channel, and a third channel defined therein, wherein the first channel is separated from the second channel by a first partial wall structure, wherein the second channel is separated from the third channel by a second partial wall structure, wherein the first channel is configured to receive the liquid nutrient media from the fluid management system, wherein the second channel is configured to house the cells capable of producing the one or more chemical products, and wherein the third channel is configured to house the one or more chemical products produced by the cells or the air mixture that supports growth of the cells or production, by the cells, of the one or more chemical products; and an optical waveguide configured to:

receive the illumination light from the illumination system at a first end of the optical waveguide;

propagate the illumination light toward a second end of the optical waveguide:

allow at least a portion of the illumination light to escape the optical waveguide from a first surface of the optical waveguide as the illumination light propagates toward the second end of the optical waveguide; and provide the portion of the illumination light that escapes the optical waveguide from the first surface to the second channel or the third channel to support growth of the cells or production, by the cells, of the one or more chemical products.

What is claimed:

1. A system comprising a first bioreactor, wherein the first bioreactor comprises:

a first housing;

a plurality of first bioreactor tiles positioned within the first housing, wherein each of the first bioreactor tiles comprises a substrate defining a first channel, a second channel, and a third channel, the first channel being separated from the second channel by a first partial wall structure and the second channel being separated from the third channel by a second partial wall structure;

a first fluid management system configured to provide liquid nutrient media to the first bioreactor tiles to support growth of the cells and harvest the one or more chemical products from the first bioreactor tiles;

a first illumination system configured to supply the first bioreactor tiles with illumination light used to support growth of the cells;

an optical waveguide associated with each tile and configured to receive illumination light from the illumination system at a first end, propagate the illumination toward a second end, allow at least a portion of the illumination to escape from a first surface along the length of the waveguide, and provide the escaped illumination to the second channel or the third channel;

a first environmental control system positioned within the first housing and configured to provide the first bioreactor tiles with one or more sets of environmental conditions that support growth of the cells;

one or more first sensors positioned within the first housing and configured to sense one or more conditions associated with the first fluid management system, the first illumination system, the first environmental control system, the first bioreactor tiles, or the cells; and a first controller configured to:

receive data regarding the one or more conditions from the one or more first sensors;

determining an instruction to address the one or more conditions; and provide, based on the received data, one or more operating parameters to the first fluid management system, the first illumination system, or the first environmental control system to address the one or more conditions.

2. The system of claim 1, wherein the first channel is configured to receive the liquid nutrient media from the first fluid management system, wherein the second channel is configured to house the cells capable of producing the one or more chemical products, and wherein the third channel is configured to house the one or more chemical products produced by the cells.

3. The system of claim 2, wherein the third channel is further configured to house an air mixture, and wherein the air mixture is configured to enable gas exchange for the cells.

4. The system of claim 1, further comprising a second bioreactor, wherein the second bioreactor comprises:

a second housing;

a plurality of second bioreactor tiles positioned within the second housing, wherein each of the second bioreactor tiles is configured to house cells capable of producing one or more chemical products;

a second fluid management system configured to:

provide liquid nutrient media to the second bioreactor tiles to support growth of the cells in the second bioreactor; and harvest the one or more chemical products from the second bioreactor tiles;

a second illumination system configured to supply the second bioreactor tiles with illumination light used to support growth of the cells in the second bioreactor;

a second environmental control system positioned within the second housing and configured to provide the second bioreactor tiles with one or more sets of environmental conditions that support growth of the cells in the second bioreactor;

one or more second sensors positioned within the second housing and configured to sense one or more conditions associated with the second fluid management system, the second illumination system, the second environmental control system, the second bioreactor tiles, or the cells in the second bioreactor, and a second controller configured to:

receive data regarding the one or more conditions from the one or more second sensors; and provide, based on the received data, one or more operating parameters to the second fluid management system, the second illumination system, or the second environmental control system.

5. The system of claim 4, further comprising a bioreactor facility, wherein the first bioreactor and the second bioreactor are located within the bioreactor facility.

6. The system of claim 5, further comprising a facility-management server, wherein the facility-management server is configured to:

communicate with the first controller to:

receive data regarding the one or more conditions from the one or more first sensors; and receive the one or more operating parameters provided to the first fluid management system, the first illumination system, or the first environmental control system;

communicate with the second controller to:

receive data regarding the one or more conditions from the one or more second sensors; and receive the one or more operating parameters provided to the second fluid management system, the second illumination system, or the second environmental control system;

determine, based on: (i) the one or more conditions from the one or more first sensors; (ii) the one or more operating parameters provided to the second fluid management system, the second illumination system, or the second environmental control system; or (iii) the one or more conditions from the one or more second sensors, one or more revised operating parameters for the first fluid management system, the first illumination system, or the first environmental control system;

determine, based on: (i) the one or more conditions from the one or more second sensors; (ii) the one or more operating parameters provided to the first fluid management system, the first illumination system, or the first environmental control system; or (iii) the one or more conditions from the one or more first sensors, one or more revised operating parameters for the second fluid management system, the second illumination system, or the second environmental control system;

provide, to the first controller, the one or more revised operating parameters for the first fluid management system, the first illumination system, or the first environmental control system; and provide, to the second controller, the one or more revised operating parameters for the second fluid management system, the second illumination system, or the second environmental control system.

7. The system of claim 6, wherein the first controller is configured to raise a first flag when the data regarding the one or more conditions from the one or more first sensors corresponds to a first trigger condition, wherein the second controller is configured to raise a second flag when the data regarding the one or more conditions from the one or more second sensors corresponds to a second trigger condition, wherein:

receiving the data regarding the one or more conditions from the one or more first sensors comprises identifying that the first flag is raised; or receiving the data regarding the one or more conditions from the one or more second sensors comprises identifying that the second flag is raised.

8. The system of claim 7, wherein the first trigger condition or the second trigger condition represents: a clog, a threshold change in temperature over a predetermined period of time, a threshold change in humidity over a predetermined period of time, a threshold change in pressure over a predetermined period of time, a threshold change in pH within a solution over a predetermined period of time, a threshold change in illumination intensity over a predetermined period of time, a threshold change in illumination wavelength over a predetermined period of time, a growth milestone relating to the cells in the first bioreactor, a growth milestone relating to the cells in the second bioreactor, or a chemical production milestone.

9. The system of claim 6, further comprising a facility-wide environmental control system positioned within the facility and configured to provide the first bioreactor and the second bioreactor with one or more sets of external environmental conditions, wherein the facility-management server is configured to provide one or more operating parameters to the facility-wide environmental control system, wherein the first environmental control system is configured to augment the one or more sets of external environmental conditions to provide the first bioreactor tiles with the one or more sets of environmental conditions that support growth of the cells, and wherein the second environmental control system is configured to augment the one or more sets of external environmental conditions to provide the second bioreactor tiles with the one or more sets of environmental conditions that support growth of the cells.

10. The system of claim 6, further comprising a facility-wide fluid management system positioned within the facility and configured to provide the first bioreactor and the second bioreactor with one or more fluids used for operation or retrieve the one or more chemical products from the products from the first bioreactor and the second bioreactor.

11. The system of claim 10, wherein the facility comprises a floor surface and a subfloor surface, and wherein the facility-wide fluid management system comprises pipes, pumps, chambers, reservoirs, tanks, or valves located between the floor surface and the subfloor surface.

* * * * *